United States Patent
Claiborne et al.

(10) Patent No.: US 7,718,648 B2
(45) Date of Patent: May 18, 2010

(54) PYRIDOBENZAZEPINE COMPOUNDS AND METHODS FOR INHIBITING MITOTIC PROGRESSION

(75) Inventors: Christopher F. Claiborne, Cambridge, MA (US); Todd B. Sells, Bellingham, MA (US); Stephen G. Stroud, Medford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/890,406

(22) Filed: Aug. 6, 2007

(65) Prior Publication Data

US 2008/0045501 A1 Feb. 21, 2008

Related U.S. Application Data

(60) Provisional application No. 60/836,605, filed on Aug. 9, 2006.

(51) Int. Cl.
*A61P 35/00* (2006.01)
*A61K 31/55* (2006.01)
*C07D 487/00* (2006.01)

(52) U.S. Cl. .................. 514/215; 540/577; 540/578
(58) Field of Classification Search .............. 514/215; 540/577, 578
See application file for complete search history.

(56) References Cited

U.S. PATENT DOCUMENTS

| | | | |
|---|---|---|---|
| 4,099,012 | A | 7/1978 | Gschwend |
| 4,469,633 | A | 9/1984 | Trybulski |
| 4,481,142 | A | 11/1984 | Fryer et al. |
| 5,166,151 | A | 11/1992 | Freidinger et al. |
| 5,210,082 | A | 5/1993 | Bock et al. |
| 6,057,329 | A | 5/2000 | Davis et al. |
| 6,277,844 | B1 | 8/2001 | Spector |
| 2003/0022885 | A1 | 1/2003 | Bebbington et al. |
| 2003/0055068 | A1 | 3/2003 | Bebbington et al. |

FOREIGN PATENT DOCUMENTS

| | | |
|---|---|---|
| EP | 0 014 470 B1 | 7/1985 |
| EP | 0 273 697 A2 | 7/1988 |
| WO | WO 00/67754 A1 | 11/2000 |
| WO | WO 03/013545 A1 | 2/2003 |
| WO | WO 2005/037843 A1 | 4/2005 |
| WO | WO 2005/111039 A2 | 11/2005 |
| WO | WO 2006/070198 A1 | 7/2006 |

OTHER PUBLICATIONS

Meraldi, Patrick, et al., "Aurora-A Overexpression Reveals Tetraploidization as a Major Route to Centrosome Amplification in $p53^{-/-}$ Cells," *The EMBO Journal*, vol. 21, No. 4 (2002) pp. 483-492.
Harrington, Elizabeth A., et al., "VX-680, A Potent and Selective Small-Molecule Inhibitor of the Aurora Kinases, Suppresses Tumor Growth In Vivo," *Nature Medicine* (Feb. 22, 2004) pp. 1-6.
Ditchfield, Claire, et al., "Aurora B Couples Chromosome Alignment With Anaphase by Targeting BubR1, Mad2, and Cenp-E to Kinetochores," *The Journal of Cell Biology*, vol. 161, No. 2 (Apr. 28, 2003) pp. 267-280.
Sausville, Edward A.,"Aurora Kinases Dawn as Cancer Drug Targets," *Nature Medicine*, vol. 10, No. 3 (Mar. 2004) pp. 234-235.
Silke, Hauf, et al., "The Small Molecule Hesperadin Reveals a Role for Aurora B in Correcting Kinetochore-Microtubule Attachment and in Maintaining the Spindle Assembly Checkpoint," *The Journal of Cell Biology*, vol. 161, No. 2 (Apr. 28, 2003) pp. 281-294.
Bischoff, James R., et al., "A Homologue of *Drosophila* Aurora Kinase is Oncogenic and Amplified in Human Colorectal Cancers," *The EMBO Journal*, vol. 17, No. 11 (1998) pp. 3052-3065.
Zhou, Hongyi, et al., "Tumour Amplified Kinase STK15/BTAK Induces Centrosome Amplification, Aneuploidy and Transformation," *Nature Genetics*, vol. 20 (Oct. 1998) pp. 189-193.
Xia, Wenle, et al., "Tumor Selective $G_2$/M Cell Cycle Arrest and Apoptosis of Epithelial and Hematological Malignancies by BBL22, a Benzazepine," *Proceedings of the National Academy of Sciences USA*, vol. 97, No. 13 (Jun. 20, 2000) pp. 7494-7499.
Wang, James K.T., et al., "Benzodiazepines that Bind at Peripheral Sites Inhibit Cell Proliferation," *Proceedings of the National Academy of Sciences USA*, vol. 81 (Feb. 1984) pp. 753-756.
Cantor, E.H., et al., "Interaction of Calcium Channel Blockers with Non-Neuronal Benzodiazepine Binding Sites," *Proceedings of the National Academy of Sciences USA*, vol. 81 (Mar. 1984) pp. 1549-1552.
Solowey, Wendy E., et al., "Peripheral-Acting Benzodiazepines Inhibit the Growth of Human Melanoma Cells and Potentiate the Antiproliferative Activity of Recombinant Human Interferons," *The Journal of Interferon Research*, vol. 10, No. 3 (Jun. 1990) pp. 269-280.
Vankayalapati, Hariprasad, et al., "Targeting Aurora2 Kinase in Oncogenesis: A Structural Bioinformatics Approach to Target Validation and Rational Drug Design," *Molecular Cancer Therapeutics*, vol. 2 (Mar. 2003) pp. 283-294.
Carmena, Mar, et al., "The Cellular Geography of Aurora Kinases," *Nature Reviews*, vol. 4 (Nov. 2003) pp. 842-854.
PCT Search Report and Written Opinion of the International Searching Authority dated Dec. 7, 2005 in International Application No. PCT/US/05/16445 (WO05/111039), Jul. 12, 2005.
PCT Search Report and Written Opinion of the International Searching Authority dated May 9, 2008 in International Application No. PCT/US07/017432.

*Primary Examiner*—Brenda L Coleman

(57) ABSTRACT

This invention relates to compounds and methods for the treatment of cancer. In particular, the invention provides compounds that inhibit Aurora kinase, pharmaceutical compositions comprising the compounds, and methods of using the compounds for the treatment of cancer.

50 Claims, No Drawings

PYRIDOBENZAZEPINE COMPOUNDS AND METHODS FOR INHIBITING MITOTIC PROGRESSION

PRIORITY CLAIM

This application claims priority from U.S. Provisional Patent Application Ser. No. 60/836,605, filed on Aug. 9, 2006, which is hereby incorporated by reference in its entirety.

BACKGROUND OF THE INVENTION

1. Field of the Invention

This invention relates to compounds and methods for the treatment of cancer. In particular, the invention provides compounds that inhibit Aurora kinase enzymes, pharmaceutical compositions comprising the compounds, and methods of using the compounds for the treatment of cancer.

2. Background of the Invention

According to the American Cancer Society, an estimated 1.4 million Americans were newly-diagnosed with cancer in 2004 and about 560,000 victims died from the disease. While medical advance have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene*, 21: 6175 (2002); Berdnik et al., *Curr. Biol.*, 12: 640 (2002)). Overexpression and/or amplification of Aurora kinases have been linked to oncogenesis in several tumor types including those of colon and breast (Warner et al., *Mol. Cancer Ther.*, 2: 589 (2003); Bischoff et al., *EMBO*, 17: 3062 (1998); Sen et al., *Cancer Res.*, 94: 1320 (2002)). Moreover, Aurora kinase inhibition in tumor cells results in mitotic arrest and apoptosis, suggesting that these kinases are important targets for cancer therapy (Ditchfield, *J. Cell Biol.*, 161: 267 (2003); Harrington et al., *Nature Med.*, 1 (2004)). Given the central role of mitosis in the progression of virtually all malignancies, inhibitors of the Aurora kinases are expected to have application across a broad range of human tumors. There is thus a need for new Aurora kinase inhibitors.

DESCRIPTION OF THE INVENTION

This invention provides compounds that inhibit Aurora kinase. These compounds are useful for inhibiting Aurora kinase in vitro or in vivo, and are especially useful for the treatment of cell proliferative disorders, including cancer. The Aurora kinase inhibitors of the invention have the formula (I):

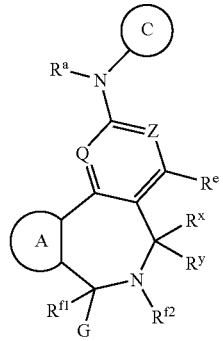

or a pharmaceutically acceptable salt thereof, wherein Ring A, Ring C, and each of the variables $R^a$, $R^e$, $R^{f1}$, $R^{f2}$, $R^x$, $R^y$, Q, Z, and G have the values described below.

$R^{f1}$ is hydrogen, or $R^{f1}$ and $R^{f2}$ together form a bond.

$R^{f2}$ is hydrogen, or $R^{f2}$ forms a bond with either $R^{f1}$ or $R^x$.

$R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring; or $R^x$ and $R^{f2}$ together form a bond.

One of Q and Z is —N—, and the other is —CH—.

G is hydrogen, an optionally substituted aliphatic, or Ring B when $R^{f1}$ is hydrogen; and G is hydrogen, —$OR^5$, —$N(R^4)_2$, —$SR^5$, an optionally substituted aliphatic, or Ring B when $R^{f1}$ and $R^{f2}$ together form a bond.

Ring A is a substituted or unsubstituted 5- or 6-membered aryl, heteroaryl, cycloaliphatic, or heterocyclyl ring.

Ring B is a substituted or unsubstituted aryl, heteroaryl, cycloaliphatic, or heterocyclyl ring.

Ring C is a substituted or unsubstituted aryl, heteroaryl, heterocyclyl, or cycloaliphatic ring.

$R^a$ is hydrogen, —$C(O)R^1$, —$CO_2R^1$, —$SO_2R^1$, or a $C_{1-3}$ aliphatic having 0-2 substituents independently selected from $R^3$ or $R^7$.

$R^e$ is hydrogen, —$OR^5$, —$N(R^4)_2$, —$SR^5$, —$NR^4C(O)R^5$, —$NR^4C(O)N(R^4)_2$, —$NR^4CO_2R^6$, —$N(R^4)SO_2R^6$, —$N(R^4)SO_2N(R^4)_2$, or a $C_{1-3}$ aliphatic optionally substituted with $R^3$ or $R^7$.

$R^1$ is $C_{1-6}$ aliphatic or an optionally substituted aryl, heteroaryl, or heterocyclyl group.

Each $R^3$ independently is selected from the group consisting of -halo, —OH, —O($C_{1-3}$ alkyl), —CN, —$N(R^4)_2$, —C(O)($C_{1-3}$ alkyl), —$CO_2H$, —$CO_2(C_{1-3}$ alkyl), —$C(O)NH_2$, and —$C(O)NH(C_{1-3}$ alkyl).

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4 to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group.

Each $R^6$ independently is an optionally substituted aliphatic or aryl group.

Each $R^7$ independently is an optionally substituted aryl, heterocyclyl, or heteroaryl group.

The invention further provides pharmaceutical compositions comprising a compound of formula (I), as well as uses of the claimed compounds for inhibiting Aurora kinase activity and for treating Aurora kinase-mediated disorders.

Compounds of this invention include those described generally above, and are further illustrated by the classes, subclasses, and species disclosed herein. Terms used herein shall be accorded the following defined meanings, unless otherwise indicated.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p 53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound having a structure as defined herein, which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, less than about 100 nM, or less than about 50 nM.

In some embodiments, such inhibition is selective, i.e., the Aurora kinase inhibitor reduces the ability of an Aurora kinase to phosphorylate a substrate peptide or protein at a concentration that is lower than the concentration of the inhibitor that is required to produce another, unrelated biological effect, e.g., reduction of the enzymatic activity of a different kinase. In some embodiments, the Aurora kinase inhibitor also reduces the enzymatic activity of another kinase, preferably one that is implicated in cancer.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

The term "aliphatic", as used herein, means straight-chain, branched or cyclic $C_{1-12}$ hydrocarbons which are completely saturated or which contain one or more units of unsaturation, but which are not aromatic. For example, suitable aliphatic groups include substituted or unsubstituted linear, branched or cyclic alkyl, alkenyl, or alkynyl groups and hybrids thereof, such as (cylcoalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The terms "cycloaliphatic", "carbocycle", "carbocyclyl", "carbocyclo", or "carbocyclic", used alone or as part of a larger moiety, refer to a saturated or partially unsaturated cyclic aliphatic ring system having from 3 to about 14 members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3 to 6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case may be, substituted with one or more halogen atoms. As used herein, the term "halogen" or "halo" means F, Cl, Br, or I.

The terms "aryl" and "ar-", used alone or as part of a larger moiety, e.g., "aralkyl", "aralkoxy", or "aryloxyalkyl", refer to a $C_6$ to $C_{14}$ aromatic moiety comprising one to three aromatic rings, which are optionally substituted. Preferably, the aryl group is a $C_{6-10}$ aryl group. Aryl groups include, without limitation, phenyl, naphthyl, and anthracenyl. The term "aryl", as used herein, also includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to aromatic groups having 5 to 14 ring atoms, preferably 5, 6, 9, or 10 ring atoms; having 6, 10, or 14π electrons shared in a cyclic array; and having, in addition to one or more carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6 to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl).

A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as —NH—, —$CH_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R^)—, —C≡C—, —O—, —S—, —S(O)—, —$S(O)_2$—, —$S(O)_2N(R^+)$—, —N(R*)—, —$N(R^+)CO$—, —$N(R^+)C(O)N(R^+)$—, —$N(R^+)CO_2$—, —$C(O)N(R^+)$—, —C(O)—, —C(O)—C(O)—, —$CO_2$—, —OC(O)—, —OC(O)O—, —OC(O)N(R^+)—, —$C(NR^+)$=N, —$C(OR^*)$=N—, —$N(R^+)$—N(R^+)—, or —$N(R^+)S(O)_2$—. Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group. Each R^ independently is hydrogen —$CO_2R^*$, —$C(O)N(R^+)_2$, or an optionally substituted aliphatic, aryl, heteroaryl, or heterocyclyl group.

Examples of $C_{3-6}$ alkylene chains that have been "interrupted" with —O— include —$CH_2OCH_2$—, —$CH_2O(CH_2)_2$—, —$CH_2O(CH_2)_3$—, —$CH_2O(CH_2)_4$—, —$(CH_2)_2OCH_2$—, —$(CH_2)_2O(CH_2)_2$—, —$(CH_2)_2O(CH_2)_3$—, —$(CH_2)_3O(CH_2)$—, —$(CH_2)_3O(CH_2)_2$—, and —$(CH_2)_4O(CH_2)$—. Other examples of alkylene chains that are "interrupted" with functional groups include —$CH_2GCH_2$—, —$CH_2G(CH_2)_2$—, —$CH_2G(CH_2)_3$—, —$CH_2G(CH_2)_4$—, —$(CH_2)_2GCH_2$—, —$(CH_2)_2G(CH_2)_2$—, —$(CH_2)_2G(CH_2)_3$—, —$(CH_2)_3G(CH_2)$—, —$(CH_2)_3G(CH_2)_2$—, and —$(CH_2)_4G(CH_2)$—, wherein G is one of the "interrupting" functional groups listed above.

The term "substituted", as used herein, means that one or more hydrogens of the designated moiety are replaced, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=C(R*)(R^), —C≡C—R^, —OR*, —SR°, —S(O)R°, —$SO_2$R°, —$SO_3$R*, —$SO_2$N($R^+$)$_2$, —N($R^+$)$_2$, —$NR^+$C(O)R*, —$NR^+$C(O)N($R^+$)$_2$, —$NR^+CO_2$R°, —O—$CO_2$R*, —OC(O)N($R^+$)$_2$, —O—C(O)R*, —$CO_2$R*, —C(O)—C(O)R*, —C(O)R*, —C(O)N($R^+$)$_2$, —C(O)N($R^+$)C(=$NR^+$)—N($R^+$)$_2$, —N($R^+$)C(=$NR^+$)—N($R^+$)—C(O)R*, —C(=$NR^+$)—N($R^+$)$_2$, —C(=$NR^+$)—OR*, —N($R^+$)—N($R^+$)$_2$, —N($R^+$)C(=$NR^+$)—N($R^+$)$_2$, —NR*$SO_2$R°, —$NR^+SO_2$N($R^+$)$_2$, —P(O)(R*)$_2$, —P(O)(OR*)$_2$, —O—P(O)—OR*, and —P(O)($NR^+$)—N($R^+$)$_2$, or two adjacent substituents, taken together with their intervening atoms, form a 5-6 membered unsaturated or partially unsaturated ring having 0-3 ring atoms selected from the group consisting of N, O, and S. In such substituents, R° is an optionally substituted aliphatic or aryl group, and $R^+$, R*, and R^ are as defined above.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—NHR*, =N—N(R*)$_2$, =N—OR*, =N—NHC(O)R*, =N—$NHCO_2$R°, =N—$NHSO_2$R°, or =N—R*, where each R* and R° is as defined above.

Suitable substituents on the nitrogen atom of a non-aromatic heterocyclic ring include —R*, —N(R*)$_2$, —C(O)R*, —$CO_2$R*, —C(O)—C(O)R*—C(O)$CH_2$C(O)R*, —$SO_2$R*, —$SO_2$N(R*)$_2$, —C(=S)N(R*)$_2$, —C(=NH)—N(R*)$_2$, and —NR*$SO_2$R*; wherein each R* is as defined above.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. By way of example, the compounds of formula (I) wherein $R^{f1}$ is hydrogen can have R or S configuration at the carbon atom bearing Ring B. Both the R and the S stereochemical isomers, as well as all mixtures thereof, are included within the scope of the invention.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Unless otherwise stated, structures depicted herein are also meant to include solvated and hydrated forms of the depicted compounds. Also included within the scope of the invention are pharmaceutically acceptable salts of compounds of formula (I), as well as solvated and hydrated forms of such salts.

In the compounds of formula (I), $R^e$ is hydrogen, —$OR^5$, —N($R^4$)$_2$, —$SR^5$, —$NR^4$C(O)$R^5$, —$NR^4$C(O)N($R^4$)$_2$, —$NR^4CO_2R^6$, —N($R^4$)$SO_2R^6$, —N($R^4$)$SO_2$N($R^4$)$_2$, or a $C_{1-3}$ aliphatic optionally substituted with $R^3$ or $R^7$. In some embodiments, $R^e$ is hydrogen or a $C_{1-3}$ aliphatic optionally substituted with one $R^3$ or $R^7$. In certain embodiments, $R^e$ is hydrogen.

In some embodiments, $R^x$ and $R^y$ are each independently selected from hydrogen, fluoro, or a $C_{1-6}$ aliphatic optionally substituted with one or two $R^3$. In some other embodiments, $R^x$ and $R^y$, taken together with the carbon atom to which they are attached, form an optionally substituted 3- to 6-membered cycloaliphatic ring. In some other embodiments, $R^x$ and $R^{f2}$ together form a bond. In some embodiments, $R^x$ and $R^y$ are each hydrogen. In certain embodiments, $R^x$, $R^y$, and $R^e$ are each hydrogen.

Some embodiments of the invention relate to compounds of formula (I) where $R^{f1}$ is hydrogen, $R^{f2}$ is hydrogen or $R^{f2}$ and $R^x$ together form a bond, and G is hydrogen, an optionally substituted aliphatic, or Ring B.

Some other embodiments relate to compounds of formula (I), where $R^{f1}$ and $R^{f2}$ together form a bond, and G is hydrogen, —$SR^5$, —$OR^5$, —N($R^4$)$_2$, or an optionally substituted aliphatic. In such embodiments, G preferably is hydrogen, —$OR^5$, —N($R^4$)$_2$ or an optionally substituted aliphatic. More preferably, G is —H, —OH, —$NH_2$, —O($C_{1-3}$ alkyl), —NH($C_{1-3}$ alkyl), —N($C_{1-3}$ alkyl)$_2$, $C_{1-3}$ alkyl, $C_{1-3}$ fluoroalkyl, —O-$L^1$-$R^7$, —N($C_{1-3}$ alkyl)-$L^1$-$R^7$, or -$L^1$-$R^7$, where $L^1$ is a covalent bond or $C_{1-3}$ alkylene.

Other embodiments of the invention relate to a subgenus of formula (I) defined by formula (II):

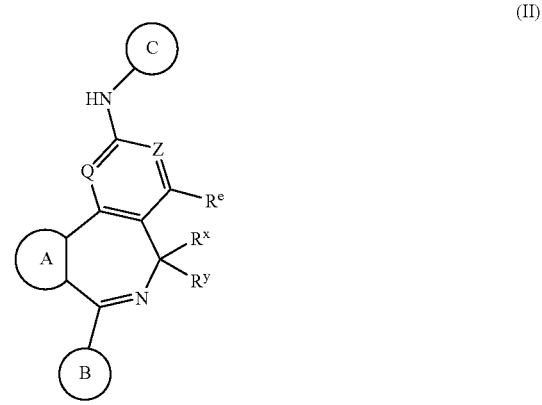

(II)

or a pharmaceutically acceptable salt thereof, where the variables $R^e$, $R^x$, and $R^y$ are as defined for formula (I). Values and preferred values for Rings A, B, and C in formulae (I) and (II) are described below.

Ring A is a substituted or unsubstituted 5- or 6-membered aryl, heteroaryl, cycloaliphatic, or heterocyclyl ring. Examples of Ring A include furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino, any of which groups may be substituted or unsubstituted. Preferred values for Ring A include, without limitation, substituted or unsubstituted rings selected from the group consisting of furano, thieno, pyrrolo, oxazolo, thiazolo, imidazolo, pyrazolo, isoxazolo, isothiazolo, triazolo, benzo, pyridino, pyridazino, pyrimidino, and pyrazino.

Ring A may be substituted or unsubstituted. In some embodiments, each substitutable saturated ring carbon atom in Ring A is unsubstituted or is substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^b$, where $R^b$, $R^4$, $R^5$, and $R^6$ are as defined below. Each substitutable unsaturated ring carbon atom in Ring A is unsubstituted or substituted with —$R^b$. Each substitutable ring nitrogen atom in Ring A is unsubstituted or is substituted with —$R^{9b}$, and one ring nitrogen atom in Ring A optionally is oxidized. Each $R^{9b}$ independently is —C(O)$R^5$, —C(O)N($R^4$)$_2$, —CO$_2R^6$, —SO$_2R^6$, —SO$_2$N($R^4$)$_2$, or a $C_{1-4}$ aliphatic optionally substituted with $R^3$ or $R^7$.

Each $R^b$ independently is $R^{2b}$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S.

Each $R^{2b}$ independently is -halo, —NO$_2$, —CN, —C($R^5$)=C($R^5$)$_2$, —C($R^5$)=C($R^5$)($R^{10}$), —C≡C—$R^5$, —C≡C—$R^{10}$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —O—CO$_2R^5$, —OC(O)N($R^4$)$_2$, —O—C(O)$R^5$, —CO$_2R^5$, —C(O)—C(O)$R^5$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, or —P(O)(O$R^5$)$_2$.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl).

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group;

Each $R^6$ independently is an optionally substituted aliphatic or aryl group;

Each $R^7$ independently is an optionally substituted aryl, heterocyclyl, or heteroaryl group;

Each $R^{10}$ independently is —CO$_2R^5$ or —C(O)N($R^4$)$_2$.

In some embodiments, each $R^b$ independently is selected from the group consisting of $C_{1-6}$ aliphatic, $C_{1-6}$ fluoroaliphatic, —$R^{2b}$, —$R^{7b}$, -$T^1$-$R^{2b}$, and -$T^1$-$R^{7b}$; or two adjacent $R^b$, taken together with the intervening ring atoms, form an optionally substituted fused 4- to 8-membered aromatic or non-aromatic ring having 0-3 ring heteroatoms selected from the group consisting of O, N, and S. The variable $R^{2b}$ is as described above, and $T^1$ and $R^{7b}$ are described below.

$T^1$ is a $C_{1-6}$ alkylene chain optionally substituted with $R^3$ or $R^{3b}$, wherein $T^1$ or a portion thereof optionally forms part of a 3- to 7-membered ring.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl).

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7b}$ independently is an optionally substituted aryl, heteroaryl, or heterocyclyl group.

In some embodiments, Ring A is substituted with 0-3, 0-2, or 0-1 substituents $R^b$, wherein the substituents $R^b$ may be the same or different. In some embodiments, each $R^b$ independently is selected from the group consisting of $C_{1-3}$ aliphatic, $R^{2b}$, $R^{7b}$, -$T^1$-$R^{2b}$, and -$T^1$-$R^{7b}$, where $T^1$ is a $C_{1-3}$ alkylene chain optionally substituted with fluoro. In some embodiments, two adjacent $R^b$, taken together with the intervening ring carbon atoms, form an optionally substituted fused 4- to 8-membered aromatic or non-aromatic ring having 0-3 ring heteroatoms selected from the group consisting of O, N, and S. In some embodiments, each $R^b$ independently is selected from the group consisting of $C_{1-3}$ aliphatic, $R^{2b}$, and -$T^1$-$R^{2b}$, where $T^1$ is a $C_{1-3}$ alkylene chain, optionally substituted with fluoro. In some such embodiments, each $R^{2b}$ independently is selected from the group consisting of -halo, —NO$_2$, —C($R^5$)=C($R^5$)$_2$, —C≡C—$R^5$, —O$R^5$, and —N($R^4$)$_2$.

In some embodiments, Ring A is substituted by 0-2 substituents $R^b$. In some such embodiments, each $R^b$ independently is $C_{1-3}$ aliphatic or $R^{2b}$, and each $R^{2b}$ independently is selected from the group consisting of -halo, —NO$_2$, —C($R^5$)=C($R^5$)$_2$, —C≡C—$R^5$, —O$R^5$, and —N($R^4$)$_2$. In some embodiments, each $R^b$ independently is selected from the group consisting of -halo, $C_{1-3}$ aliphatic, $C_{1-3}$ fluoroaliphatic, and —O$R^5$, where $R^5$ is hydrogen or $C_{1-3}$ aliphatic. In certain preferred embodiments, Ring A is substituted with 0, 1, or 2 substituents, preferably 0 or 1 substituents, independently selected from the group consisting of chloro, fluoro, bromo, methyl, trifluoromethyl, and methoxy.

Certain examples of Ring A moieties are shown in Table 1. For ease of viewing, the optional substituents $R^b$ on ring carbon atoms and $R^{9b}$ on ring nitrogen atoms are not shown.

TABLE 1

Examples of Ring A Moieties

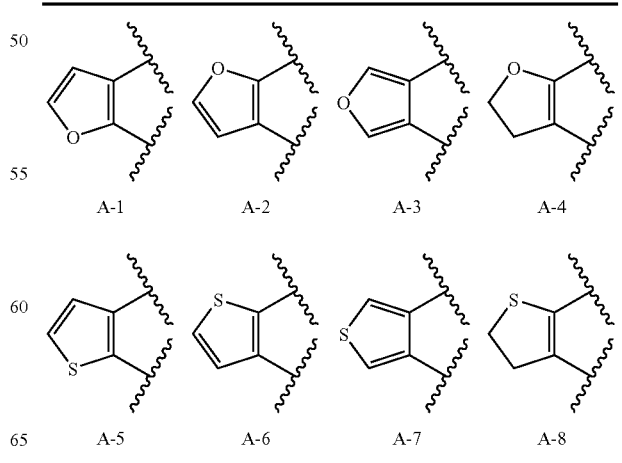

A-1  A-2  A-3  A-4

A-5  A-6  A-7  A-8

TABLE 1-continued

Examples of Ring A Moieties

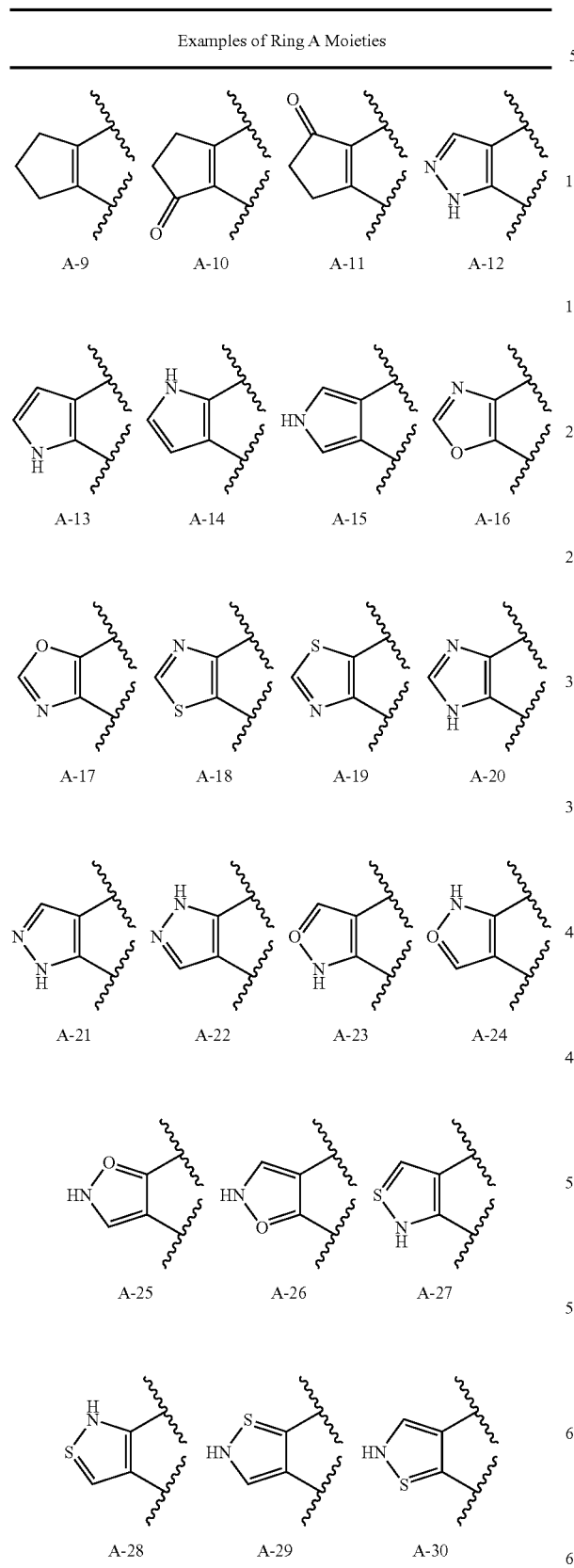
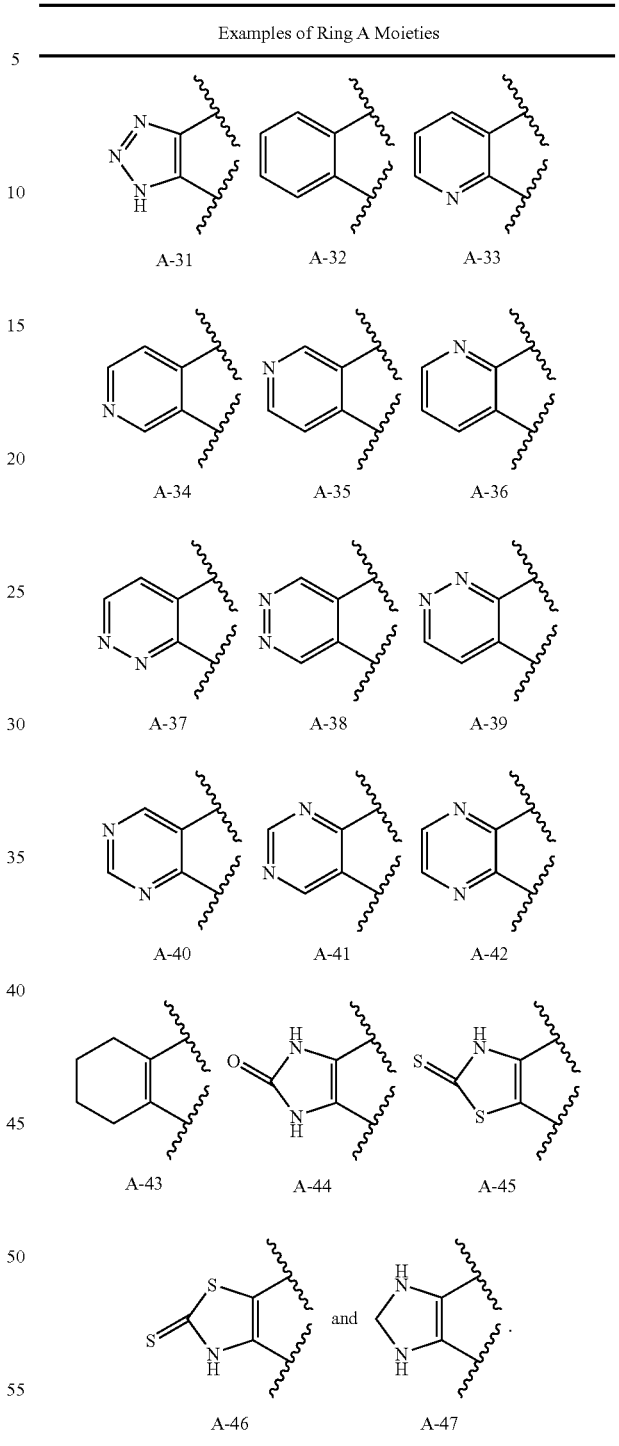

In some embodiments, two adjacent $R^b$ on one of the above Ring A moieties, taken together with the intervening ring atoms, form an optionally substituted fused 4- to 8-membered aromatic or nonaromatic fused ring, so that Ring A is a bicyclic moiety. Certain examples of such bicyclic moieties are shown in Table 2, any of which moieties optionally is substituted on any substitutable ring carbon atom and any substitutable ring nitrogen atom.

TABLE 2

Examples of Bicyclic Ring A Moieties

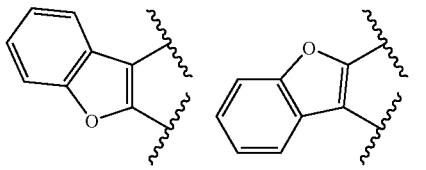

A-48   A-49

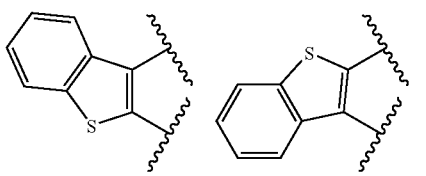

A-50   A-51

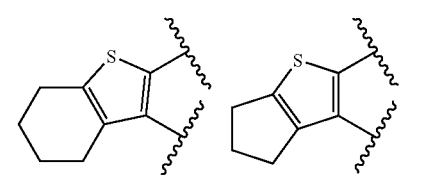

A-52   A-53

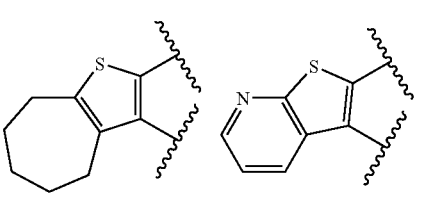

A-54   A-55

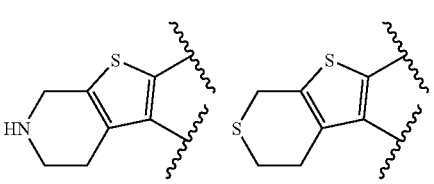

A-56   A-57

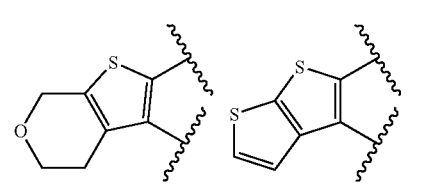

A-58   A-59

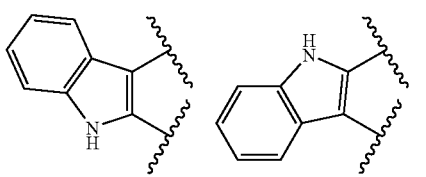

A-60   A-61

TABLE 2-continued

Examples of Bicyclic Ring A Moieties

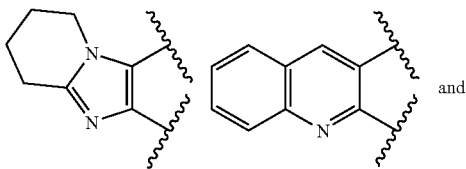

A-62   A-63   and

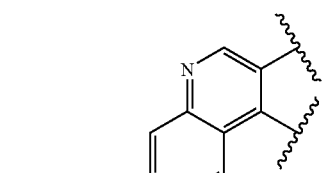

A-64

In some embodiments, the invention relates to a subgenus of formula (I) defined by formula (III):

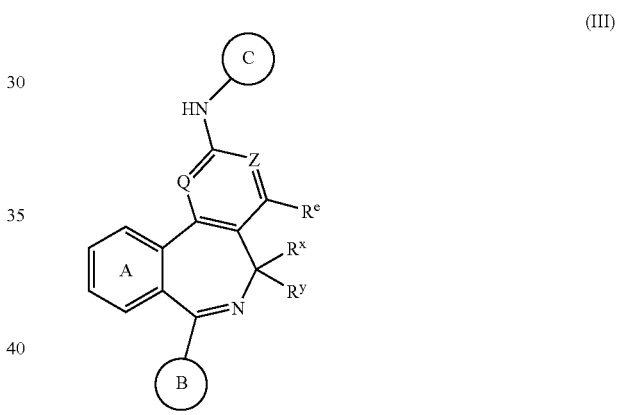

(III)

or a pharmaceutically acceptable salt thereof, wherein Ring A is substituted with 0-3 $R^b$. Rings B and C, and the variables $R^e$, $R^x$, and $R^y$ are as defined above for formula (I).

In certain such embodiments, Ring A has the formula A-i:

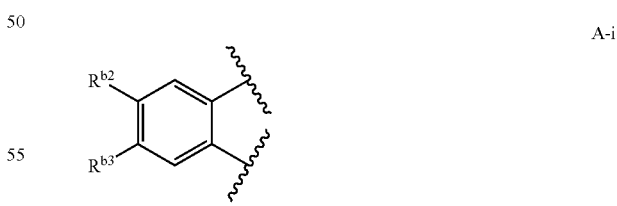

A-i wherein $R^{b2}$ and $R^{b3}$ are each independently hydrogen or $R^b$. In some embodiments, $R^{b2}$ and $R^{b3}$ are each independently selected from the group consisting of hydrogen, -halo, $C_{1-3}$ aliphatic, $C_{1-3}$ fluoroaliphatic, and $-OR^5$, where $R^5$ is hydrogen or $C_{1-3}$ aliphatic. In certain embodiments, $R^{b2}$ and $R^{b3}$ are each independently selected from the group consisting of hydrogen, chloro, fluoro, bromo, methyl, trifluoromethyl, and methoxy. In some other embodiments, $R^{b2}$ and $R^{b3}$, taken together with the intervening ring carbon atoms, form an optionally substituted fused 4- to 8-membered aromatic or non-aromatic ring having 0-3 ring heteroatoms selected from the group consisting of O, N, and S.

In the compounds of formulae (I)-(III) above, Ring B is a mono-, bi-, or tricyclic ring system. In some embodiments, the point of attachment for Ring B to the rest of the formula is on an aryl or heteroaryl ring of the Ring B moiety. In other embodiments, the point of attachment is on an heterocyclyl or cycloaliphatic ring. Preferably, Ring B is mono- or bicyclic.

Each substitutable saturated ring carbon atom in Ring B is unsubstituted or is substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^c$. Each substitutable unsaturated ring carbon atom in Ring B is unsubstituted or substituted with —$R^c$. Each substitutable ring nitrogen atom in Ring B is unsubstituted or is substituted with —$R^{9c}$, and one ring nitrogen atom in Ring B optionally is oxidized. Each $R^{9c}$ independently is —C(O)$R^5$, —C(O)N($R^4$)$_2$, —CO$_2R^6$, —SO$_2R^6$, —SO$_2$N($R^4$)$_2$, or a $C_{1-4}$ aliphatic optionally substituted with $R^3$ or $R^7$. Ring B may be unsubstituted or may be substituted on any one or more of its component rings, wherein the substituents may be the same or different. In some embodiments, Ring B is substituted with 0-2 independently selected $R^c$ and 0-3 independently selected $R^{2c}$ or $C_{1-6}$ aliphatic groups. The variables $R^3$, $R^4$, $R^5$, $R^6$, and $R^7$ are as defined above for Ring A, and $R^c$ and $R^{2c}$ are defined below.

Each $R^c$ independently is $R^{2c}$, an optionally substituted $C_{1-6}$ aliphatic, or an optionally substituted aryl, heteroaryl, or heterocyclyl group.

Each $R^{2c}$ independently is -halo, —NO$_2$, —CN, —C($R^5$)=C($R^5$)$_2$, —C($R^5$)=C($R^5$)($R^{10}$), —C≡C—$R^5$, —C≡C—$R^{10}$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —O—CO$_2R^5$, —OC(O)N($R^4$)$_2$, —O—C(O)$R^5$, —CO$_2R^5$, —C(O)—C(O)$R^5$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, —N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, or —P(O)(O$R^5$)$_2$.

In some embodiments, each $R^c$ independently is selected from the group consisting of $C_{1-6}$ aliphatic, $R^{2c}$, $R^{7c}$, -$T^1$-$R^{2c}$, and -$T^1$-$R^{7c}$, where $R^{2c}$ is as described above and $T^1$ and $R^{7c}$ are described below.

$T^1$ is a $C_{1-6}$ alkylene chain optionally substituted with $R^3$ or $R^{3b}$, wherein $T^1$ or a portion thereof optionally forms part of a 3- to 7-membered ring.

Each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl).

Each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring.

Each $R^{7c}$ independently is an optionally substituted aryl, heterocyclyl, or heteroaryl group.

In some embodiments, each $R^c$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain optionally substituted with fluoro. In some embodiments, each $R^c$ independently is selected from the group consisting of $C_{1-3}$ aliphatic, $R^{2c}$, and -$T^1$-$R^{2c}$, where $T^1$ is a $C_{1-3}$ alkylene chain optionally substituted with fluoro. In some such embodiments, each $R^{2c}$ independently is selected from the group consisting of -halo, —NO$_2$, —C($R^5$)=C($R^5$)$_2$, —C≡C—$R^5$, —O$R^5$, and —N($R^4$)$_2$.

In some embodiments, Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl, benzthiazolyl, benzoxazolyl, purinyl, quinolyl, isoquinolyl, cinnolinyl, phthalazinyl, quinazolinyl, quinoxalinyl, naphthyridinyl, and pteridinyl.

In some embodiments, Ring B is a monocyclic 5- or 6-membered aryl or heteroaryl ring, substituted with 0-2 independently selected $R^c$ and 0-2 independently selected $R^{2c}$ or $C_{1-6}$ aliphatic groups. In certain such embodiments, Ring B is a substituted or unsubstituted phenyl or pyridyl ring.

In some embodiments, Ring B is substituted with 0-2 substituents $R^c$. In some such embodiments, each $R^c$ independently is $C_{1-3}$ aliphatic or $R^{2c}$, and each $R^{2c}$ independently is selected from the group consisting of -halo, —NO$_2$, —C($R^5$)=C($R^5$)$_2$, —C≡C—$R^5$, —O$R^5$, and —N($R^4$)$_2$. In some embodiments, each $R^c$ independently is selected from the group consisting of -halo, $C_{1-3}$ aliphatic, $C_{1-3}$ haloaliphatic, and —O$R^5$, where $R^5$ is hydrogen or $C_{1-3}$ aliphatic. In certain preferred embodiments, Ring B is substituted with 0, 1, or 2 substituents, independently selected from the group consisting of chloro, fluoro, bromo, methyl, trifluoromethyl, and methoxy.

In some embodiments, Ring B has the formula B-i:

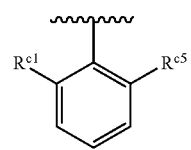

B-i wherein $R^{c1}$ and $R^{c5}$ are each independently hydrogen or $R^c$. In some embodiments, $R^{c1}$ and $R^{c5}$ are each independently selected from the group consisting of hydrogen, -halo, $C_{1-3}$ aliphatic, $C_{1-3}$ fluoroaliphatic, and —O$R^5$, where $R^5$ is hydrogen or $C_{1-3}$ aliphatic. In certain embodiments, $R^{c1}$ and $R^{c5}$ are each independently selected from the group consisting of hydrogen, chloro, fluoro, bromo, methyl, trifluoromethyl, and methoxy.

In some embodiments, the compound of formula (III) is defined by formula (IV):

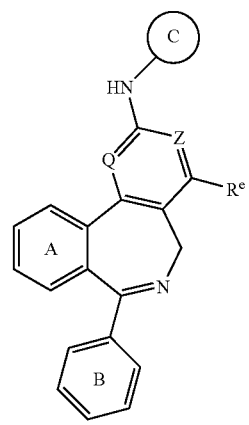

(IV)

wherein Ring A is substituted with 0-2 independently selected $R^b$, and Ring B is substituted with 0-2 independently selected $R^c$. In some embodiments, the compound of formula (IV) is characterized by at least one of the following features (a)-(c):

(a) each $R^b$ independently is selected from the group consisting of $C_{1-3}$ aliphatic, $R^{2b}$, $R^{7b}$, $-T^1-R^{2b}$, and $-T^1-R^{7b}$, where $T^1$ is a $C_{1-3}$ alkylene chain optionally substituted with fluoro, and each $R^{2b}$ independently is selected from the group consisting of -halo, $-NO_2$, $-C(R^5)=C(R^5)_2$, $-C\equiv C-R^5$, $-OR^5$, and $-N(R^4)_2$;

(b) each $R^c$ independently is selected from the group consisting of $C_{1-3}$ aliphatic, $R^{2c}$, $R^{7c}$, $-T^1-R^{2c}$, and $-T^1-R^{7c}$, where $T^1$ is a $C_{1-3}$ alkylene chain optionally substituted with fluoro, and each $R^{2c}$ independently is selected from the group consisting of -halo, $-NO_2$, $-C(R^5)=C(R^5)_2$, $-C\equiv C-R^5$, $-OR^5$, and $-N(R^4)_2$; and (c) $R^e$ is hydrogen.

Some embodiments of the invention relate to a subgenus of the compounds of formula (IV) defined by formula (V):

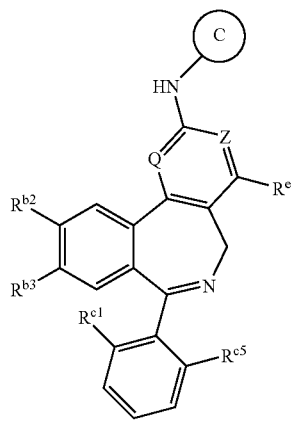

(V)

wherein: $R^{b2}$ and $R^{b3}$ are each independently hydrogen or $R^b$; $R^{c1}$ and $R^{c5}$ are each independently hydrogen or $R^c$; and Ring C, $R^b$, $R^c$, and $R^e$ have the values and preferred values described above for any preceding formula.

In some embodiments, each $R^b$ in formula (V) is selected from the group consisting of $C_{1-3}$ aliphatic, $C_{1-3}$ fluoroaliphatic, and $R^{2b}$; and each $R^c$ is selected from the group consisting of $C_{1-3}$ aliphatic, $C_{1-3}$ fluoroaliphatic, and $R^{2c}$. In certain such embodiments, $R^{2b}$ and $R^{2c}$ are each independently selected from the group consisting of -halo, $-NO_2$, $-C(R^5)=C(R^5)_2$, $-C\equiv C-R^5$, $-OR^5$, and $-N(R^4)_2$.

In some embodiments, the invention relates to a compound of formula (V), wherein $R^e$ is hydrogen; $R^{b2}$ and $R^{b3}$ are each independently selected from the group consisting of hydrogen, -halo, $C_{1-3}$ aliphatic, $C_{1-3}$ fluoroaliphatic, and $-OR^5$, where $R^5$ is hydrogen or $C_{1-3}$ aliphatic; and $R^{c1}$ and $R^{c5}$ are each independently selected from the group consisting of hydrogen, -halo, $C_{1-3}$ aliphatic, $C_{1-3}$ fluoroaliphatic, and $-OR^5$, where $R^5$ is hydrogen or $C_{1-3}$ aliphatic. In some embodiments, $R^{b3}$ and $R^{c1}$ are each independently selected from the group consisting of -halo, $C_{1-3}$ aliphatic, $C_{1-3}$ fluoroaliphatic, and $-OR^5$, where $R^5$ hydrogen or $C_{1-3}$ aliphatic. In certain such embodiments, $R^{b2}$ is hydrogen, $R^{c5}$ is selected from the group consisting of hydrogen, -halo, $C_{1-3}$ aliphatic, $C_{1-3}$ fluoroaliphatic, and $-OR^5$, and $R^{b3}$ and $R^{c1}$ are each independently selected from the group consisting of -halo, $C_{1-3}$ aliphatic, $C_{1-3}$ fluoroaliphatic, and $-OR^5$, where $R^5$ hydrogen or $C_{1-3}$ aliphatic. In certain embodiments, $R^{b2}$ is hydrogen, $R^{c2}$ is hydrogen, chloro, fluoro, bromo, methyl, trifluoromethyl, or methoxy, and $R^{b3}$ and $R^{c1}$ are each independently chloro, fluoro, bromo, methyl, trifluoromethyl, or methoxy.

In the compounds of formulae (I)-(V) above, Ring C is a substituted or unsubstituted mono-, bi-, or tricyclic ring system. In some embodiments, the point of attachment for Ring C to the rest of the formula is on an aryl or heteroaryl ring of the Ring C moiety. In other embodiments, the point of attachment is on a heterocyclyl or cycloaliphatic ring. Preferably, Ring C is mono-, or bicyclic.

Each substitutable saturated ring carbon atom in Ring C is unsubstituted or is substituted with $=O$, $=S$, $=C(R^5)_2$, $=N-N(R^4)_2$, $=N-OR^5$, $=N-NHC(O)R^5$, $=N-NHCO_2R^6$, $=N-NHSO_2R^6$, $=N-R^5$ or $-R^d$. Each substitutable unsaturated ring carbon atom in Ring C is unsubstituted or substituted with $-R^d$. Each substitutable ring nitrogen atom in Ring C is unsubstituted or is substituted with $-R^{9d}$, and one ring nitrogen atom in Ring C optionally is oxidized. Each $R^{9d}$ independently is $-C(O)R^5$, $-C(O)N(R^4)_2$, $-CO_2R^6$, $-SO_2R^6$, $-SO_2N(R^4)_2$, or a $C_{1-4}$ aliphatic optionally substituted with $R^3$ or $R^7$. Ring C may be unsubstituted or may be substituted on any one or more of its component rings, wherein the substituents may be the same or different. In some embodiments, Ring C is substituted with 0-2 independently selected $R^d$ and 0-3 independently selected $R^{2d}$ or $C_{1-6}$ aliphatic groups. The variables $R^3$, $R^4$, $R^5$, $R^6$, and $R^7$ are as described above for Rings A and B. The variables $R^d$ and $R^{2d}$ are described below.

Each $R^d$ independently is $R^{2d}$, an optionally substituted aliphatic, or an optionally substituted aryl, heteroaryl, or heterocyclyl group.

Each $R^{2d}$ independently is -halo, $-NO_2$, $-CN$, $-C(R^5)=C(R^5)_2$, $-C(R^5)=C(R^5)_2(R^{10})$, $-C\equiv C-R^5$, $-C\equiv C-R^{10}$, $-OR^5$, $-SR^6$, $-S(O)R^6$, $-SO_2R^6$, $-SO_2N(R^4)_2$, $-N(R^4)C(O)R^5$, $-NR^4C(O)N(R^4)_2$, $-NR^4CO_2R^6$, $-O-CO_2R^5$, $-OC(O)N(R^4)_2$, $-O-C(O)R^5$, $-CO_2R^5$, $-C(O)-C(O)R^5$, $-C(O)R^5$, $-C(O)N(R^4)_2$, $-C(=NR^4)-N(R^4)_2$, $-C(=NR^4)-OR^5$, $-N(R^4)-N(R^4)_2$, $-N(R^4)C(=NR^4)-N(R^4)_2$, $-N(R^4)SO_2R^6$, $-N(R^4)SO_2N(R^4)_2$, $-P(O)(R^5)_2$, or $-P(O)(OR^5)_2$. Additionally, $R^{2d}$ can be $-SO_3R^5$, $-C(O)N(R^4)C(=NR^4)-N(R^4)_2$ or $-N(R^4)C(=NR^4)-N(R^4)-C(O)R^5$.

In some embodiments, each $R^d$ independently is selected from the group consisting of $C_{1-6}$ aliphatic, $R^{2d}$, $R^{7d}$, $-T^2-R^{2d}$, $-T^2-R^{7d}$, $-V-T^3-R^{2d}$, and $-V-T^3-R^{7d}$, wherein $R^{2d}$ is as described above, and $T^2$, $T^3$, V, and $R^{7d}$ are described below.

$T^2$ is a $C_{1-6}$ alkylene chain optionally substituted with $R^3$ or $R^{3b}$, wherein the alkylene chain optionally is interrupted by $-C(R^5)=C(R^5)-$, $-C\equiv C-$, $-O-$, $-S-$, $-S(O)-$, $-S(O)_2-$, $-SO_2N(R^4)-$, $-N(R^4)-$, $-N(R^4)C(O)-$, $-NR^4C(O)N(R^4)-$, $-N(R^4)CO_2-$, $-C(O)N(R^4)-$, $-C(O)-$, $-C(O)-C(O)-$, $-CO_2-$, $-OC(O)-$, $-OC(O)O-$, $-OC(O)N(R^4)-$, $-N(R^4)-N(R^4)-$, $-N(R^4)SO_2-$, or $-SO_2N(R^4)-$, and wherein $T^2$ or a portion thereof optionally forms part of a 3-7 membered ring.

$T^3$ is a $C_{1-6}$ alkylene chain optionally substituted with $R^3$ or $R^{3b}$, wherein the alkylene chain optionally is interrupted by $-C(R^5)=C(R^5)-$, $-C\equiv C-$, $-O-$, $-S-$, $-S(O)-$, $-S(O)_2-$, $-SO_2N(R^4)-$, $-N(R^4)-$, $-N(R^4)C(O)-$, $-NR^4C(O)N(R^4)-$, $-N(R^4)CO_2-$, $-C(O)N(R^4)-$, $-C(O)-$, $-C(O)-C(O)-$, $-CO_2-$, $-OC(O)-$, $-OC(O)O-$, $-OC(O)N(R^4)-$, $-N(R^4)-N(R^4)-$, $-N(R^4)SO_2-$, or $-SO_2N(R^4)-$, and wherein $T^3$ or a portion thereof optionally forms part of a 3-7 membered ring.

V is —C(R⁵)=C(R⁵)—, —C≡C—, —O—, —S—, —S(O)—, —S(O)₂—, —SO₂N(R⁴)—, —N(R⁴)—, —N(R⁴)C(O)—, —NR⁴C(O)N(R⁴)—, —N(R⁴)CO₂—, —C(O)N(R⁴)—, —C(O)—, —C(O)—C(O)—, —CO₂—, —OC(O)—, —OC(O)O—, —OC(O)N(R⁴)—, —C(NR⁴)=N—, —C(OR⁵)=N—, —N(R⁴)—N(R⁴)—, —N(R⁴)SO₂—, —N(R⁴)SO₂N(R⁴)—, —P(O)(R⁵)—, —P(O)(OR⁵)—O—, —P(O)—O—, or —P(O)(NR⁵)—N(R⁵)—.

Each R³ᵇ independently is a C₁₋₃ aliphatic optionally substituted with R³ or R⁷, or two substituents R³ᵇ on the same carbon atom, taken together with the carbon atom to which they are attached, form a 3- to 6-membered carbocyclic ring.

Each R⁷ᵈ independently is an optionally substituted aryl, heterocyclyl, or heteroaryl group.

In some embodiments, each R²ᵈ independently is selected from the group consisting of -halo, —OR⁵, —N(R⁴)₂, —N(R⁴)C(O)—, —CO₂R⁵, —C(O)N(R⁴)₂, and —SO₂N(R₄)₂. In some other embodiments, each R²ᵈ independently is -halo, —OR⁵, —N(R⁴)₂, —N(R⁴)C(O)R⁵, —CO₂R⁵, —C(O)N(R⁴)₂, and —SO₂N(R₄)₂, —C(O)N(R⁴)C(=NR⁴)—N(R⁴)₂ or —N(R⁴)C(=NR⁴)—N(R⁴)—C(O)R⁵.

In some embodiments, T² is a C₁₋₆ alkylene chain, which optionally is substituted with one or two substituents R³ᵇ independently selected from the group consisting of -halo, —C₁₋₃ aliphatic, —OH, and —O(C₁₋₃ aliphatic), or two substituents R³ᵇ on the same carbon atom, taken together with the carbon atom to which they are attached, form a 3- to 6-membered carbocyclic ring. In some embodiments, T² optionally is interrupted by —C(R⁵)=C(R⁵)—, —C≡C—, —O—, —C(O)—, —C(O)N(R⁴)—, —N(R⁴)C(O)— or —N(R⁴)—.

In some embodiments, V is —C(R⁵)=C(R⁵)—, —C≡C—, —O—, —N(R⁴)—, —C(O)—, —N(R⁴)C(O)—, or —C(O)N(R⁴)—. In some embodiments, T³ is a C₁₋₄ alkylene chain, which optionally is substituted with one or two R³ᵇ independently selected from the group consisting of -halo, —C₁₋₃ aliphatic, —OH, and —O(C₁₋₃ aliphatic), or two substituents R³ᵇ on the same carbon atom, taken together with the carbon atom to which they are attached, form a 3- to 6-membered carbocyclic ring. In some embodiments, T³ is a C₁₋₄ alkylene chain, which optionally is interrupted by —C(R⁵)=C(R⁵)—, —C≡C—, —O—, —C(O)—, —C(O)N(R⁴)—, —N(R⁴)C(O)— or —N(R⁴)—.

In some embodiments, each Rᵈ independently is selected from the group consisting of C₁₋₃ aliphatic, R²ᵈ, R⁷ᵈ, -T²-R²ᵈ, -T²-R⁷ᵈ, —V-T³-R²ᵈ, and —V-T³-R⁷ᵈ, where R²ᵈ is selected from the group consisting of -halo, —OR⁵, —N(R⁴)₂, —N(R⁴)C(O)—, —CO₂R⁵, —C(O)N(R⁴)₂, and —SO₂N(R₄)₂. Additionally, R²ᵈ can be —SO₃R⁵, —C(O)N(R⁴)C(=NR⁴)—N(R⁴)₂ or —N(R⁴)C(=NR⁴)—N(R⁴)—C(O)R⁵.

In some embodiments, Ring C is substituted with at least one R⁷ᵈ selected from the group consisting of:

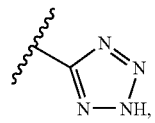 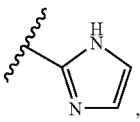 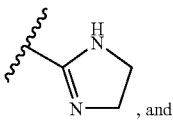, and

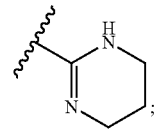;

any of which groups optionally is substituted on any substitutable ring carbon or ring nitrogen atom.

In some embodiments, Ring C is substituted with at least one -T²-R²ᵈ or -T²-R⁷ᵈ, where:

T² is a C₁₋₆ alkylene chain, wherein T² optionally is substituted with one or two substituents R³ᵇ independently selected from the group consisting of -halo, —C₁₋₃ aliphatic, —OH, and —O(C₁₋₃ aliphatic), or two substituents R³ᵇ on the same carbon atom, taken together with the carbon atom to which they are attached, form a 3- to 6-membered carbocyclic ring, and wherein T² optionally is interrupted by —C(R⁵)=C(R⁵)—, —C≡C—, —O—, —C(O)—, —NR⁴C(O)R⁵, —N(R⁴)C(O)— or —N(R⁴)—; and R²ᵈ is selected from the group consisting of -halo, —OR⁵, —N(R⁴)₂, —N(R⁴)C(O)—, —CO₂R⁵, —C(O)N(R⁴)₂, —SO₂N(R₄)₂, —C(O)N(R⁴)C(=NR⁴)—N(R⁴)₂ and —N(R⁴)C(=NR⁴)—N(R⁴)—C(O)R⁵.

In certain such embodiments, Ring C is substituted with one -T²-R²ᵈ or -T²-R⁷ᵈ, and optionally one other substituent selected from the group consisting of hydrogen, -halo, C₁₋₃ aliphatic, and —OR⁵, where R⁵ is hydrogen or C₁₋₃ aliphatic. In some embodiments, T² is a C₁₋₆ alkylene chain, which optionally is interrupted by —C(O)N(R⁴)— or —N(R⁴)C(O)—.

In some embodiments, Ring C is substituted with at least one —V-T³-R²ᵈ or —V-T³-R⁷ᵈ, where:

V is —N(R⁴)—, —O—, —C(O)N(R⁴)—, —C(O)—, or —C≡C—;

T³ is a C₁₋₄ alkylene chain, which is optionally substituted by one or two substituents R³ᵇ independently selected from the group consisting of -halo, —C₁₋₃ aliphatic, —OH, and —O(C₁₋₃ aliphatic), or two substituents R³ᵇ on the same carbon atom, taken together with the carbon atom to which they are attached, form a 3- to 6-membered carbocyclic ring; and R²ᵈ is selected from the group consisting of -halo, —OR⁵, —N(R⁴)₂, —NR⁴C(O)R⁵, —CO₂R⁵, —C(O)N(R⁴)₂, and —SO₂N(R₄)₂.

In certain such embodiments, Ring C is substituted with one —V-T³-R²ᵈ or —V-T³-R⁷ᵈ, and optionally one other substituent selected from the group consisting of hydrogen, -halo, C₁₋₃ aliphatic, and —OR⁵, where R⁵ is hydrogen or C₁₋₃ aliphatic.

In some embodiments, Ring C is substituted with —V-T³-R²ᵈ, where V is —C(O)N(R⁴)—, T³ is a C₂₋₄ alkylene chain, and R²ᵈ is —N(R⁴)₂. Each R⁴ independently is hydrogen or C₁₋₃ aliphatic, or —N(R⁴)₂ is an optionally substituted 5- to 6-membered heteroaryl or 4- to 8-membered heterocyclyl ring having, in addition to the nitrogen, 0-2 ring heteroatoms selected from N, O, and S. In certain such embodiments, —N(R⁴)₂ is an optionally substituted heterocyclyl selected from the group consisting of piperidinyl, piperazinyl, and morpholinyl. In certain other such embodiments, —N(R⁴)₂ is an optionally substituted heterocyclyl selected from pyrrolidinyl and azetidinyl.

In other embodiments, Ring C is substituted with —V-T³-R⁷ᵈ, where V is —C(O)N(R⁴)—, T³ is a C₂₋₄ alkylene chain, and R⁷ᵈ is an optionally substituted 4- to 8-membered heterocyclyl or an optionally substituted 5- to 6-membered heteroaryl. In certain such embodiments, $R^{7d}$ is selected from the group consisting of pyridyl, pyridazinyl, pyrimidinyl, pyrazinyl, pyrrolyl, oxazolyl, imidazolyl, and pyrazolyl. In certain other such embodiments, $R^{7d}$ is a 6- to 8-membered bicyclic heterocyclyl.

In some embodiments, Ring C is substituted with one or two substituents independently selected from the group consisting of $C_{1-3}$ aliphatic, -halo, —$OR^5$, —$CO_2R^5$, —$C(O)N(R^4)_2$, and —$SO_2N(R^4)_2$. Additional selections possible for Ring C substituents in these embodiments include —$C(=NR^4)N(R^4)_2$, —$NR^4C(O)R^5$, —$C(O)N(R^4)C(=NR^4)$—$N(R^4)_2$ and —$N(R^4)C(=NR^4)$—$N(R^4)$—$C(O)R^5$. In some embodiments, Ring C is substituted with at least one substituent selected from the group consisting of —$CO_2R^5$, —$C(O)N(R^4)_2$, —$C(=NR^4)N(R^4)_2$, —$C(O)N(R^4)C(=NR^4)$—$N(R^4)_2$, —$N(R^4)C(=NR^4)$—$N(R^4)$—$C(O)R^5$, and —$NR^4C(O)R^5$. In certain embodiments, Ring C is substituted with at least one —$CO_2R^5$, where $R^5$ is hydrogen or $C_{1-6}$ aliphatic.

In some embodiments, Ring C is substituted with at least one —$C(O)$—$N(R^4)_2$, —$C(=NR^4)N(R^4)_2$, or —$NR^4C(O)R^5$, where —$N(R^4)_2$ is an optionally substituted 4- to 8-membered heterocyclyl ring having, in addition to the nitrogen atom, 0-2 ring heteroatoms selected from N, O, and S, and $R^5$ is an optionally substituted 4 to 8-membered nitrogen-containing heterocyclyl ring. In some such embodiments, —$N(R^4)_2$ is an optionally substituted heterocyclyl selected from the group consisting of piperidinyl, piperazinyl, morpholinyl, pyrrolidinyl, and azetidinyl. In some other such embodiments, —$N(R^4)_2$ is a bridged or spiro bicyclic heterocyclyl.

In certain embodiments, Ring C is substituted with at least one substituent having the formula D-i:

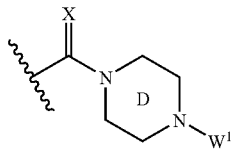

D-i wherein:
Ring D optionally is substituted on one or two ring carbon atoms;
X is O or NH;
$W^1$ is hydrogen, —$C(O)R^5$, —$C(O)N(R^4)_2$, —$CO_2R^6$, —$SO_2R^6$, —$SO_2N(R^4)_2$, or an optionally substituted aliphatic, aryl, heteroaryl, or heterocyclyl group.

In some embodiments, Ring D in formula D-i is substituted with one or two substituents selected from the group consisting of $C_{1-3}$ aliphatic, —$CO_2R^5$, —$C(O)N(R^4)_2$, and -$T^5$-$R^m$, where $T^5$ is a $C_{1-3}$ alkylene chain and $R^m$ is —$OR^5$, —$N(R^4)_2$, —$CO_2R^5$, or —$C(O)N(R^4)_2$. In some such embodiments, Ring D in formula D-1 is substituted with one or two substituents selected from the group consisting of $C_{1-3}$ aliphatic, —$CO_2H$, —$CO_2(C_{1-3}$ alkyl), —$C(O)N(C_{1-3}$ alkyl)$_2$, —$C(O)NH(C_{1-3}$ alkyl), —$C(O)NH_2$, —$(C_{1-3}$ alkyl)-OH, —$(C_{1-3}$ alkylene)-O$(C_{1-3}$ alkyl), —$(C_{1-3}$ alkylene)-NH$_2$, —$(C_{1-3}$ alkylene)-NH$(C_{1-3}$ alkyl), —$(C_{1-3}$ alkylene)-N$(C_{1-3}$ alkyl)$_2$, —$(C_{1-3}$ alkylene)-CO$_2$H, —$(C_{1-3}$ alkylene)-CO$_2(C_{1-3}$ alkyl), —$(C_{1-3}$ alkylene)-C(O)NH$_2$, —$(C_{1-3}$ alkylene)-C(O)NH$(C_{1-3}$ alkyl), and —$(C_{1-3}$ alkylene)-C(O)N$(C_{1-3}$ alkyl)$_2$.

In certain other embodiments, Ring C is substituted with at least one substituent having one of the formulae D-ii to D-v below:

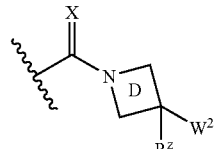

D-ii

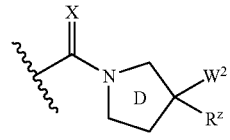

D-iii

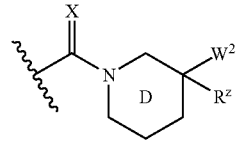

D-iv

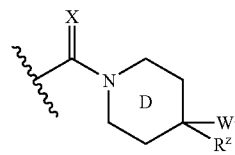

D-v wherein:
Ring D optionally is substituted on one or two substitutable ring carbon atoms;
X is O or NH;
$W^2$ is $R''$ or -$T^6$-$R''$;
$T^6$ is a $C_{1-3}$ alkylene chain optionally substituted with $R^3$ or $R^{3b}$; and
$R''$ is —$N(R^4)_2$ or —$C(O)N(R^4)_2$; and
$R^z$ is hydrogen, —$CO_2R^5$, $C(O)N(R^4)_2$, —$C(O)R^5$, or a $C_{1-3}$ aliphatic optionally substituted with $R^3$ or $R^7$; or $R^z$ and $W^2$, taken together with the carbon atom to which they are attached, form a 4- to 7-membered cycloaliphatic or heterocyclyl ring.

In some embodiments, Ring D in formulae D-ii to D-v is substituted with one or two substituents selected from the group consisting of $C_{1-3}$ aliphatic, —$CO_2R^5$, —$C(O)N(R^4)_2$, —$OR^5$, —$N(R^4)_2$, and -$T^5$-$R^m$, where $T^5$ is a $C_{1-3}$ alkylene chain and $R^m$ is —$OR^5$, —$N(R^4)_2$, —$CO_2R^5$, or —$C(O)N(R^4)_2$.

In certain embodiments, at least one substituent on Ring C is selected from the group consisting of:

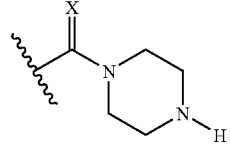

D-1

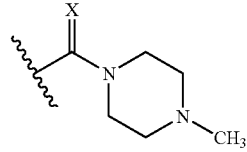

D-2

-continued
D-3 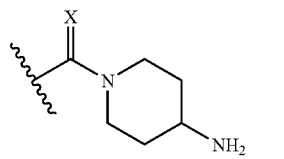
D-4 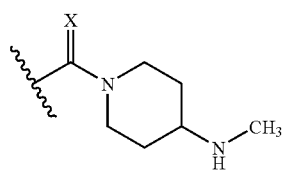
D-5 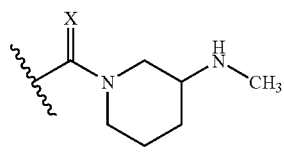
D-6 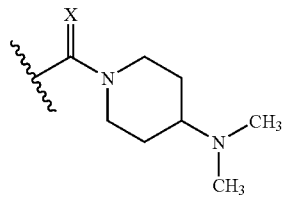
D-7 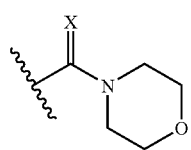
D-8 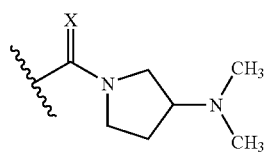
D-9 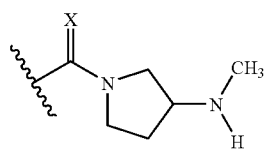
D-10 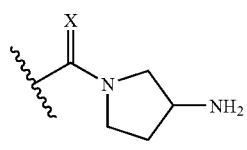
D-11 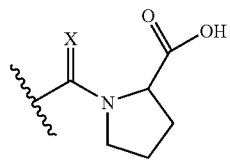
-continued
D-12 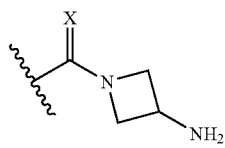
D-13 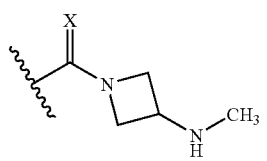
D-14 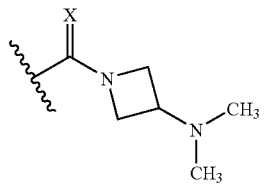
D-15 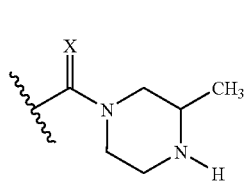
D-16 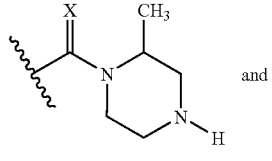
and
D-17 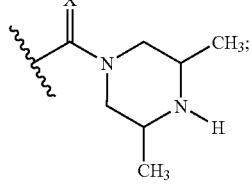
where X is O or NH.
In certain other embodiments, at least one substituent on Ring C is selected from the group consisting of:
D-18 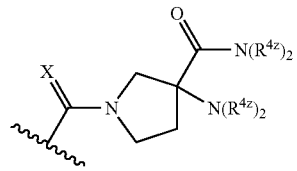
D-19 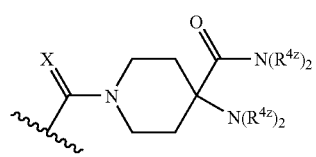

-continued
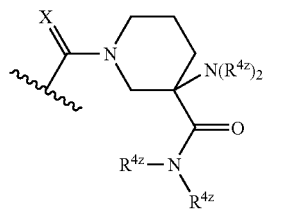 D-20
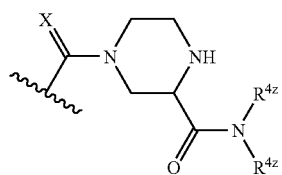 D-21
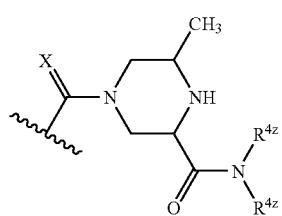 D-22
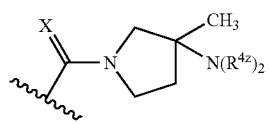 D-23
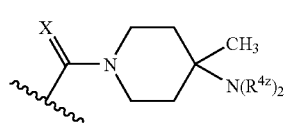 D-24
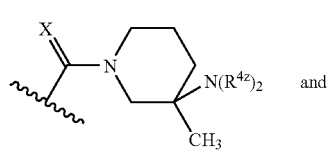 D-25 and
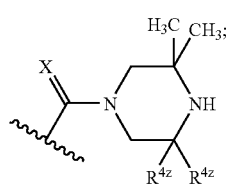 D-26
where X is O or NH, and each $R^{4a}$ independently is hydrogen or —CH$_3$.
In certain other embodiments, at least one substituent on Ring C is selected from the group consisting of:
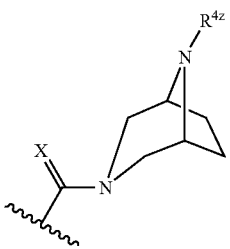 D-27
-continued
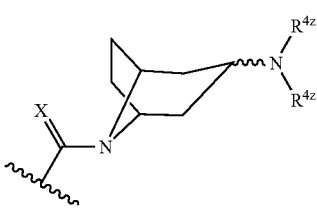 D-28
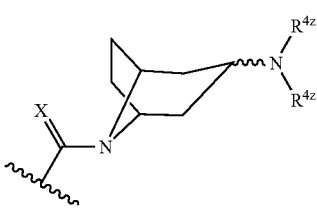 D-29
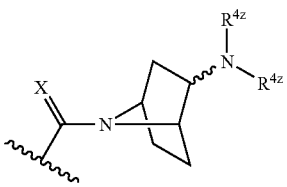 D-30
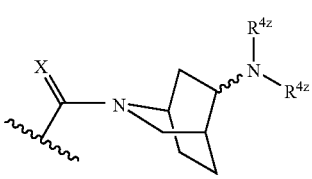 D-31
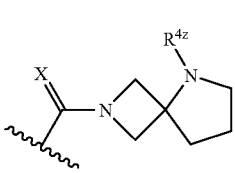 D-32
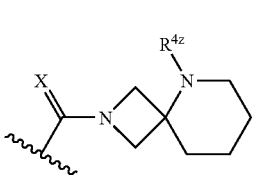 D-33
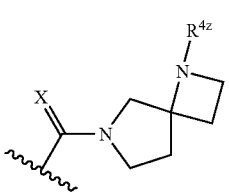 D-34
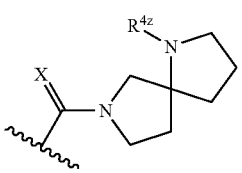 D-35

-continued

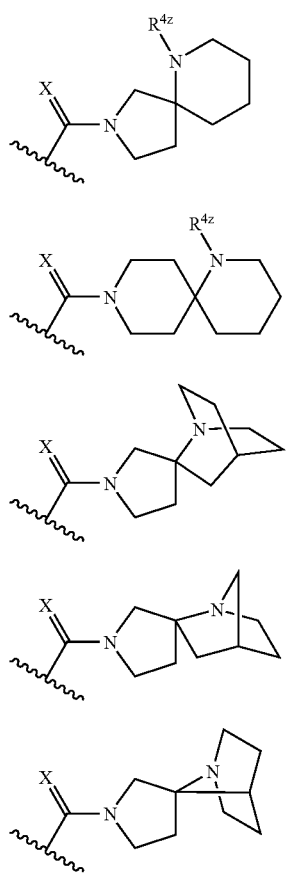

D-36

D-37

D-38

D-39

D-40 where X is O or NH, and each $R^{4e}$ independently is hydrogen or —CH$_3$.

In some embodiments, Ring C is substituted with at least one —C(O)N(R$^4$)$_2$ or —C(=NH)N(R$^4$)$_2$, where one R$^4$ is hydrogen or C$_{1-3}$ alkyl, and the other R$^4$ is an optionally substituted heterocyclyl or heterocyclylalkyl. In some such embodiments, Ring C is substituted with at least one substituent selected from the group consisting of:

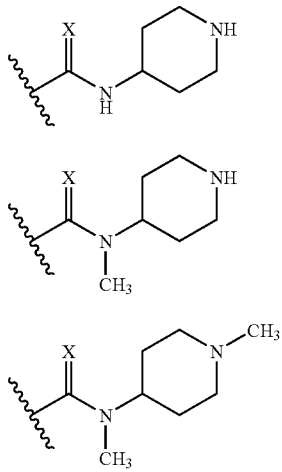

D-41

D-42

D-43

-continued

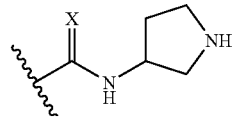

D-44

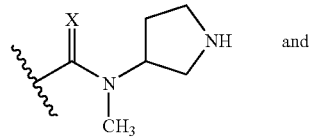

D-45

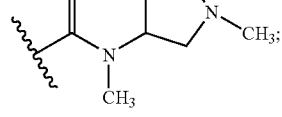

D-46 where X is O or NH.

In some other such embodiments, Ring C is substituted with at least one substituent selected from the group consisting of:

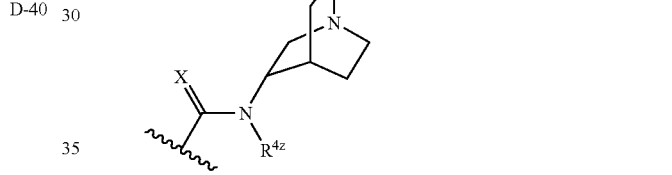

D-47

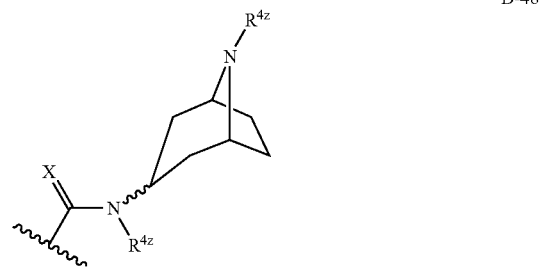

D-48

D-49

D-50 and

-continued

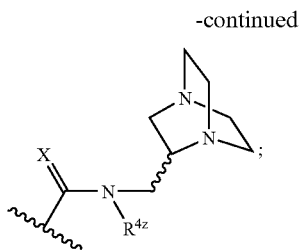

D-51 where X is O or NH, and each $R^{4z}$ independently is H or $CH_3$.

In some embodiments, Ring C is a bicyclic aryl group, which is substituted with 0-2 independently selected $R^d$ and 0-3 independently selected $R^{2d}$ or $C_{1-6}$ aliphatic groups. In some such embodiments, Ring C is a phenyl ring fused to a 5- or 6-membered carbocyclic, heteroaryl, or heterocyclyl ring, wherein each ring independently is substituted or unsubstituted. In certain such embodiments, Ring C is an optionally substituted benzodioxanyl or benzodioxolyl ring. In certain other such embodiments, Ring C is an optionally substituted benzimidazolyl, benzthiazolyl, benzoxazolyl, or phthalimidyl ring, wherein Ring C is attached to the rest of formula (I) or (II) at the benzo ring of the bicyclic Ring C moiety.

In some other embodiments, Ring C is a monocyclic 5- or 6-membered aryl or heteroaryl ring, which is substituted with 0-2 independently selected substituents $R^d$ and 0-2 independently selected $R^{2d}$ or $C_{1-6}$ aliphatic groups. In some such embodiments, Ring C is an optionally substituted heteroaryl ring selected from the group consisting of pyridyl, pyrimidinyl, pyrazinyl, pyridazinyl, imidazolyl, pyrazolyl, and oxazolyl. In some other embodiments, Ring C is a substituted or unsubstituted phenyl ring. In some embodiments, Ring C is a monocyclic 5- or 6-membered aryl or heteroaryl ring, which is substituted with 0, 1, or 2 substituents $R^d$, as defined above.

In yet other embodiments, Ring C is a monocyclic 5- or 6-membered heterocyclyl or cycloaliphatic ring, which is substituted with 0-2 independently selected substituents $R^d$ and 0-2 independently selected $R^{2d}$ or $C_{1-6}$ aliphatic groups.

Some embodiments of the invention relate to a subgenus of the compounds of formula (I) defined by formula (VI):

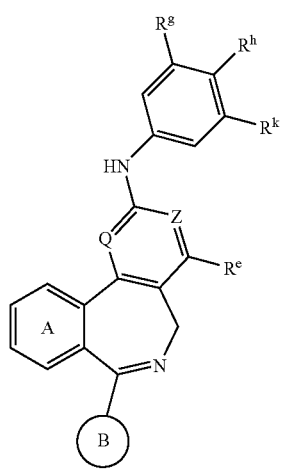

(VI)

wherein:

$R^g$ is selected from the group consisting of hydrogen, $C_{1-6}$ aliphatic, and $R^{2d}$;

$R^h$ and $R^k$ are each independently hydrogen or $R^d$; and

Rings A and B, and the variables Q, Z, and $R^e$ have the values and preferred values described above for formulae (I)-(V).

In some such embodiments, the invention relates to a compound of formula (VI), wherein:
each $R^4$ in $R^d$ or $R^{2d}$ is hydrogen, $C_{1-3}$ alkyl, or a 5- or 6-membered aryl or heteroaryl ring; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S; and
each $R^5$ in $R^d$ or $R^{2d}$ is hydrogen, $C_{1-3}$ alkyl, or a 5- or 6-membered aryl or heteroaryl ring.

In some such embodiments, two $R^4$ on the same nitrogen atom in $R^d$ or $R^{2d}$, taken together with the nitrogen atom, form an optionally substituted piperidinyl, piperazinyl, or morpholinyl ring.

In some embodiments, the invention relates to a compound of formula (VI) wherein:
Ring A is substituted with 0-2 $R^b$, where each $R^b$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain;
Ring B is a monocyclic 5- or 6-membered aryl or heteroaryl ring, which is substituted with 0-2 independently selected $R^c$, where each $R^c$ independently is selected from the group consisting of $C_{1-3}$ aliphatic, $R^{2c}$, $R^{7c}$, -$T^1$-$R^{2c}$, and -$T^1$-$R^{7c}$, where $T^1$ is a $C_{1-3}$ alkylene chain; and
$R^e$ is hydrogen.

In some such embodiments, each $R^b$ independently is selected from the group consisting of $C_{1-3}$ aliphatic, $R^{2b}$, and -$T^1$-$R^{2b}$, and each $R^c$ independently is selected from the group consisting of $C_{1-3}$ aliphatic, $R^{2c}$, and -$T^1$-$R^{2c}$. In some embodiments, each $R^{2b}$ independently is selected from the group consisting of -halo, —$NO_2$, —$C(R^5)$=$C(R^5)_2$, —C≡C—$R^5$, —$OR^5$, and —$N(R^4)_2$, and each $R^{2c}$ independently is selected from the group consisting of -halo, —$NO_2$, —$C(R^5)$=$C(R^5)_2$, —C≡C—R, —$OR^5$, and —$N(R^4)_2$.

In some embodiments, the invention is directed to the compound of formula (VI), wherein one of $R^h$ and $R^k$ is $R^{7d}$. In some such embodiments, $R^g$ is hydrogen, and $R^{7d}$ is tetrazolyl.

In some embodiments, the invention relates to a compound of formula (VI), wherein $R^g$ is hydrogen, one of $R^h$ and $R^k$ has the formula -$T^2$-$R^{2d}$ or -$T^2$-$R^{7d}$, and the other of $R^h$ and $R^k$ is selected from the group consisting of hydrogen, -halo, $C_{1-3}$ aliphatic, and —$OR^5$, where $R^5$ is hydrogen or $C_{1-3}$ aliphatic. In some embodiments, $T^2$ is a $C_{1-6}$ alkylene chain, which optionally is interrupted by —C(O)N($R^4$)— or —N($R^4$)C(O)—.

In some embodiments, the invention is directed to a compound of formula (VI) wherein $R^g$ is hydrogen, one of $R^h$ and $R^k$ has the formula —V-$T^3$-$R^{2d}$, and the other of $R^h$ and $R^k$ is selected from the group consisting of hydrogen, -halo, $C_{1-3}$ aliphatic, and —$OR^5$, where $R^5$ is hydrogen or $C_{1-3}$ aliphatic. In some such embodiments, V is —C(O)N($R^4$)—, $T^3$ is a $C_{2-4}$ alkylene chain, and $R^{2d}$ is —$N(R^4)_2$, where each $R^4$ independently is hydrogen or $C_{1-3}$ aliphatic, or —$N(R^4)_2$ is an optionally substituted 5- to 6-membered heteroaryl or 4- to 8-membered heterocyclyl ring having, in addition to the nitrogen, 0-2 ring heteroatoms selected from N, O, and S. In certain such embodiments, —$N(R^4)_2$ is an optionally substituted heterocyclyl selected from the group consisting of piperidinyl, piperazinyl, and morpholinyl. In certain other such embodiments, —N(R⁴)₂ is an optionally substituted heterocyclyl selected from pyrrolidinyl and azetidinyl.

In some other embodiments, the invention relates to a compound of formula (VI), wherein $R^g$ is hydrogen, one of $R^h$ and $R^k$ has the formula —V-T³-R⁷ᵈ, and the other of $R^h$ and $R^k$ is selected from the group consisting of hydrogen, -halo, $C_{1-3}$ aliphatic, and —OR⁵, where R⁵ is hydrogen or $C_{1-3}$ aliphatic. In certain such embodiments, V is —C(O)N(R⁴)—, T³ is a $C_{2-4}$ alkylene chain, and R⁷ᵈ is an optionally substituted 4- to 8-membered heterocyclyl or an optionally substituted 5- to 6-membered heteroaryl. In certain such embodiments, R⁷ᵈ is an optionally substituted heteroaryl selected from the group consisting of pyridyl, pyridazinyl, pyrimidinyl, pyrazinyl, pyrrolyl, oxazolyl, imidazolyl, and pyrazolyl. In certain other such embodiments, R⁷ᵈ is a 6 to 8-membered bridged bicyclic heterocyclyl.

In some embodiments, the invention is directed to a compound of formula (VI) wherein $R^g$ is hydrogen, and at least one of $R^h$ and $R^k$ is selected from the group consisting of —CO₂R⁵, —C(O)N(R⁴)₂, —C(=NR⁴)N(R⁴)₂, —C(O)N(R⁴)C(=NR⁴)—N(R⁴)₂, —N(R⁴)C(=NR⁴)—N(R⁴)—C(O)R⁵, or —NR⁴C(O)R⁵. In some such embodiments, at least one of $R^h$ and $R^k$ is —CO₂R⁵, where R⁵ is hydrogen or $C_{1-6}$ aliphatic. In some embodiments, $R^g$ is hydrogen, $R^h$ is —CO₂R⁵, and $R^k$ is selected from the group consisting of hydrogen, halo, $C_{1-3}$ aliphatic, and —OR⁵. In some other embodiments, $R^g$ and $R^k$ are each hydrogen, and $R^h$ is —CO₂R⁵.

In some embodiments, $R^g$ is hydrogen, and one of $R^h$ and $R^k$ is —C(O)—N(R⁴)₂ or —C(=NR⁴)N(R⁴)₂, where —N(R⁴)₂ is an optionally substituted heterocyclyl selected from the group consisting of piperidinyl, piperazinyl, morpholinyl, pyrrolidinyl, and azetidinyl. In some such embodiments, one of $R^h$ and $R^k$ has one of the formulae D-i to D-v, as defined above. In certain such embodiments, one of $R^h$ or $R^k$ has one of the formulae D-1 to D-51, or has the formula embodied at the relevant position of any of the compounds depicted in Table 3 below.

Some embodiments of the invention relate to a compound of formula (I) characterized by at least one, two, three, four, or five of the following features(a)-(f):

(a) $R^a$ is hydrogen or $C_{1-3}$ alkyl;

(b) $R^{f1}$ and $R^{f2}$ together form a bond;

(c) Ring A is substituted with 0-2 $R^b$, where each $R^b$ independently is selected from the group consisting of $C_{1-3}$ aliphatic, $R^{2b}$, $R^{7b}$, -T¹-R²ᵇ, and -T¹-R⁷ᵇ, where T¹ is a $C_{1-3}$ alkylene chain;

(d) Ring B is a monocyclic 5- or 6-membered aryl or heteroaryl ring, which is substituted with 0-2 $R^c$, where each $R^c$ independently is selected from the group consisting of $C_{1-3}$ aliphatic, $R^{2c}$, $R^{7c}$, -T¹-R²ᶜ, and -T¹-R⁷ᶜ, where T¹ is a $C_{1-3}$ alkylene chain;

(e) Ring C is a mono- or bicyclic aryl or heteroaryl ring, which is substituted with 0-2 independently selected $R^d$ and 0-2 independently selected $R^{2d}$ or $C_{1-6}$ aliphatic groups; and (f) $R^e$ is hydrogen.

In some embodiments, the compound of formula (I) is characterized by all six of the features (a)-(f) above.

Some embodiments of the invention relate to a subgenus of the compounds of formula (I) defined by formula (VII):

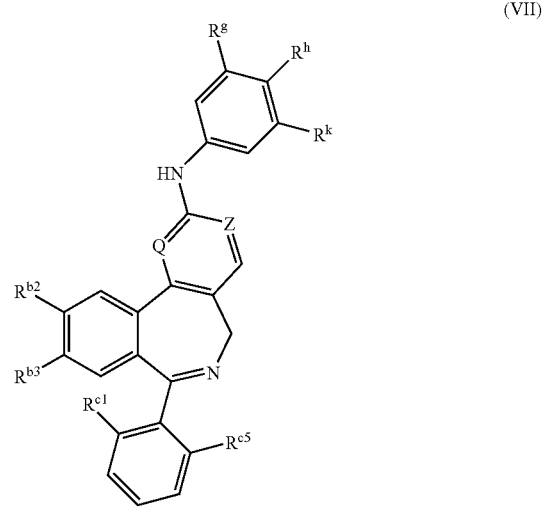

(VII)

wherein:
$R^e$ is hydrogen;
$R^{b2}$ and $R^{b3}$ are each independently selected from the group consisting of hydrogen, -halo, $C_{1-3}$ aliphatic, $C_{1-3}$ fluoroaliphatic, and —OR⁵, where R⁵ is hydrogen or $C_{1-3}$ aliphatic;
$R^{c1}$ and $R^{c5}$ are each independently selected from the group consisting of hydrogen, -halo, $C_{1-3}$ aliphatic, $C_{1-3}$ fluoroaliphatic, and —OR⁵, where R⁵ is hydrogen or $C_{1-3}$ aliphatic;
$R^g$ is selected from the group consisting of hydrogen, $C_{1-6}$ aliphatic, and $R^{2d}$; and
$R^h$ and $R^k$ are each independently hydrogen or $R^d$.

In some embodiments, the invention relates to a compound of formula (VII) wherein at least one of $R^h$ and $R^k$ has the formula —V-T³-R²ᵈ or —V-T³-R⁷ᵈ, where:
V is —C(O)N(R⁴)—;
T³ is a $C_{2-4}$ alkylene chain;
$R^{2d}$ is —N(R⁴)₂, where R⁴ is hydrogen or $C_{1-3}$ aliphatic, or two R⁴ on the same nitrogen atom, taken together with the nitrogen atom, form an optionally substituted 4- to 8-membered heterocyclyl or an optionally substituted 5- to 6-membered heteroaryl ring having, in addition to the nitrogen, 0-2 ring heteroatoms selected from N, O, and S; and
$R^{7d}$ is an optionally substituted 4- to 8-membered heterocyclyl or an optionally substituted 5- or 6-membered heteroaryl.

In some other embodiments, the invention relates to a compound of formula (VIII), wherein $R^g$ is hydrogen, and at least one of $R^h$ and $R^k$ is selected from the group consisting of —CO₂R⁵, —C(O)N(R⁴)₂, —C(=NR⁴)N(R⁴)₂, —C(O)N(R⁴)C(=NR⁴)—N(R⁴)₂, —N(R⁴)C(=NR⁴)—N(R⁴)—C(O)R⁵, or —NR⁴C(O)R⁵.

In a particular embodiment, the invention relates to a compound of formula (VIII), wherein:
$R^e$, $R^{b2}$, $R^g$, and $R^k$ are each hydrogen;
$R^{b3}$ and $R^{c1}$ are each independently selected from the group consisting of -halo, $C_{1-3}$ aliphatic, $C_{1-3}$ fluoroaliphatic, and —OR⁵, where R⁵ is hydrogen or $C_{1-3}$ aliphatic;
$R^{c5}$ is selected from the group consisting of hydrogen, -halo, $C_{1-3}$ aliphatic, $C_{1-3}$ fluoroaliphatic, and —OR⁵, where R⁵ is hydrogen or $C_{1-3}$ aliphatic;

$R^h$ is —CO$_2$H, —C(O)N(R$^4$)$_2$, —C(=NR$^4$)N(R$^4$)$_2$, —C(O)N(R$^4$)C(=NR$^4$)—N(R$^4$)$_2$, or —N(R$^4$)C(=NR$^4$)—N(R$^4$)—C(O)R$^5$, where R$^5$ is an optionally substituted 4- to 8-membered nitrogen-containing heterocyclyl ring, and —N(R$^4$)$_2$ is an optionally substituted 4- to 8-membered heterocyclyl ring having in addition to the nitrogen atom 0-2 heteroatoms selected from N, O, and S.

Some embodiments of the invention relate to a subgenus of the compounds of formula (I) defined by formula (VIII):

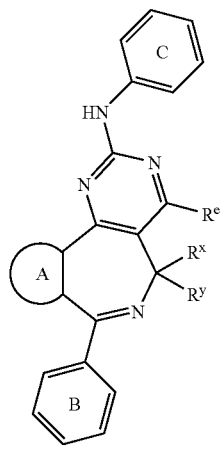

(VIII)

wherein:
Ring A is a substituted or unsubstituted 5 or 6-membered aryl, heteroaryl, cycloaliphatic, or heterocyclyl ring;
Ring B is substituted with 0-2 independently selected R$^c$ and 0-3 independently selected R$^{2c}$ or C$_{1-6}$ aliphatic groups;
Ring C is substituted 0-2 independently selected R$^d$ and 0-3 independently selected R$^{2d}$ or C$_{1-6}$ aliphatic groups; and
each of R$^c$, R$^{2c}$, R$^d$, R$^{2d}$, R$^e$, R$^x$, and R$^y$ has the values and preferred values described above for formulae (I)-(VII)

Compounds embodying any combination of the preferred values for the variables described herein are considered to be within the scope of the present invention.

Table 3 shows specific examples of compounds of formula (I).

TABLE 3

Aurora Kinase Inhibitors

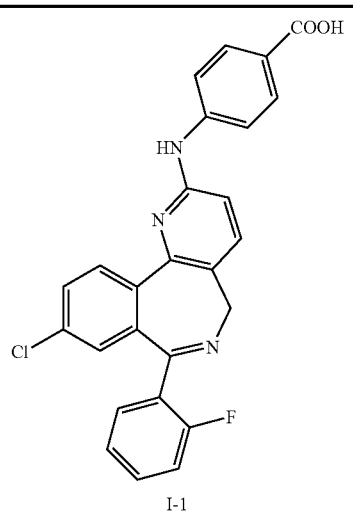

I-1

TABLE 3-continued

Aurora Kinase Inhibitors

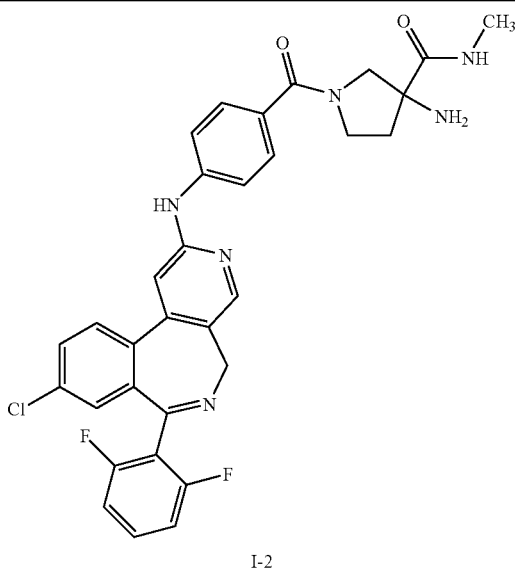

I-2

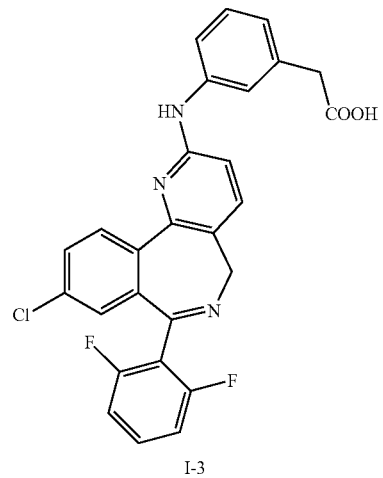

I-3

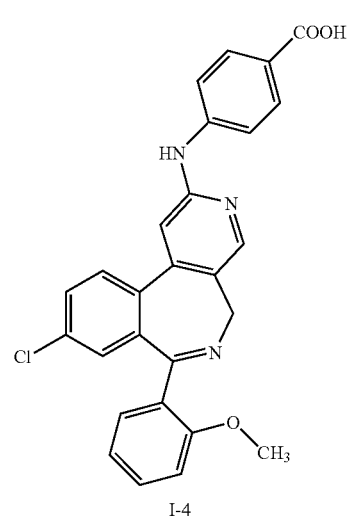

I-4

TABLE 3-continued
Aurora Kinase Inhibitors
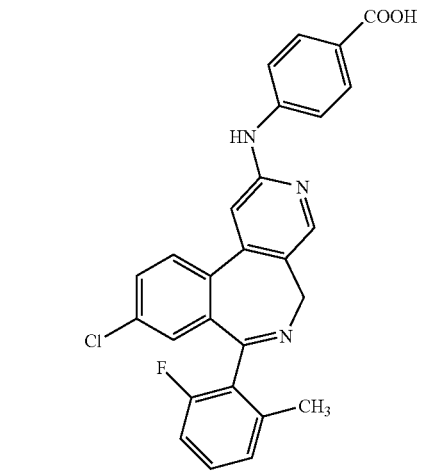
I-5
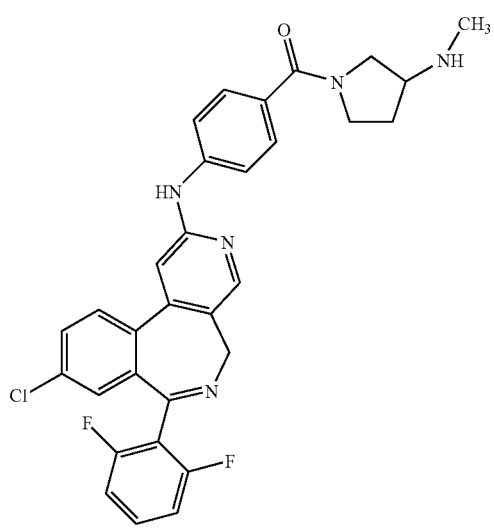
I-6
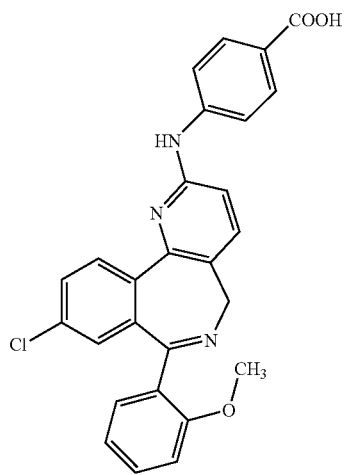
I-7
TABLE 3-continued
Aurora Kinase Inhibitors
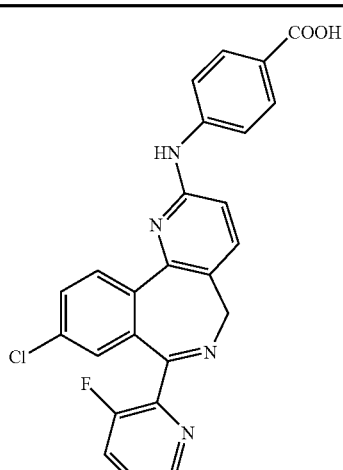
I-8
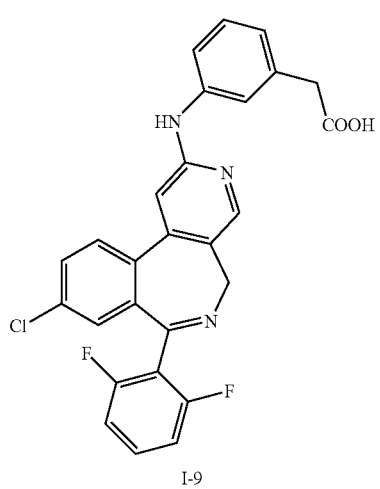
I-9
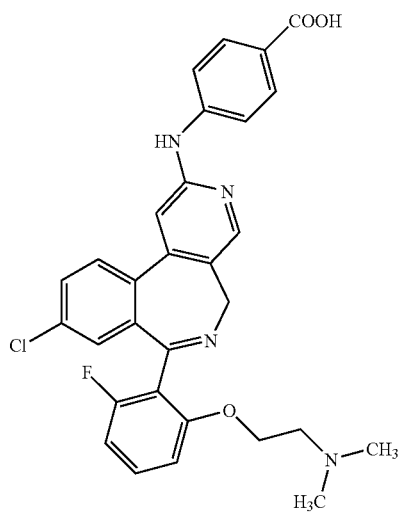
I-10

TABLE 3-continued
Aurora Kinase Inhibitors
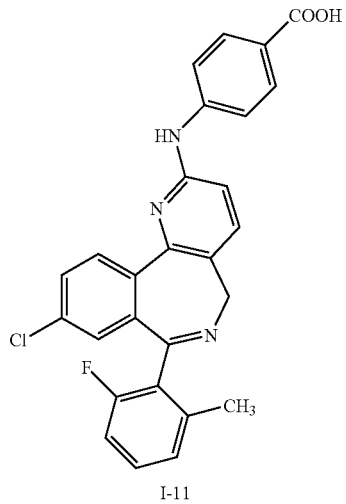
I-11
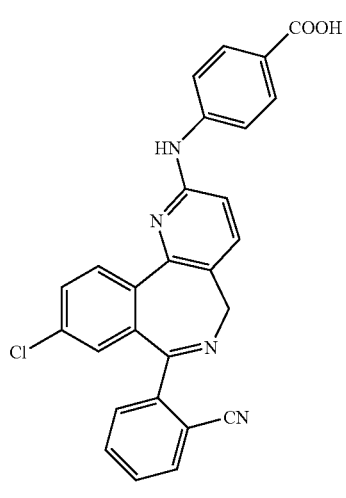
I-12
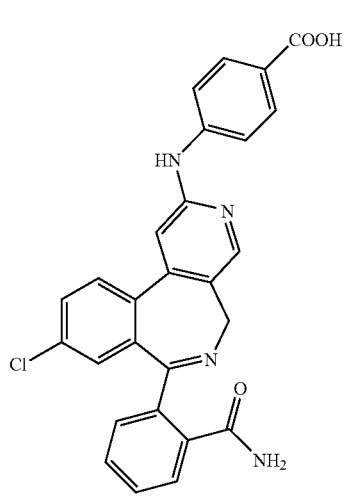
I-13
TABLE 3-continued
Aurora Kinase Inhibitors
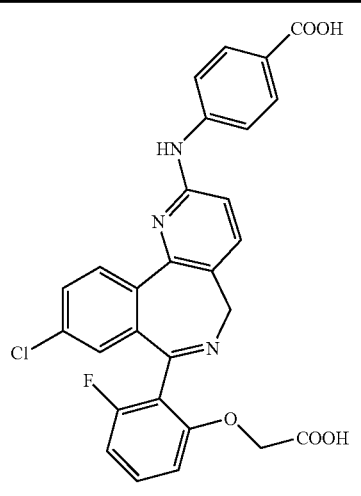
I-14
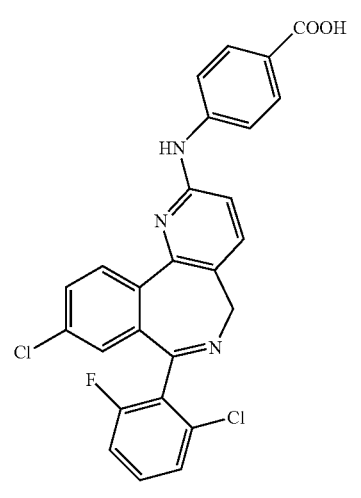
I-15
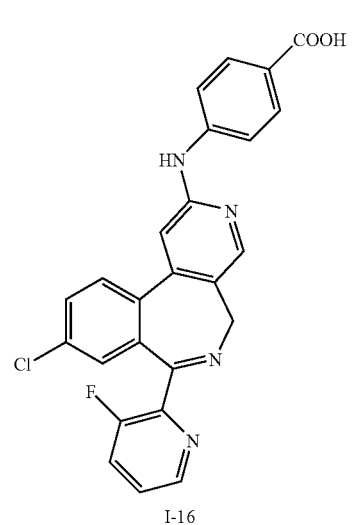
I-16

TABLE 3-continued
Aurora Kinase Inhibitors
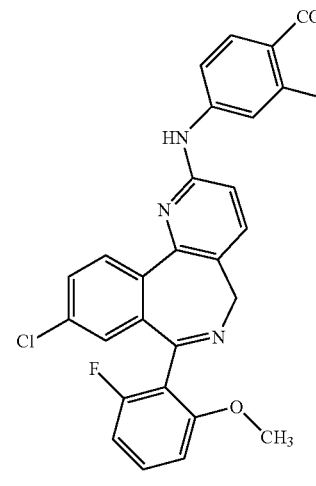
I-17
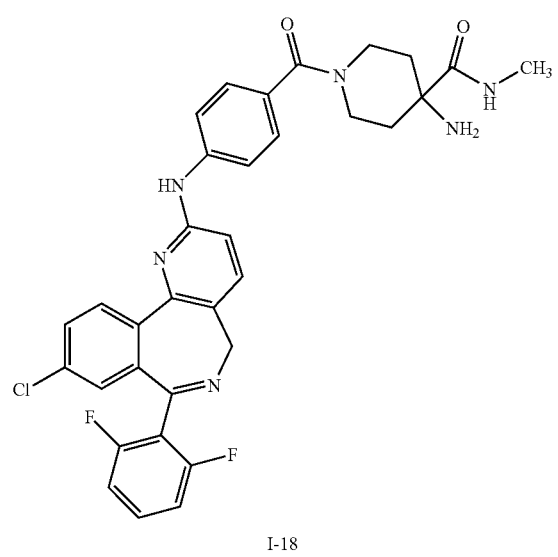
I-18
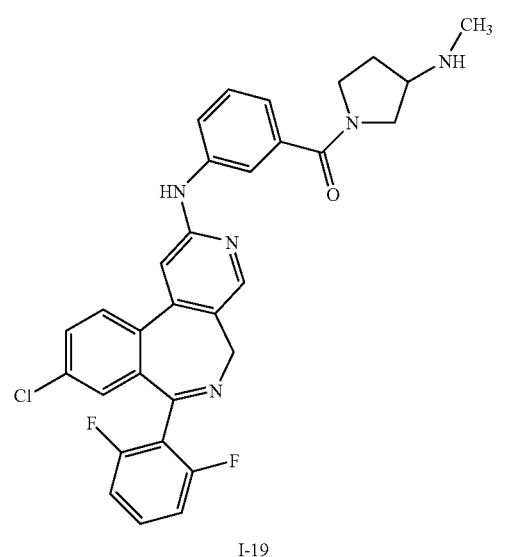
I-19
TABLE 3-continued
Aurora Kinase Inhibitors
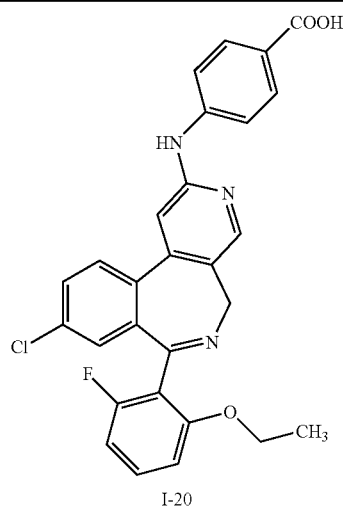
I-20
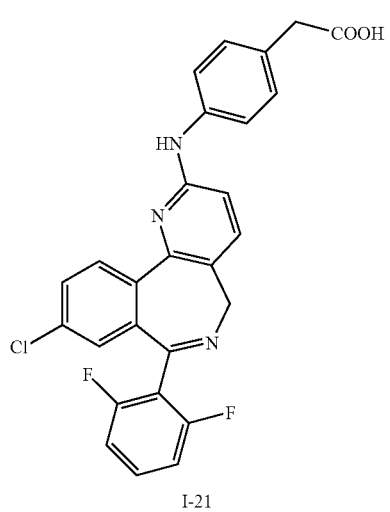
I-21
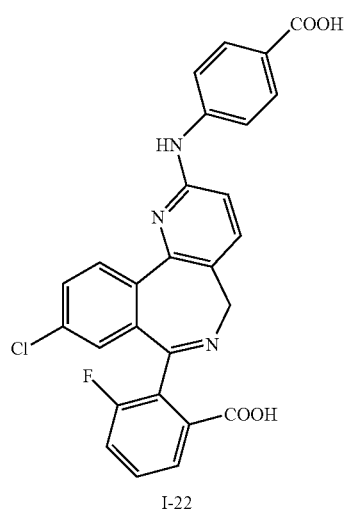
I-22

TABLE 3-continued
Aurora Kinase Inhibitors
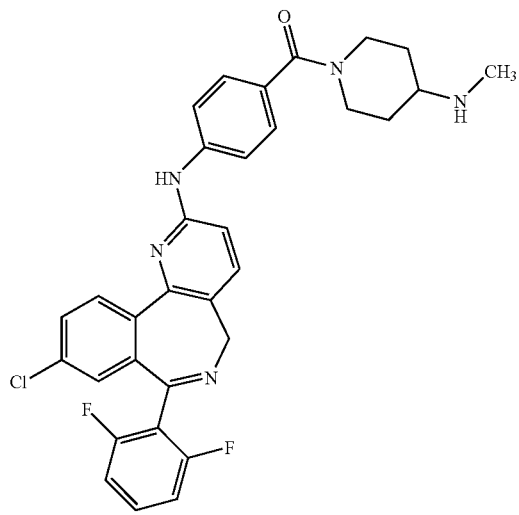
I-23
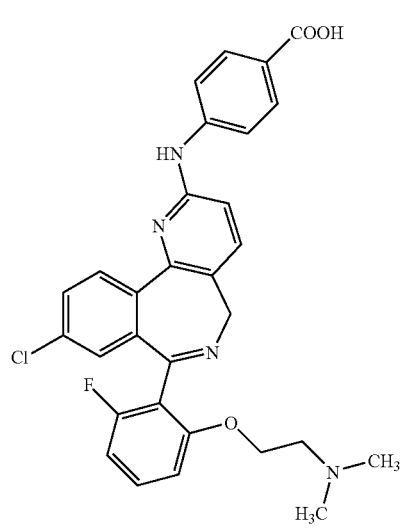
I-24
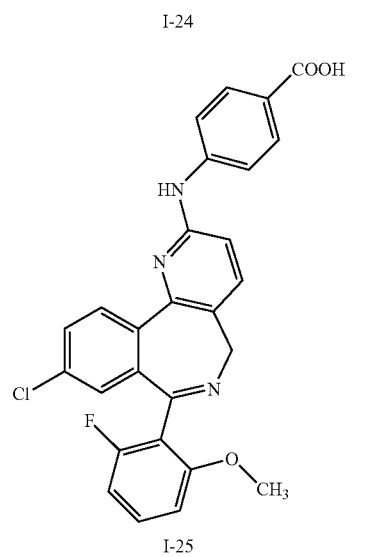
I-25
TABLE 3-continued
Aurora Kinase Inhibitors
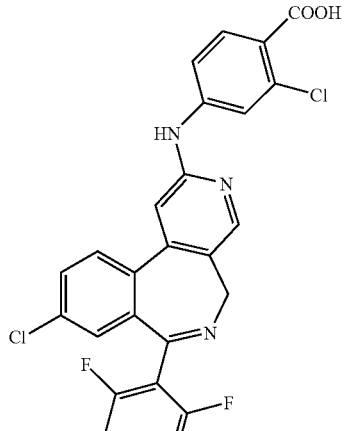
I-26
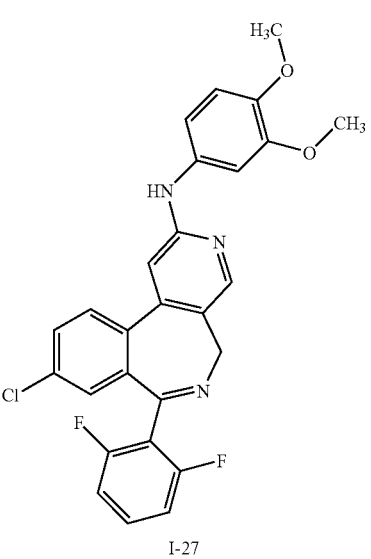
I-27
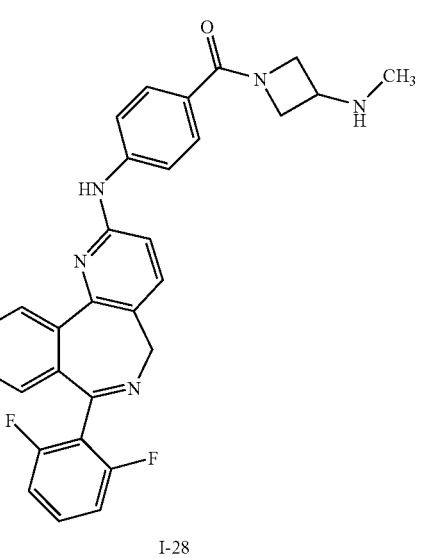
I-28

TABLE 3-continued
Aurora Kinase Inhibitors
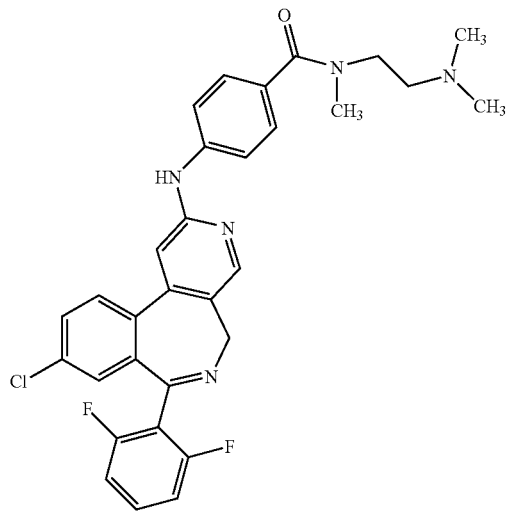
I-29
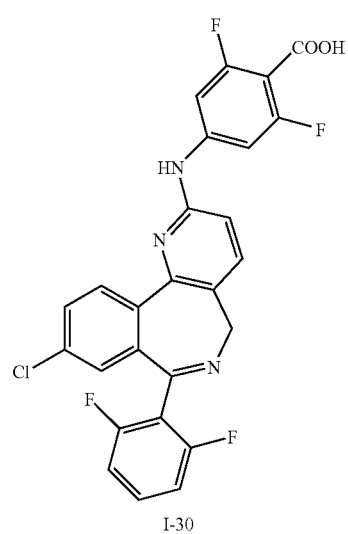
I-30
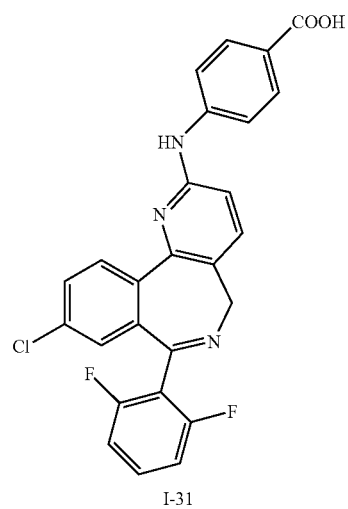
I-31
TABLE 3-continued
Aurora Kinase Inhibitors
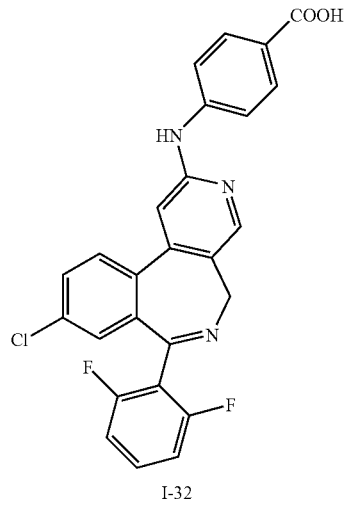
I-32
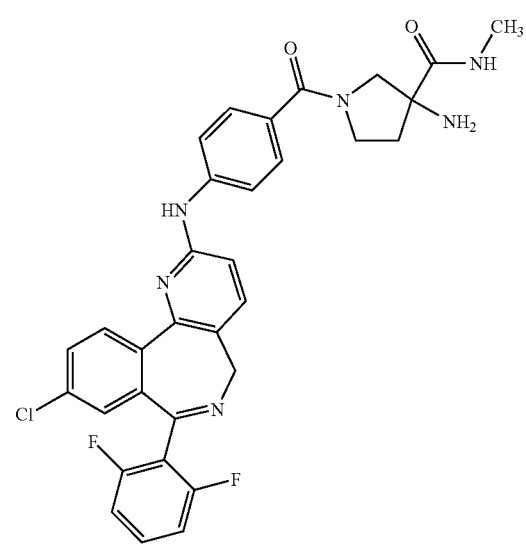
I-33
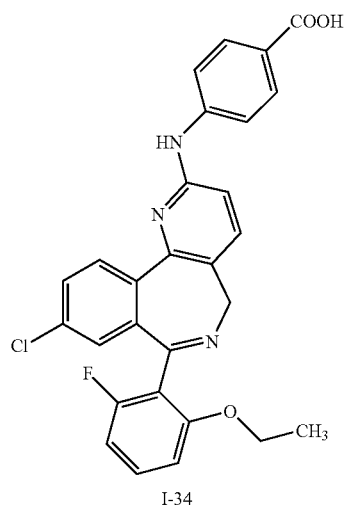
I-34

TABLE 3-continued
Aurora Kinase Inhibitors
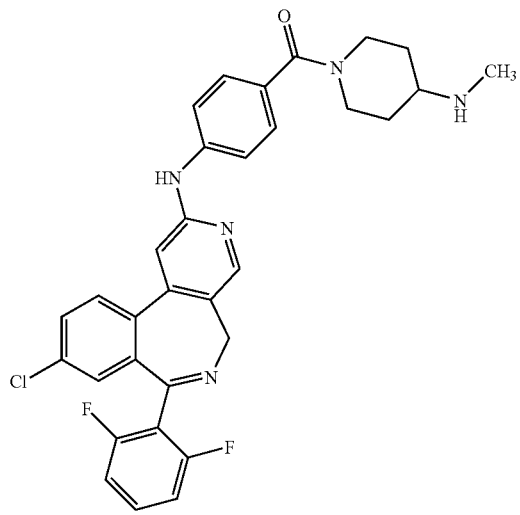
I-35
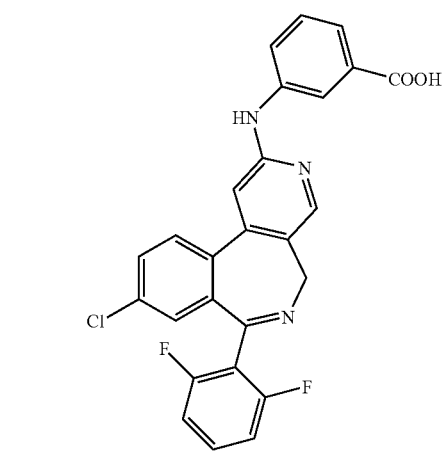
I-36
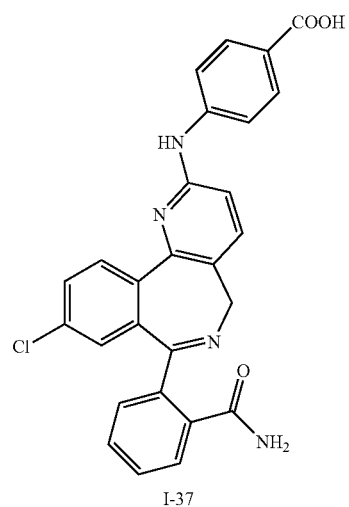
I-37
TABLE 3-continued
Aurora Kinase Inhibitors
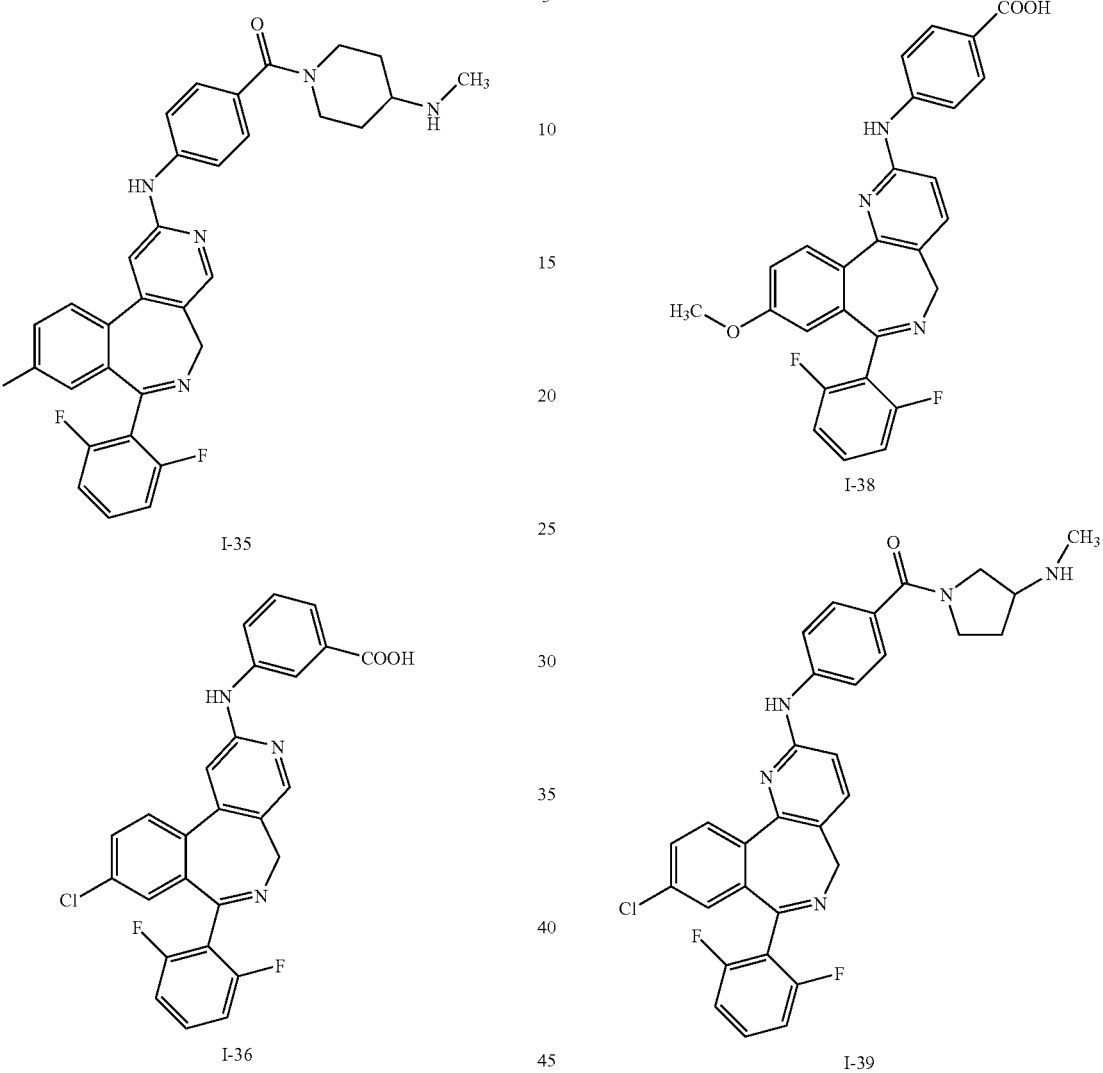
I-38
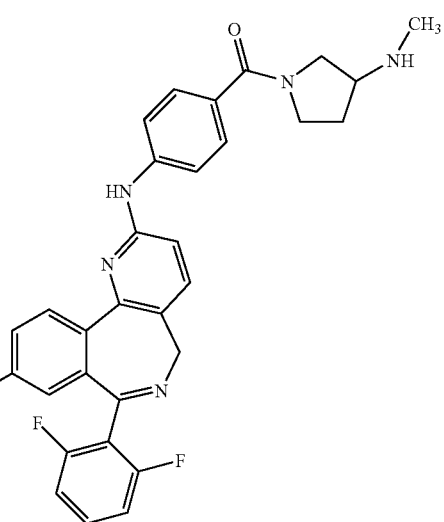
I-39
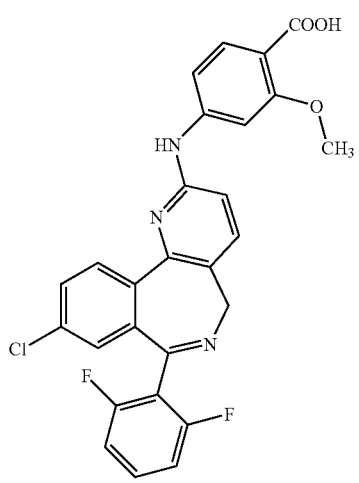
I-40

TABLE 3-continued
Aurora Kinase Inhibitors
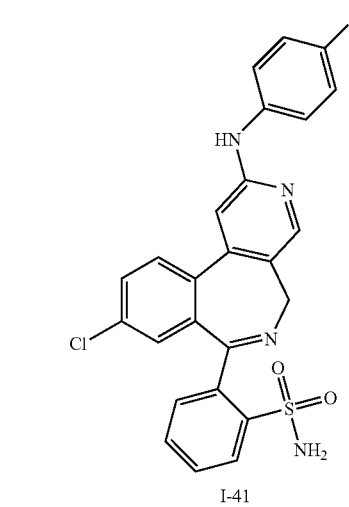
I-41
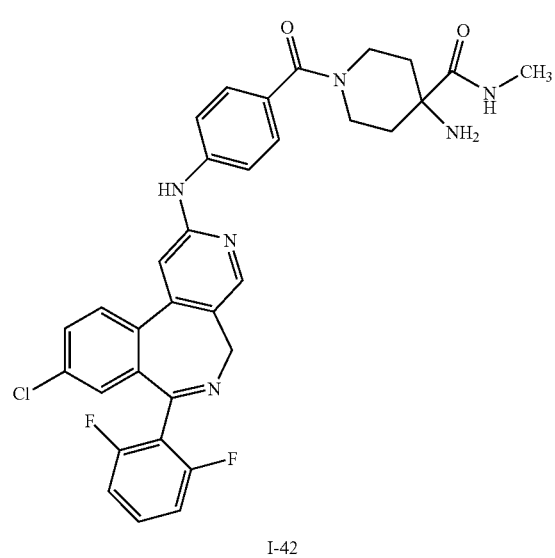
I-42
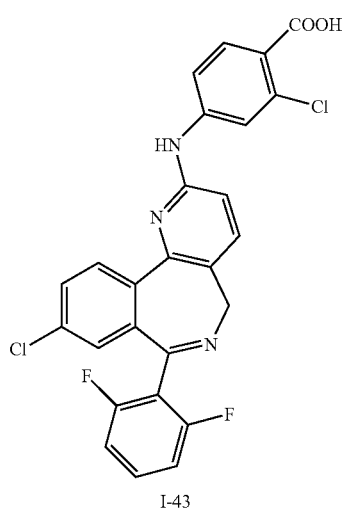
I-43
TABLE 3-continued
Aurora Kinase Inhibitors
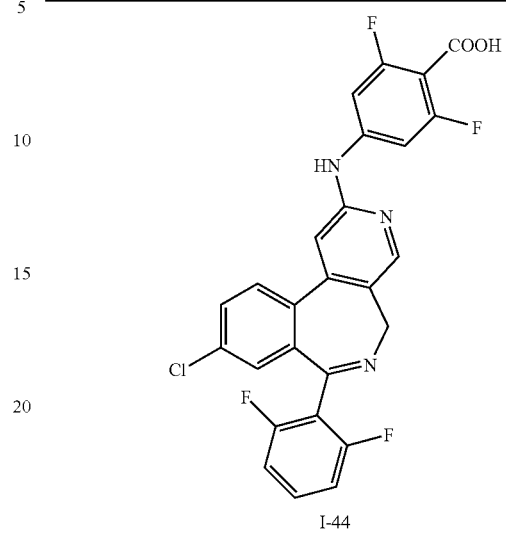
I-44
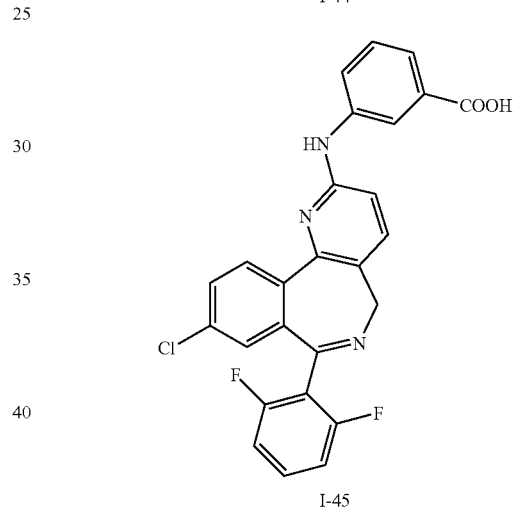
I-45
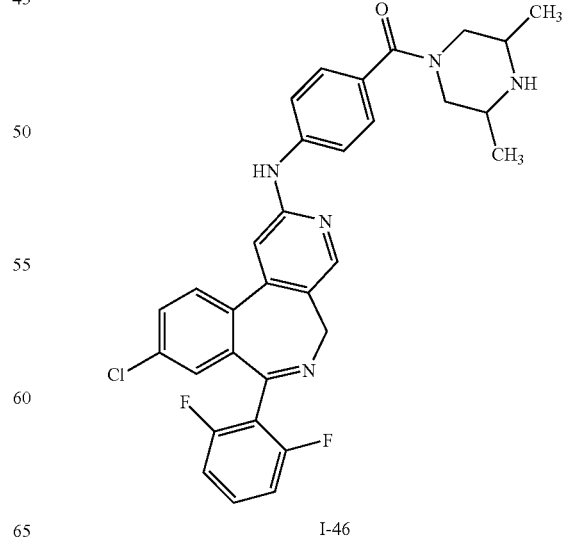
I-46

TABLE 3-continued
Aurora Kinase Inhibitors
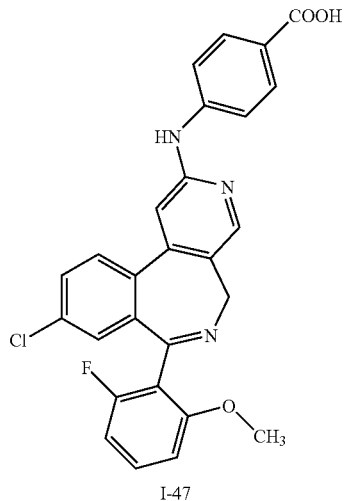
I-47
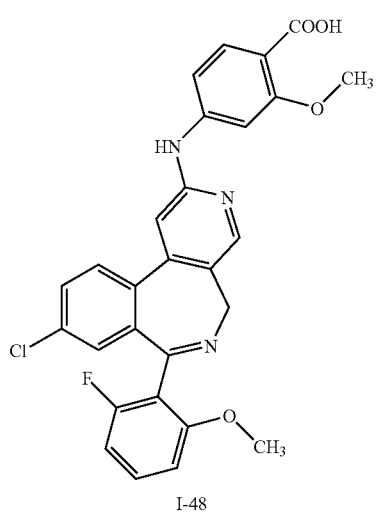
I-48
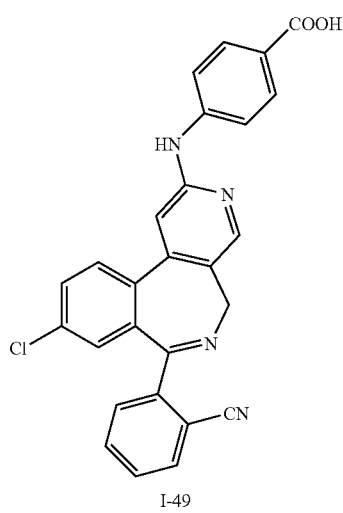
I-49
TABLE 3-continued
Aurora Kinase Inhibitors
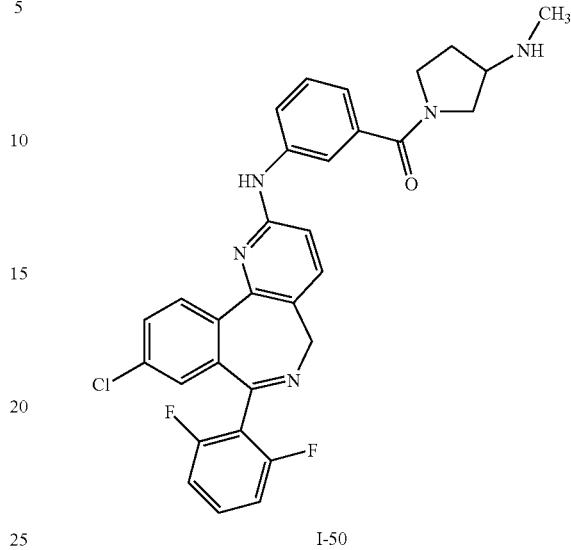
I-50
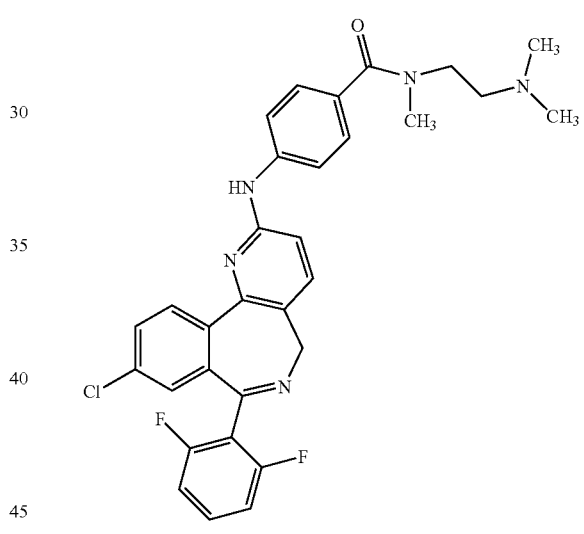
I-51
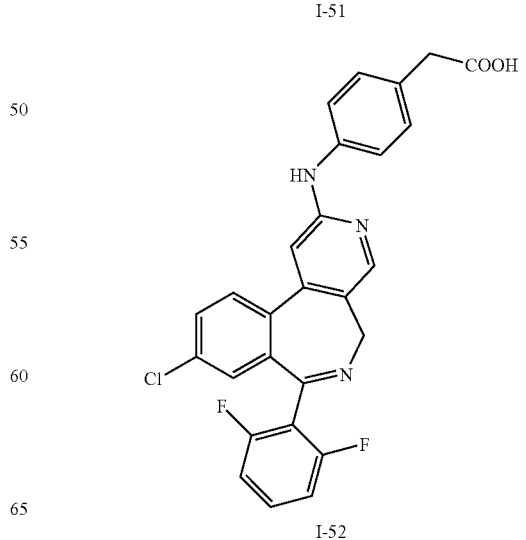
I-52

TABLE 3-continued
Aurora Kinase Inhibitors
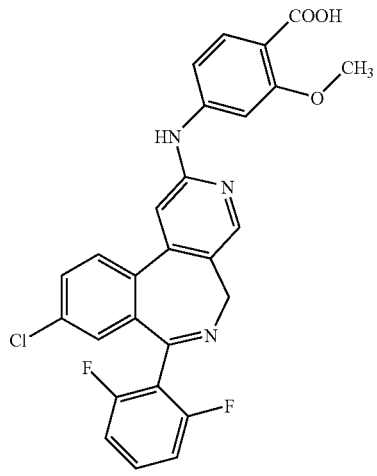
I-53
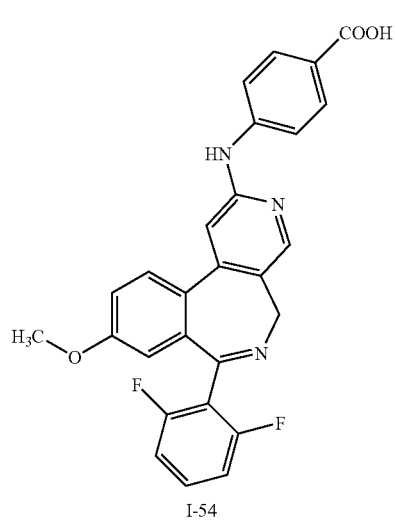
I-54
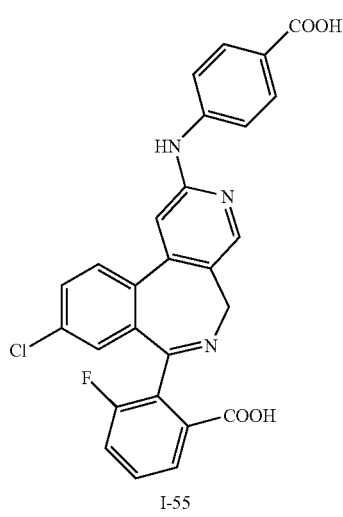
I-55
TABLE 3-continued
Aurora Kinase Inhibitors
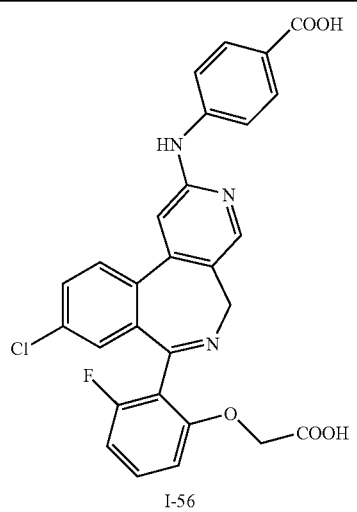
I-56
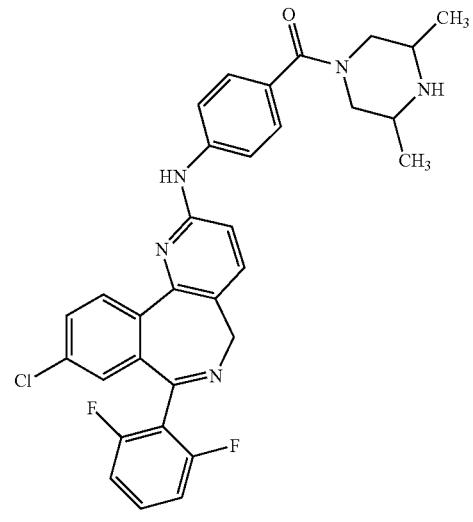
I-57
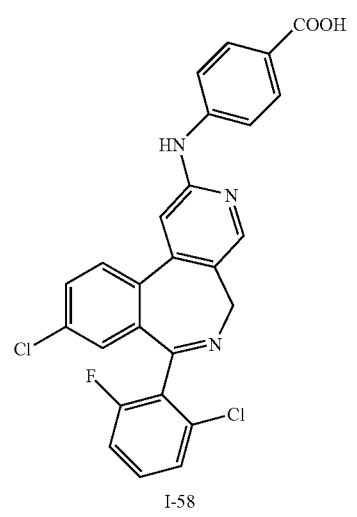
I-58

TABLE 3-continued
Aurora Kinase Inhibitors
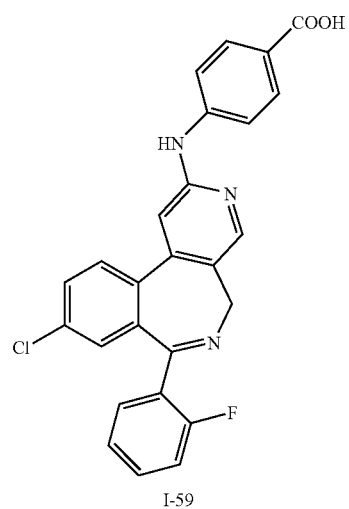
I-59
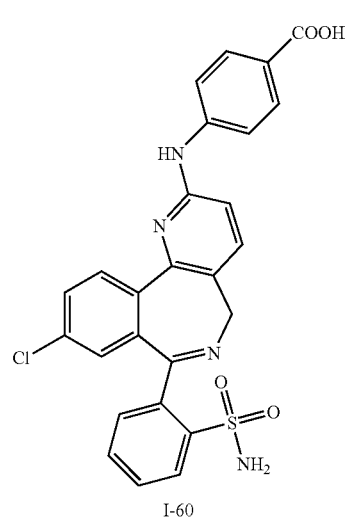
I-60
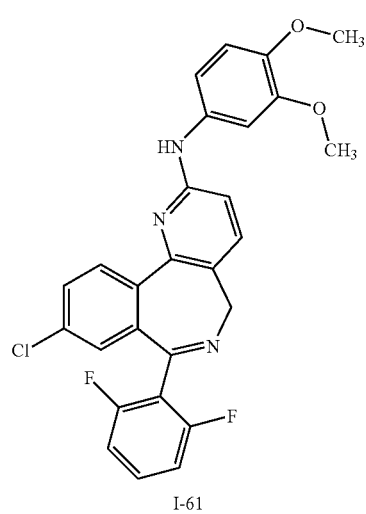
I-61
TABLE 3-continued
Aurora Kinase Inhibitors
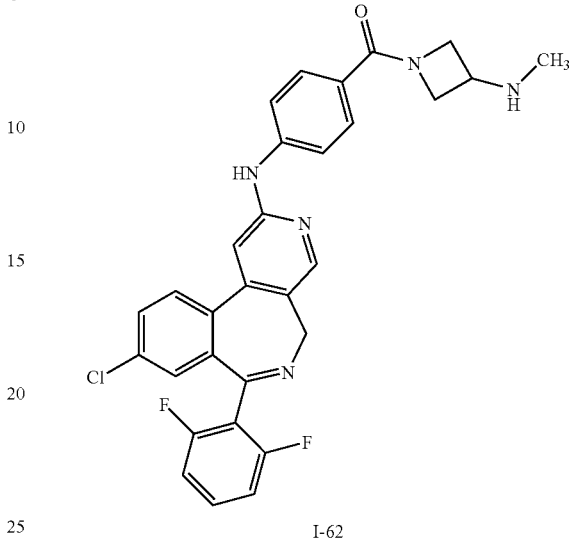
I-62
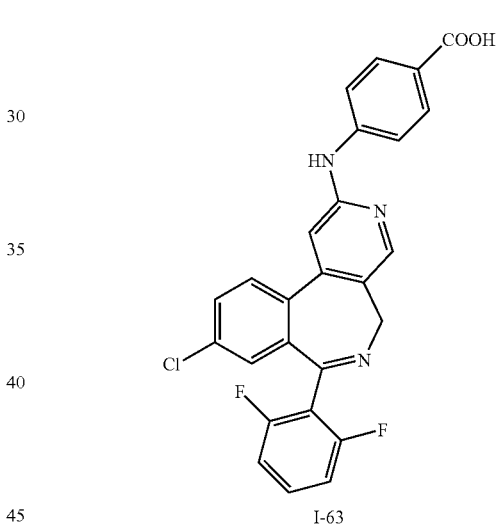
I-63
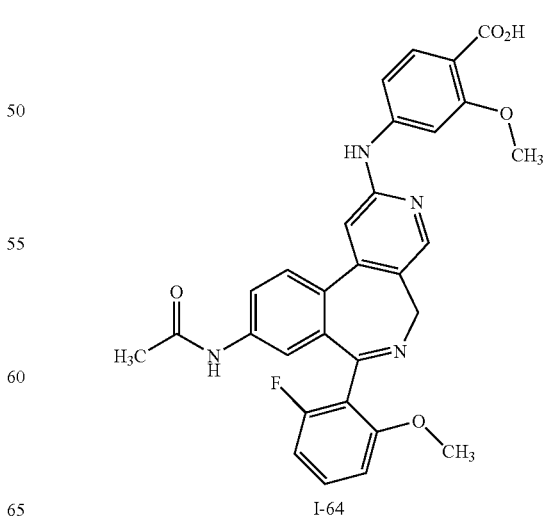
I-64

TABLE 3-continued
Aurora Kinase Inhibitors
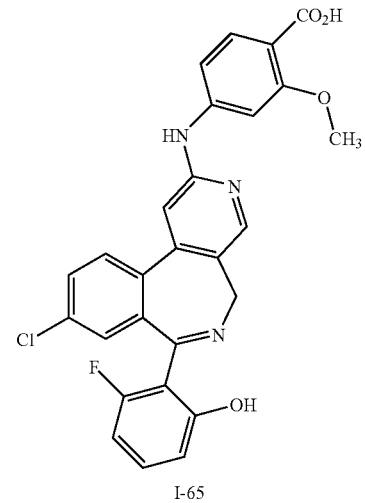
I-65
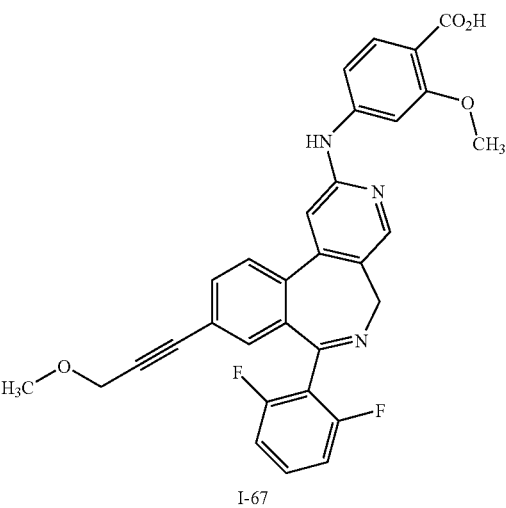
I-67
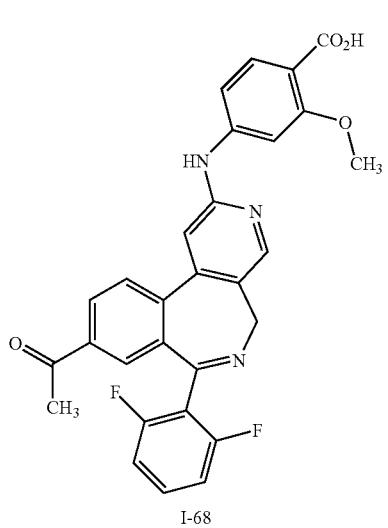
I-68
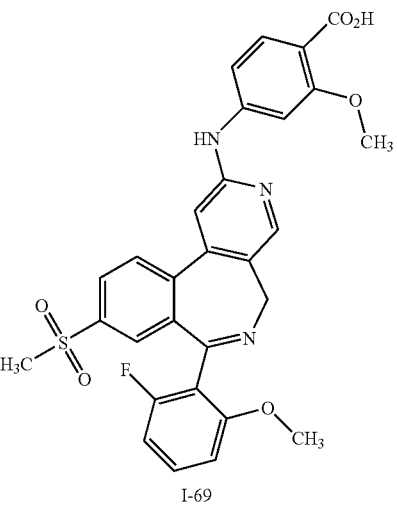
I-66
TABLE 3-continued
Aurora Kinase Inhibitors
I-69
The compounds in Table 3 above also may be identified by the following chemical names:

|      | Chemical Name |
|------|---------------|
| I-1  | 4-{[9-chloro-7-(2-fluorophenyl)-5H-pyrido[3,2-d][2]benzazepin-2-yl]amino}-benzoic acid |
| I-2  | 3-amino-1-(4-{[9-chloro-7-(2,6-difluorophenyl)-5H-pyrido[3,4-d][2]-benzazepin-2-yl]amino}benzoyl)-N-methylpyrrolidine-3-carboxamide |
| I-3  | (3-{[9-chloro-7-(2,6-difluorophenyl)-5H-pyrido[3,2-d][2]benzazepin-2-yl]-amino}phenyl)acetic acid |
| I-4  | 4-{[9-chloro-7-(2-methoxyphenyl)-5H-pyrido[3,4-d][2]benzazepin-2-yl]-amino}benzoic acid |
| I-5  | 4-{[9-chloro-7-(2-fluoro-6-methylphenyl)-5H-pyrido[3,4-d][2]benzazepin-2-yl]amino}benzoic acid |
| I-6  | 9-chloro-7-(2,6-difluorophenyl)-N-(4-{[3-(methylamino)pyrrolidin-1-yl]-carbonyl}phenyl)-5H-pyrido[3,4-d][2]benzazepin-2-amine |
| I-7  | 4-{[9-chloro-7-(2-methoxyphenyl)-5H-pyrido[3,2-d][2]benzazepin-2-yl]-amino}benzoic acid |
| I-8  | 4-{[9-chloro-7-(3-fluoropyridin-2-yl)-5H-pyrido[3,2-d][2]benzazepin-2-yl]-amino}benzoic acid |
| I-9  | (3-{[9-chloro-7-(2,6-difluorophenyl)-5H-pyrido[3,4-d][2]benzazepin-2-yl]-amino}phenyl)acetic acid |
| I-10 | 4-[(9-chloro-7-{2-[2-(dimethylamino)ethoxy]-6-fluorophenyl}-5H-pyrido[3,4-d][2]benzazepin-2-yl)amino]benzoic acid |
| I-11 | 4-{[9-chloro-7-(2-fluoro-6-methylphenyl)-5H-pyrido[3,2-d][2]benzazepin-2-yl]amino}benzoic acid |
| I-12 | 4-{[9-chloro-7-(2-cyanophenyl)-5H-pyrido[3,2-d][2]benzazepin-2-yl]amino}-benzoic acid |
| I-13 | 4-({7-[2-(aminocarbonyl)phenyl]-9-chloro-5H-pyrido[3,4-d][2]benzazepin-2-yl}amino)benzoic acid |
| I-14 | 4-({7-[2-(carboxymethoxy)-6-fluorophenyl]-9-chloro-5H-pyrido[3,2-d][2]-benzazepin-2-yl}amino)benzoic acid |
| I-15 | 4-{[9-chloro-7-(2-chloro-6-fluorophenyl)-5H-pyrido[3,2-d][2]benzazepin-2-yl]amino}benzoic acid |
| I-16 | 4-{[9-chloro-7-(3-fluoropyridin-2-yl)-5H-pyrido[3,4-d][2]benzazepin-2-yl]-amino}benzoic acid |
| I-17 | 4-{[9-chloro-7-(2-fluoro-6-methoxyphenyl)-5H-pyrido[3,2-d][2]benzazepin-2-yl]amino}-2-methoxybenzoic acid |
| I-18 | 4-amino-1-(4-{[9-chloro-7-(2,6-difluorophenyl)-5H-pyrido[3,2-d][2]-benzazepin-2-yl]amino}benzoyl)-N-methylpiperidine-4-carboxamide |
| I-19 | 9-chloro-7-(2,6-difluorophenyl)-N-(3-{[3-(methylamino)pyrrolidin-1-yl]-carbonyl}phenyl)-5H-pyrido[3,4-d][2]benzazepin-2-amine |
| I-20 | 4-{[9-chloro-7-(2-ethoxy-6-fluorophenyl)-5H-pyrido[3,4-d][2]benzazepin-2-yl]amino}benzoic acid |
| I-21 | (4-{[9-chloro-7-(2,6-difluorophenyl)-5H-pyrido[3,2-d][2]benzazepin-2-yl]-amino}phenyl)acetic acid |
| I-22 | 2-{2-[(4-carboxyphenyl)amino]-9-chloro-5H-pyrido[3,2-d][2]benzazepin-7-yl}-3-fluorobenzoic acid |
| I-23 | 9-chloro-7-(2,6-difluorophenyl)-N-(4-{[4-(methylamino)piperidin-1-yl]-carbonyl}phenyl)-5H-pyrido[3,2-d][2]benzazepin-2-amine |
| I-24 | 4-[(9-chloro-7-{2-[2-(dimethylamino)ethoxy]-6-fluorophenyl}-5H-pyrido[3,2-d][2]benzazepin-2-yl)amino]benzoic acid |
| I-25 | 4-{[9-chloro-7-(2-fluoro-6-methoxyphenyl)-5H-pyrido[3,2-d][2]benzazepin-2-yl]amino}benzoic acid |
| I-26 | 2-chloro-4-{[9-chloro-7-(2,6-difluorophenyl)-5H-pyrido[3,4-d][2]-benzazepin-2-yl]amino}benzoic acid |
| I-27 | 9-chloro-7-(2,6-difluorophenyl)-N-(3,4-dimethoxyphenyl)-5H-pyrido[3,4-d]-[2]benzazepin-2-amine |
| I-28 | 9-chloro-7-(2,6-difluorophenyl)-N-(4-{[3-(methylamino)azetidin-1-yl]-carbonyl}phenyl)-5H-pyrido[3,2-d][2]benzazepin-2-amine |
| I-29 | 4-{[9-chloro-7-(2,6-difluorophenyl)-5H-pyrido[3,4-d][2]benzazepin-2-yl]-amino}-N-[2-(dimethylamino)ethyl]-N-methylbenzamide |
| I-30 | 4-{[9-chloro-7-(2,6-difluorophenyl)-5H-pyrido[3,2-d][2]benzazepin-2-yl]-amino}-2,6-difluorobenzoic acid |
| I-31 | 4-{[9-chloro-7-(2,6-difluorophenyl)-5H-pyrido[3,2-d][2]benzazepin-2-yl]-amino}benzoic acid |
| I-32 | 4-{[9-chloro-7-(2,6-difluorophenyl)-5H-pyrido[3,4-d][2]benzazepin-2-yl]-amino}benzoic acid |
| I-33 | 3-amino-1-(4-{[9-chloro-7-(2,6-difluorophenyl)-5H-pyrido[3,2-d][2]-benzazepin-2-yl]amino}benzoyl)-N-methylpyrrolidine-3-carboxamide |
| I-34 | 4-{[9-chloro-7-(2-ethoxy-6-fluorophenyl)-5H-pyrido[3,2-d][2]benzazepin-2-yl]amino}benzoic acid |
| I-35 | 9-chloro-7-(2,6-difluorophenyl)-N-(4-{[4-(methylamino)piperidin-1-yl]-carbonyl}phenyl)-5H-pyrido[3,4-d][2]benzazepin-2-amine |
| I-36 | 3-{[9-chloro-7-(2,6-difluorophenyl)-5H-pyrido[3,4-d][2]benzazepin-2-yl]-amino}benzoic acid |
| I-37 | 4-({7-[2-(aminocarbonyl)phenyl]-9-chloro-5H-pyrido[3,2-d][2]benzazepin-2-yl}amino)benzoic acid |
| I-38 | 4-{[7-(2,6-difluorophenyl)-9-methoxy-5H-pyrido[3,2-d][2]benzazepin-2-yl]-amino}benzoic acid |

|  | Chemical Name |
|---|---|
| I-39 | 9-chloro-7-(2,6-difluorophenyl)-N-(4-{[3-(methylamino)pyrrolidin-1-yl]-carbonyl}phenyl)-5H-pyrido[3,2-d][2]benzazepin-2-amine |
| I-40 | 4-{[9-chloro-7-(2,6-difluorophenyl)-5H-pyrido[3,2-d][2]benzazepin-2-yl]-amino}-2-methoxybenzoic acid |
| I-41 | 4-({7-[2-(aminosulfonyl)phenyl]-9-chloro-5H-pyrido[3,4-d][2]benzazepin-2-yl}amino)benzoic acid |
| I-42 | 4-amino-1-(4-{[9-chloro-7-(2,6-difluorophenyl)-5H-pyrido[3,4-d][2]-benzazepin-2-yl]amino}benzoyl)-N-methylpiperidine-4-carboxamide |
| I-43 | 2-chloro-4-{[9-chloro-7-(2,6-difluorophenyl)-5H-pyrido[3,2-d][2]-benzazepin-2-yl]amino}benzoic acid |
| I-44 | 4-{[9-chloro-7-(2,6-difluorophenyl)-5H-pyrido[3,4-d][2]benzazepin-2-yl]-amino}-2,6-difluorobenzoic acid |
| I-45 | 3-{[9-chloro-7-(2,6-difluorophenyl)-5H-pyrido[3,2-d][2]benzazepin-2-yl]-amino}benzoic acid |
| I-46 | 9-chloro-7-(2,6-difluorophenyl)-N-{4-[(3,5-dimethylpiperazin-1-yl)carbonyl]phenyl}-5H-pyrido[3,4-d][2]benzazepin-2-amine |
| I-47 | 4-{[9-chloro-7-(2-fluoro-6-methoxyphenyl)-5H-pyrido[3,4-d][2]benzazepin-2-yl]amino}benzoic acid |
| I-48 | 4-{[9-chloro-7-(2-fluoro-6-methoxyphenyl)-5H-pyrido[3,4-d][2]benzazepin-2-yl]amino}-2-methoxybenzoic acid |
| I-49 | 4-{[9-chloro-7-(2-cyanophenyl)-5H-pyrido[3,4-d][2]benzazepin-2-yl]amino}-benzoic acid |
| I-50 | 9-chloro-7-(2,6-difluorophenyl)-N-(3-{[3-(methylamino)pyrrolidin-1-yl]-carbonyl}phenyl)-5H-pyrido[3,2-d][2]benzazepin-2-amine |
| I-51 | 4-{[9-chloro-7-(2,6-difluorophenyl)-5H-pyrido[3,2-d][2]benzazepin-2-yl]-amino}-N-[2-(dimethylamino)ethyl]-N-methylbenzamide |
| I-52 | (4-{[9-chloro-7-(2,6-difluorophenyl)-5H-pyrido[3,4-d][2]benzazepin-2-yl]-amino}phenyl)acetic acid |
| I-53 | 4-{[9-chloro-7-(2,6-difluorophenyl)-5H-pyrido[3,4-d][2]benzazepin-2-yl]-amino}-2-methoxybenzoic acid |
| I-54 | 4-{[7-(2,6-difluorophenyl)-9-methoxy-5H-pyrido[3,4-d][2]benzazepin-2-yl]-amino}benzoic acid |
| I-55 | 2-{2-[(4-carboxyphenyl)amino]-9-chloro-5H-pyrido[3,4-d][2]benzazepin-7-yl}-3-fluorobenzoic acid |
| I-56 | 4-({7-[2-(carboxymethoxy)-6-fluorophenyl]-9-chloro-5H-pyrido[3,4-d][2]-benzazepin-2-yl}amino)benzoic acid |
| I-57 | 9-chloro-7-(2,6-difluorophenyl)-N-{4-[(3,5-dimethylpiperazin-1-yl)-carbonyl]phenyl}-5H-pyrido[3,2-d][2]benzazepin-2-amine |
| I-58 | 4-{[9-chloro-7-(2-chloro-6-fluorophenyl)-5H-pyrido[3,4-d][2]benzazepin-2-yl]amino}benzoic acid |
| I-59 | 4-{[9-chloro-7-(2-fluorophenyl)-5H-pyrido[3,4-d][2]benzazepin-2-yl]amino}-benzoic acid |
| I-60 | 4-({7-[2-(aminosulfonyl)phenyl]-9-chloro-5H-pyrido[3,2-d][2]benzazepin-2-yl}amino)benzoic acid |
| I-61 | 9-chloro-7-(2,6-difluorophenyl)-N-(3,4-dimethoxyphenyl)-5H-pyrido[3,2-d]-[2]benzazepin-2-amine |
| I-62 | 9-chloro-7-(2,6-difluorophenyl)-N-(4-{[3-(methylamino)azetidin-1-yl]-carbonyl}phenyl)-5H-pyrido[3,4-d][2]benzazepin-2-amine |
| I-63 | 4-{[9-chloro-7-(2,6-difluorophenyl)-5H-pyrido[3,4-d][2]benzazepin-2-yl]amino}-benzoic acid |
| I-64 | 4-{[9-(acetylamino)-7-(2-fluoro-6-methoxyphenyl)-5H-pyrido[3,4-d][2]-benzazepin-2-yl]amino}-2-methoxybenzoic acid |
| I-65 | 4-{[9-chloro-7-(2-fluoro-6-hydroxyphenyl)-5H-pyrido[3,4-d][2]benzazepin-2-yl]amino}-2-methoxybenzoic acid |
| I-66 | 4-{[7-(2,6-difluorophenyl)-9-pent-1-yn-1-yl-5H-pyrido[3,4-d][2]benzazepin-2-yl]amino}-2-methoxybenzoic acid |
| I-67 | 4-{[7-(2,6-difluorophenyl)-9-(3-methoxyprop-1-yn-1-yl)-5H-pyrido[3,4-d]-[2]benzazepin-2-yl]amino}-2-methoxybenzoic acid |
| I-68 | 4-{[9-acetyl-7-(2,6-difluorophenyl)-5H-pyrido[3,4-d][2]benzazepin-2-yl]-amino}-2-methoxybenzoic acid |
| I-69 | 4-{[7-(2-fluoro-6-methoxyphenyl)-9-(methylsulfonyl)-5H-pyrido[3,4-d][2]-benzazepin-2-yl]amino}-2-methoxybenzoic acid |

The compounds of the present invention can be prepared by methods known to one of ordinary skill in the art and/or by reference to the synthetic routes set forth in Scheme 1 below. One of ordinary skill in the art will recognize that variations in reaction conditions, including variations in solvent, reagents, catalysts, and reaction temperature may be possible for each of the reactions described below. Alternate synthetic routes are also possible.

Scheme 1 below depicts a general synthetic route for he preparation of compounds of formula v or ix, wherein each of Rings A and B is an optionally substituted phenyl ring. One of ordinary skill in the art will appreciate that certain compounds of formula v or ix wherein one or both of Rings A and B is other than phenyl can be prepared by a route analogous to that outlined in Scheme 1, by appropriate selection of the ketone reactant in steps 2 and/or 2a. One of ordinary skill in the art will furthermore appreciate that certain compounds of formula v or ix wherein Ring C is other than phenyl can be prepared by routes analogous to that outlined in Scheme 1, by appropriate selection of the amine reactant in steps 4 and/or 4a.

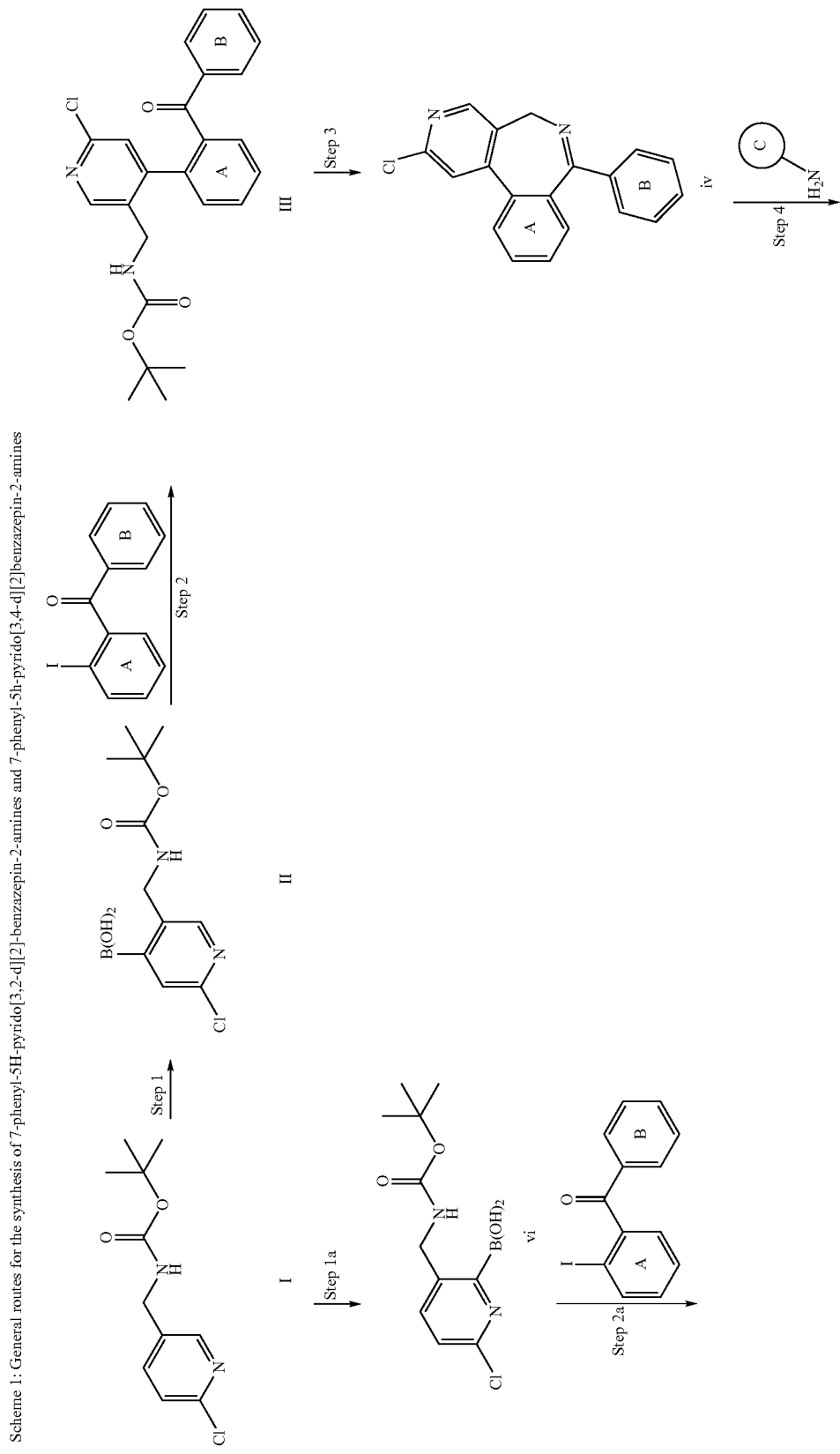
Scheme 1: General routes for the synthesis of 7-phenyl-5H-pyrido[3,2-d][2]-benzazepin-2-amines and 7-phenyl-5h-pyrido[3,4-d][2]benzazepin-2-amines -continued
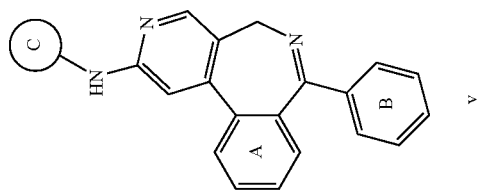
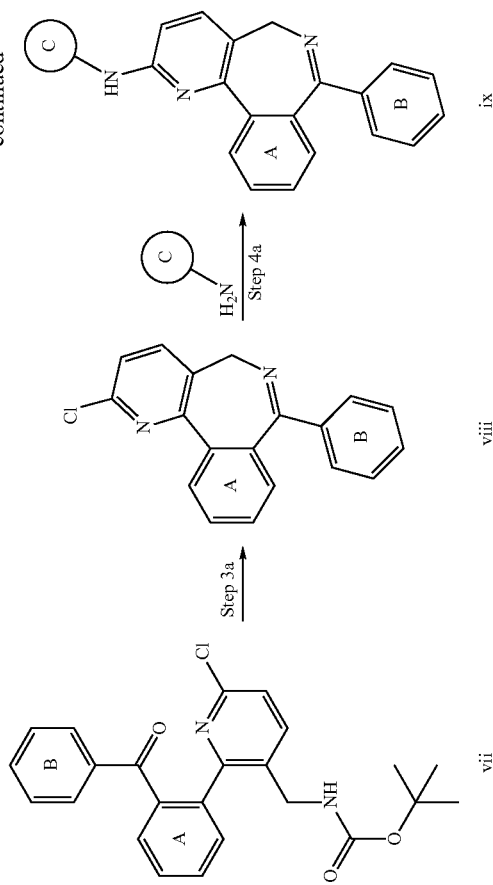

Methods for the synthesis of compound (i) have been described in the literature (Caddick et al, *Tetrahedron,* 2003, 59, 5417). The preparation of boronic acid (ii) may be accomplished by lithiation of compound (i) with t-butyllithium and subsequent reaction with a boronic acid trialkylester as described by Peukert et al, *J. Med. Chem.* 2003, 46, 486. Alternatively, regioisomer (vi) may be prepared by directed ortho metalation of compound (i) as described by Kondo et al, *JACS* 1999, 121, 3539 or by Fort et al, *Tet. Lett.* 2000, 41, 303 and subsequent reaction with a boronic acid trialkylester.

Compounds (iii) or (vii) may be prepared via a palladium-mediated coupling of compounds (ii) or (vi), respectively, with an appropriately-substituted o-iodo diarylketone as shown in steps 2 and 2a.

Removal of the BOC protecting group from compounds (iii) or (vii) and subsequent cydization to the pyridobenzazepines (iv) and (viii) as shown in steps 3 and 3a, respectively, may be accomplished by treatment with a strong acid, e.g. trifluoroacetic acid.

Compounds (v) or (ix) may be prepared via a palladium-mediated amination of compounds (iv) or (viii), respectively, with an appropriately-substituted amine as shown in steps 4 and 4a, as described in the literature, e.g. Buchwald et al, *Org. Lett.* 2005, 7, 3965 and Yin et al, *Org. Lett.* 2002, 4, 3481.

The compounds of this invention are inhibitors of Aurora kinase. The compounds can be assayed in vitro or in vivo for their ability to bind to and/or inhibit an Aurora kinase. In vitro assays include assays to determine inhibition of the ability of an Aurora kinase to phosphorylate a substrate protein or peptide. Alternate in vitro assays quantitate the ability of the compound to bind to an Aurora kinase. Inhibitor binding may be measured by radiolabelling the inhibitor prior to binding, isolating the inhibitor/Aurora kinase complex and determining the amount of radiolabel bound. Alternatively, inhibitor binding may be determined by running a competition experiment in which new inhibitors are incubated with Aurora kinase bound to a known radioligand. The compounds also can be assayed for their ability to affect cellular or physiological functions mediated by Aurora kinase activity. Assays for each of these activities are described in the Examples and/or are known in the art.

In another aspect, therefore, the invention provides a method for inhibiting Aurora kinase activity in a cell, comprising contacting a cell in which inhibition of Aurora kinase is desired with an Aurora kinase inhibitor of formula (I). In some embodiments, the Aurora kinase inhibitor interacts with and reduces the activity of all enzymes of the Aurora kinase family in the cell. In some other embodiments, the Aurora kinase inhibitor interacts with and reduces the activity of fewer than all Aurora kinase enzymes in the cell. In certain preferred embodiments, the Aurora kinase inhibitor selectively inhibits one Aurora kinase enzyme in the cell.

Preferably, the method according to this aspect of the invention causes an inhibition of cell proliferation of the contacted cells. The phrase "inhibiting cell proliferation" is used to denote an ability of an inhibitor of Aurora kinase to inhibit cell number or cell growth in contacted cells as compared to cells not contacted with the inhibitor. An assessment of cell proliferation can be made by counting cells using a cell counter or by an assay of cell viability, e.g., an MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an inhibitor of Aurora kinase that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth. For example, compounds of formula (VII), wherein Ring C is substituted with —$CO_2H$ may be formulated as the corresponding sodium salts.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to an Aurora kinase-mediated disorder. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer.

Preferably, the composition is formulated for administration to a patient having or at risk of developing or experiencing a recurrence of an Aurora kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. Preferably, such other therapeutic agent is one normally administered to patients with the disease or condition being treated.

By "therapeutically effective amount" is meant an amount sufficient to cause a detectable decrease in Aurora kinase activity or the severity of an Aurora kinase-mediated disorder. The amount of Aurora kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having or at risk of developing or experiencing a recurrence of an Aurora kinase-mediated disorder. The method comprises the step of administering to the patient a compound or pharmaceutical composition according to the invention. The compounds and pharmaceutical compositions of the invention can be used to achieve a beneficial therapeutic or prophylactic effect, for example, in a patient with a proliferative disorder, as discussed above. The compounds and pharmaceutical compositions of the invention are particularly useful for the treatment of cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition of the invention is used to treat a cancer in which the activity of an Aurora kinase is amplified. In some embodiments, the compound or composition of the invention is used to treat a patient having or at risk of developing or experiencing a recurrence in a cancer selected from the group consisting of colorectal cancer, ovarian cancer, breast cancer, gastric cancer, prostate cancer, and pancreatic cancer. In certain embodiments, the cancer is selected from the group consisting of breast cancer, colorectal cancer, and pancreatic cancer.

In some embodiments, the Aurora kinase inhibitor of the invention is administered in conjunction with another therapeutic agent. The other therapeutic agent may also inhibit Aurora kinase or may operate by a different mechanism. In some embodiments, the other therapeutic agent is one that is normally administered to patients with the disease or condition being treated. The Aurora kinase inhibitor of the invention may be administered with the other therapeutic agent in a single dosage form or as a separate dosage form. When administered as a separate dosage form, the other therapeutic agent may be administered prior to, at the same time as, or following administration of the Aurora kinase inhibitor of the invention.

In some embodiments, the Aurora kinase inhibitor of the invention is administered in conjunction with a therapeutic agent selected from the group consisting of cytotoxic agents, radiotherapy, and immunotherapy. Non-limiting examples of cytotoxic agents suitable for use in combination with the Aurora kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

In order that this invention be more fully understood, the following preparative and testing examples are set forth. These examples illustrate how to make or test specific compounds, and are not to be construed as limiting the scope of the invention in any way.

EXAMPLES

| Definitions | |
|---|---|
| AcOH | acetic acid |
| ATP | adenosine triphosphate |
| BSA | bovine serum albumin |
| Boc | tert-butoxycarbonyl |
| DMF | N,N-dimethylformamide |
| DTT | dithiothreitol |
| EDTA | ethylenediaminetetraacetic acid |
| EtOAc | ethyl acetate |
| Et$_2$O | diethyl ether |
| MeOH | methanol |
| MTT | methylthiazoletetrazolium |
| XTT | 2,3-bis(2-methoxy-4-nitro-5-sulfophenyl)-2H-tetrazolium-5-carboxanilide inner salt |
| WST | (4-[3-(4-iodophenyl)-2-(4-nitrophenyl)-2H-5-tetrazolio]-1,3-benzene disulfonate sodium salt |
| PKA | cAMP-dependent protein kinase |
| PPA | polyphosphoric acid |
| TBTU | O-Benzotriazol-1-yl-N,N,N',N'-tetramethyluronium tetrafluoroborate |
| THF | tetrahydrofuran |
| h | hours |
| min | minutes |
| m/z | mass to charge |
| MS | mass spectrum |
| HRMS | high resolution mass spectrum |

Example 1

4-{[9-chloro-7-(2,6-difluorophenyl)-5H-pyrido[3,4-d][2]benzazepin-2-yl]amino}-benzoic acid Step 1: Synthesis of tert-butyl[(6-chloropyridin-3-yl)methyl]carbamate

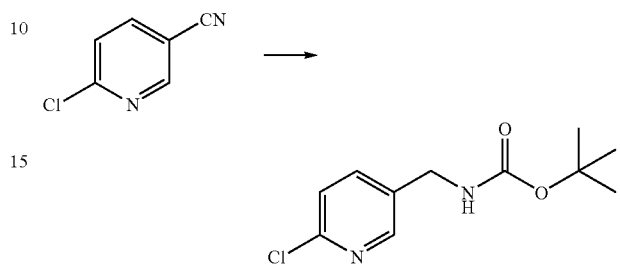

To a stirred solution of 6-chloronicotinonitrile (2.77 g, 0.02 mol) in methanol (150 mL), at 0° C., was added di-t-butyldicarbonate (8.73 g, 0.04 mol) and nickel (II) chloride hexahydrate (475 mg, 0.002 mol). Sodium borohydride (5.30 g, 0.14 mol) was then added in portions over 30 minutes. The resulting reaction mixture (containing a finely divided black precipitate) was allowed to warm to room temperature and left to stir for a further one hour. N-(2-aminoethyl)-1,2-ethanediamine (2.16 mL, 0.02 mol) was then added and the mixture was allowed to stir for 30 minutes. The reaction mixture was concentrated on a rotary evaporator. To the resulting purple residue were added ethyl acetate (200 mL) and a saturated sodium bicarbonate solution (200 mL). The mixture was transferred to a separatory funnel and the organic layer was extracted with additional saturated sodium bicarbonate (200 mL), dried over sodium sulfate, filtered and concentrated on a rotary evaporator. The resulting residue was dissolved in dichloromethane and purified by column chromatography on silica gel (elution gradient from dichloromethane to 15% ethyl acetate/dichloromethane) to yield tert-butyl[(6-chloropyridin-3-yl)methyl]carbamate as a white solid (3.30 g, 67% yield). The product structure was confirmed by NMR and MS.

Step 2: Synthesis of (5-{[(tert-butoxycarbonyl)amino]methyl}-2-chloropyridin-4yl)boronic acid

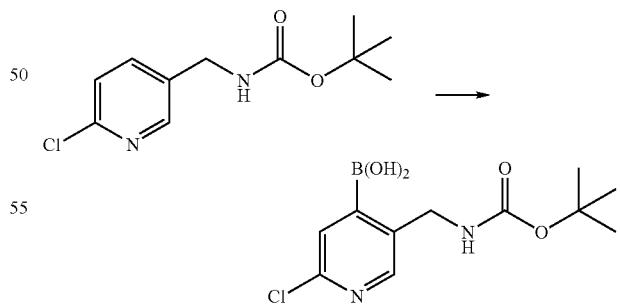

Tert-butyl[(6-chloropyridin-3-yl)methyl]carbamate (1.00 g, 0.004 mol) was dissolved in anhydrous tetrahydrofuran (20 mL) in an oven-dried 50-mL round-bottomed flask. The solution was stirred under an atmosphere of nitrogen and cooled to at −78° C. Tert-butyllithium (1.7 M in pentane, 5.1 mL, 0.009 mol) was slowly added via syringe. The reaction solution turned yellow, then dark orange during the addition. The resulting solution was stirred at −77° C. for 10 min, then was slowly warmed to −20° C. Triisopropyl borate (3.79 mL, 0.017 mol) was added quickly via syringe and the mixture was allowed to warm to room temperature with stirring. The reaction was cooled to 0° C. and quenched by the slow addition of 1.00 M of hydrochloric acid in water (8.65 mL) with good stirring. The reaction mixture was then added to water (100 mL) in a separatory funnel and was extracted with ethyl acetate (3×75 mL). The extracts were combined, dried over sodium sulfate, filtered, concentrated and dried under vacuum to leave 1.15 g (97% yield) (5-{[(tert-butoxy-carbonyl)amino]methyl}-2-chloropyridin-4yl)boronic acid as an orange foam. The product structure was confirmed by NMR and MS and used without further purification.

Step 3: Synthesis of tert-butyl({6-chloro-4-[4-chloro-2-(2,6-difluorobenzoyl)phenyl]pyridin-3-yl}methyl)carbamate

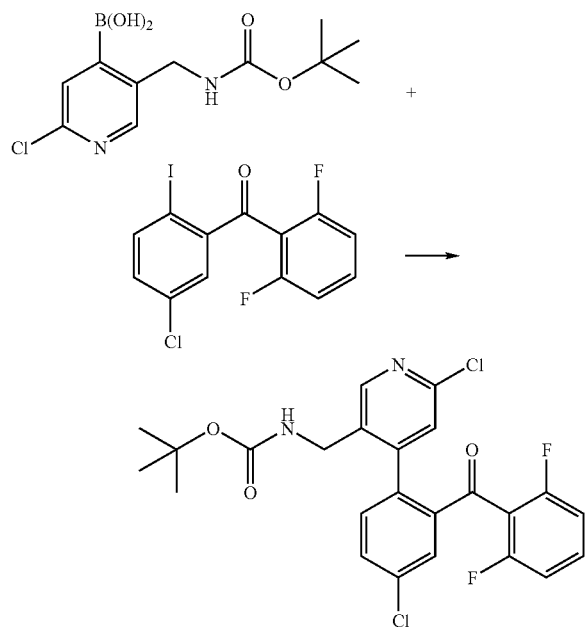

Into a 50-mL single-necked round-bottom flask was added 1,2-dimethoxy-ethane (10 mL). The solvent was purged with nitrogen, then tetrakis(triphenylphosphine)-palladium(0) (80.7 mg, 0.07 mmol) and (5-chloro-2-iodo-phenyl)-(2,6-difluoro-phenyl)-methanone (528 mg, 1.40 mmol) were added. The mixture was stirred under an atmosphere of nitrogen for 15 minutes, then (5-{[(tert-butoxycarbonyl)amino]methyl}-2-chloropyridin-4-yl)boronic acid (600.0 mg, 2.09 mmol) and 2.00 M sodium carbonate in water (1.40 mL) were added and the mixture was heated to reflux and allowed to stir 5 hours. The reaction was then cooled to room temperature and allowed to sit overnight. The reaction was diluted with methylene chloride (30 mL) and then transferred to a separatory funnel and was washed with water (2×30 mL). The organic portion was dried over sodium sulfate, filtered, and concentrated to provide the crude product as an orange oil. The crude product was purified by column chromatography on silica gel (elution gradient from dichloromethane to 15% ethyl acetate/dichloromethane) to yield 165 mg (24%) tert-butyl({6-chloro-4-[4-chloro-2-(2,6-difluorobenzoyl)phenyl] pyridin-3-yl}methyl)carbamate as an amber glass/solid. The product structure was confirmed by NMR and MS.

Step 4: Synthesis of 2,9-dichloro-7-(2,6-difluorophenyl)-5H-pyrido[3,4-][2]benzazepine

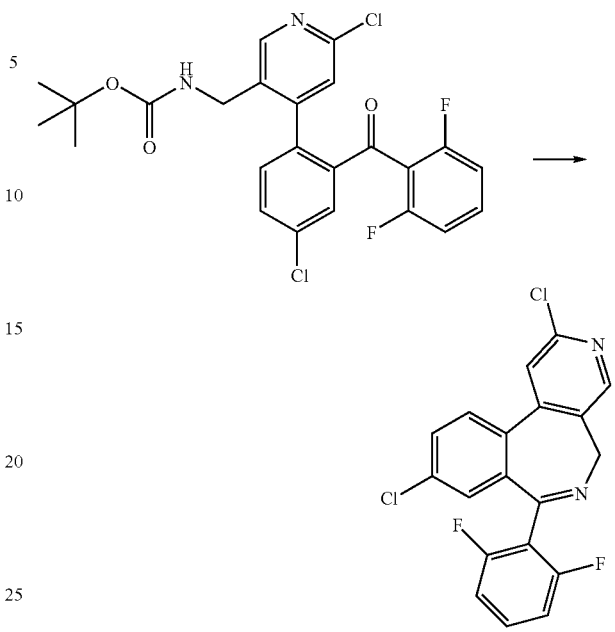

Tert-butyl({6-chloro-4-[4-chloro-2-(2,6-difluorobenzoyl)phenyl]pyridin-3-yl}-methyl)carbamate (165.0 mg, 0.3345 mmol) was dissolved in methylene chloride (5 mL). Trifluoroacetic acid (5 mL, 0.06 mol) was added and the reaction was stirred at room temperature under an atmosphere of nitrogen overnight. Water (20 mL) and methylene chloride (15 mL) were added and the resulting mixture was stirred while solid sodium carbonate (4.50 g, 0.04 mol) was slowly added with stirring. The resulting basic mixture was stirred at room temperature for 30 minutes and then transferred to a separatory funnel. The organic layer was separated and the aqueous phase was extracted with additional methylene chloride (10 mL). The organic extracts were combined, washed with water (10 mL) and brine (10 mL). The organic phase was dried over sodium sulfate, filtered and concentrated in vacuo. The resulting white solid was purified by column chromatography on silica gel (elution gradient from dichloromethane to 7.5% ethyl acetate/dichloromethane) to yield 2,9-dichloro-7-(2,6-difluorophenyl)-5H-pyrido[3,4-d][2]-benzazepine (108 mg, 86%) as a white solid. The product structure was confirmed by NMR and MS.

Step 5: Synthesis of ethyl 4-{[9-chloro-7-(2,6-difluorophenyl)-5H-pyrido[3,4d][2]-benzazepin-2-yl]amino}benzoate

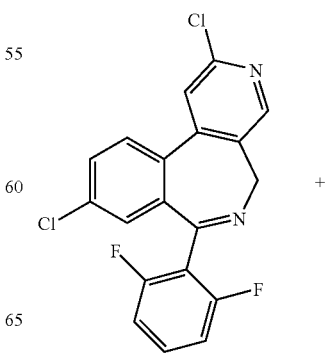 +

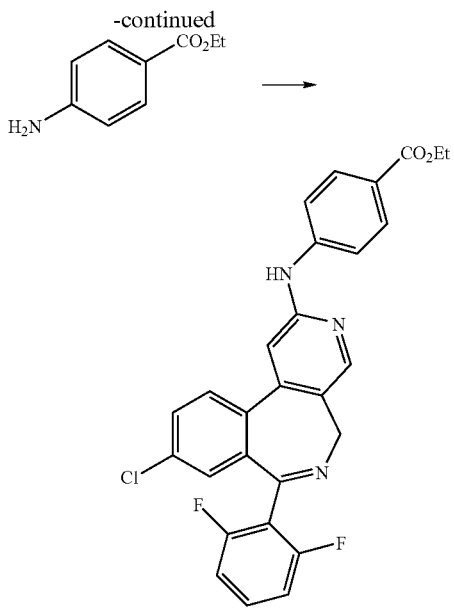

Toluene (3.5 mL) was added to 2,9-dichloro-7-(2,6-difluorophenyl)-5H-pyrido[3,4-d][2]benzazepine (69.0 mg, 0.18 mmol) and ethyl p-aminobenzoate (60.9 mg, 0.369 mmol), and the solution was stirred and sparged with nitrogen for 15 min. Tris(dibenzylideneacetone)dipalladium(0) (16.9 mg, 0.02 mol) and 2-dicyclohexylphosphino-2',4',6'-tri-i-propyl-1,1'-biphenyl (17.6 mg, 0.04 mmol) were added, followed by powdered cesium carbonate (179.8 mg, 0.55 mmol) and the reaction was stirred at 100° C. overnight. The reaction was cooled to room temperature and diluted with methylene chloride (5 mL). The mixture was filtered, concentrated and purified by column chromatography on silica gel (elution gradient from dichloromethane to 30% ethyl acetate/dichloromethane) to yield a yellow solid (32 mg, 34% yield).

Step 6: Synthesis of 4-{[9-chloro-7-(2,6-difluorophenyl)-5H-pyrido[3,4-d][2]benzazepin-2-yl]-amino}benzoic acid

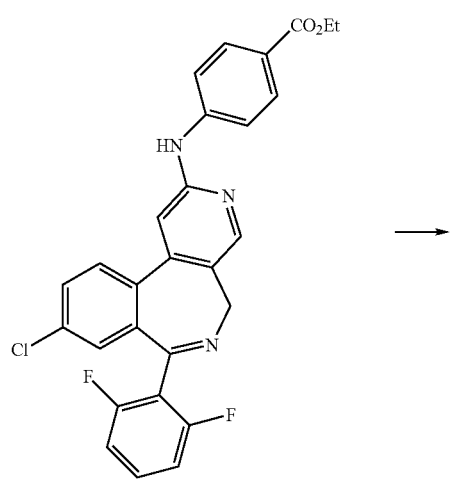

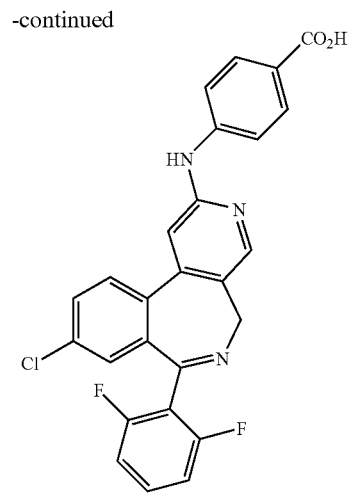

Ethyl 4-{[9-chloro-7-(2,6-difluorophenyl)-5H-pyrido[3,4-d][2]benzazepin-2-yl]amino}benzoate (30.0 mg, 0.06 mmol) was dissolved a mixture of methanol (1.0 mL) and tetrahydrofuran (2.0 mL) with stirring. 2.00 M lithium hydroxide in water (0.635 mL, 1.27 mmol) was added and the yellowish solution was stirred at room temperature under an atmosphere of nitrogen overnight. Water (50 mL) was added to the reaction solution with stirring, then 1N HCl was added dropwise to acidify the mixture to pH 2. The resulting precipitate was collected on a fritted funnel, washed with water and air-dried to yield 30 mg of a light orange powder. This crude product was purified by reverse phase chromatography to yield 4-{[9-chloro-7-(2,6-difluorophenyl)-5H-pyrido[3,4-d][2]benzazepin-2-yl]amino}benzoic acid (7.1 mg, 28% yield) as an off-white solid. The product structure was confirmed by NMR and MS.

Example 2

Expression and Purification of Aurora Kinase Enzymes

Aurora A Enzyme Expression and Purification

Recombinant mouse Aurora A with an amino-terminus hexahistidine tag (His-Aurora A) was expressed using a standard baculovirus vector and insect cell expression system (Bac-to-Bac®, Invitrogen).

Soluble, recombinant mouse Aurora A was purified from insect cells using Ni-NTA agarose (Qiagen) as described by the manufacturer and further purified over an S75 size exclusion column (Amersham Pharmacia Biotech).

Aurora B Enzyme Expression and Purification

Recombinant mouse Aurora B with an amino-terminus hexahistidine tag (His-Aurora B) was expressed using a standard baculovirus vector and insect cell expression system (Bac-to-Bac®, Invitrogen).

Soluble, recombinant mouse Aurora B was purified from insect cells using Ni-NTA agarose (Qiagen) as described by the manufacturer.

Example 3

Aurora Kinase Enzyme Assays

Aurora A DELFIA® Kinase Assay

The mouse Aurora A enzymatic reaction totaled 25 μL and contained 25 mM Tris-HCl (pH 8.5), 2.5 mM $MgCl_2$, 0.05%

Surfact-AMPS-20, 5 mM Sodium Fluoride, 5 mM DTT, 250 µM ATP, 10 µM peptide substrate (Biotin-β-Ala-QTRRK-STGGKAPR—NH$_2$), and 500 pM recombinant murine Aurora A enzyme. The enzymatic reaction mixture, with and without Aurora inhibitors, was incubated for 15 minutes at room temperature before termination with 100 µL of stop buffer (1% BSA, 0.05% Surfact-AMPS-20, and 100 mM EDTA). A total of 100 µL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 µL of antibody reaction mixture containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 µL of Enhancement Solution (Perkin Elmer). Quantification of europium was done using a Wallac™ EnVision (Perkin Elmer).

Aurora B DELFIA® Kinase Assay

The mouse Aurora B enzymatic reaction totaling 25 µL contained 25 mM Tris-HCl (pH 8.5), 2.5 mM MgCl$_2$, 0.025% Surfact-AMPS-20 (Pierce), 1% Glycerol, 1 mM DTT, 1 mM ATP, 3 µM peptide substrate (Biotin-β-Ala-QTRRKSTG-GKAPR—NH$_2$), and 20 nM recombinant murine Aurora B enzyme. The enzymatic reaction mixture, with or without Aurora inhibitors, was incubated for 3 hours at room temperature before termination with 100 µL of stop buffer (1% BSA, 0.05% Surfact-AMPS-20, and 100 mM EDTA). A total of 100 µL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 µL of antibody reaction mix containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 µL of Enhancement Solution (Perkin Elmer). Quantification of europium was done using a Wallac™ EnVision (Perkin Elmer).

Example 4

Cellular Assay

Aurora Phosphorylation Assays

Inhibition of Aurora A or Aurora B activity in whole cell systems can be assessed by determination of decreased phosphorylation of Aurora substrates. For example, determining decreased phosphorylation of histone H3 on Serine 10, an Aurora B substrate can be used to measure inhibition of Aurora B activity in a whole cell system. Alternatively, any known Aurora B substrate can be used in similar assay methods to assess inhibition of Aurora B activity. Similarly, Aurora A inhibition can be determined using analogous methods and known Aurora A substrates for detection.

In a specific example, HeLa cells are seeded in a 96-well cell culture plate ($10 \times 10^3$ cells/well) and incubated overnight at 37° C. Cells are incubated with Aurora inhibitors for 1 hour at 37° C., fixed with 4% paraformaldehyde for 10 minutes and then permeabilized with 0.5% TritonX-100 in PBS. Cells are incubated with mouse anti-pHisH3 (1:120, Cell Signaling Technologies) and rabbit anti-mitotic marker (1:120, Millennium Pharmaceuticals Inc.) antibodies for 1 hour at room temperature. After washing with PBS the cells are stained with anti-rabbit IgG Alexa 488 (1:180, Molecular Probes) and anti-mouse IgG Alexa 594 (1:180) for 1 hour at room temperature. DNA is then stained with Hoechst solution (2 µg/mL). The percentage of pHisH3 and anti-mitotic positive cells is quantified using Discovery I and MetaMorph (Universal Imaging Corp.). Aurora B inhibition is determined by calculating the decrease of pHisH3 positive cells.

Anti-Proliferation Assays

HCT-116 (1000) or other tumor cells in 100 µL of appropriate cell culture medium (McCoy's 5A for HCT-116, Invitrogen) supplemented with 10% fetal bovine serum (Invitrogen) are seeded in wells of a 96-well cell culture plate and incubated overnight at 37° C. Aurora inhibitors are added to the wells and the plates are incubated for 96 hours at 37° C. MIT or WST reagent (10 µL, Roche) is added to each well and incubated for 4 hours at 37° C. as described by the manufacturer. For MTT the metabolized dye is solubized overnight according to manufacturer's instructions (Roche). The optical density for each well is read at 595 nm (primary) and 690 nm (reference) for the MTT and 450 nm for the WST using a spectrophotometer (Molecular Devices). For the MTT the reference optical density values are subtracted from the values of the primary wavelength. Percent inhibition is calculated using the values from a DMSO control set to 100%.

Example 5

In vivo Assays

In vivo Tumor Efficacy Model

HCT-116 ($1 \times 10^6$) or other tumor cells in 100 µL of phosphate buffered saline are aseptically injected into the subcutaneous space in the right dorsal flank of female CD-1 nude mice (age 5-8 weeks, Charles River) using a 23-ga needle. Beginning at day 7 after inoculation tumors are measured twice weekly using a vernier caliper. Tumor volumes are calculated using standard procedures ($0.5 \times (\text{length} \times \text{width}^2)$). When the tumors reach a volume of approximately 200 mm$^3$ mice are injected i.v. in the tail vein with Aurora kinase inhibitors (100 µL) at various doses and schedules. All control groups receive vehicle alone. Tumor size and body weight are measured twice a week and the study is terminated when the control tumors reach approximately 2000 mm$^3$.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A compound of formula (I):

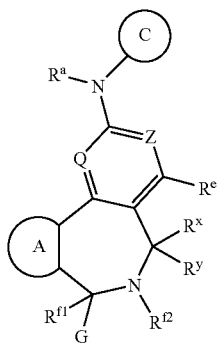

(I)

or a pharmaceutically acceptable salt thereof;
wherein:
$R^{f1}$ is hydrogen, or $R^{f1}$ and $R^{f2}$ together form a bond;
$R^{f2}$ is hydrogen, or $R^{f2}$ forms a bond with either $R^{f1}$ or $R^x$;
$R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring; or $R^x$ and $R^{f2}$ together form a bond;
one of Q and Z is —N—, and the other is —CH—;
G is hydrogen, an optionally substituted aliphatic or Ring B when $R^{f1}$ is hydrogen; and G is hydrogen, —$OR^5$, —$N(R^4)_2$, —$SR^5$, an optionally substituted aliphatic, or Ring B when $R^{f1}$ and $R^2$ together form a bond;
Ring A is a substituted or unsubstituted 5- or 6-membered aryl, heteroaryl, cycloaliphatic, or heterocyclyl ring;
Ring B is a substituted or unsubstituted aryl, heteroaryl, heterocyclyl, or cycloaliphatic ring;
Ring C is a substituted or unsubstituted aryl, heteroaryl, heterocyclyl, or cycloaliphatic ring;
$R^a$ is hydrogen, —$C(O)R^1$, —$CO_2R^1$, —$SO_2R^1$, or a $C_{1-3}$ aliphatic having 0-2 substituents independently selected from $R^3$ or $R^7$;
$R^e$ is hydrogen, —$OR^5$, —$N(R^4)_2$, —$SR^5$, —$NR^4C(O)R^5$, —$NR^4C(O)N(R^4)_2$, —$NR^4CO_2R^6$, —$N(R^4)SO_2R^6$, —$N(R^4)SO_2N(R^4)_2$, or a $C_{1-3}$ aliphatic optionally substituted with $R^3$ or $R^7$;
$R^1$ is $C_{1-6}$ aliphatic or an optionally substituted aryl, heteroaryl, or heterocyclyl group;
each $R^3$ independently is selected from the group consisting of -halo, —OH, —$O(C_{1-3}$ alkyl), —CN, —$N(R^4)_2$, —$C(O)(C_{1-3}$ alkyl), —$CO_2H$, —$CO_2(C_{1-3}$ alkyl), —$C(O)NH_2$, and —$C(O)NH(C_{1-3}$ alkyl);
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;
each $R^5$ independently is hydrogen or an optionally substituted aliphatic, aryl, heteroaryl, or heterocyclyl group;
each $R^6$ independently is an optionally substituted aliphatic or aryl group; and
each $R^7$ independently is an optionally substituted aryl, heterocyclyl, or heteroaryl group.

2. The compound of claim 1, wherein:
$R^x$ and $R^y$ are each independently selected from hydrogen, fluoro, or a $C_{1-6}$ aliphatic optionally substituted with one or two $R^3$; or $R^x$ and $R^y$, taken together with the carbon atom to which they are attached, form an optionally substituted 3- to 6-membered cycloaliphatic ring;
$R^e$ is hydrogen, —OH, —$NHR^4$, —SH, or a $C_{1-3}$ aliphatic optionally substituted with $R^3$ or $R^7$;
$R^{f1}$ and $R^{f2}$ together form a bond;
G is —H, —OH, —$NH_2$, —$O(C_{1-3}$ alkyl), —$NH(C_{1-3}$ alkyl), —$N(C_{1-3}$ alkyl$)_2$, $C_{1-3}$ alkyl, or $C_{1-3}$ fluoroalkyl; or has a formula selected from the group consisting of —O-$L^1$-$R^7$, —$N(C_{1-3}$ alkyl)-$L^1$-$R^7$, and -$L^1$-$R^7$; and
$L^1$ is a covalent bond or $C_{1-3}$ alkylene.

3. The compound of claim 1, having formula (II):

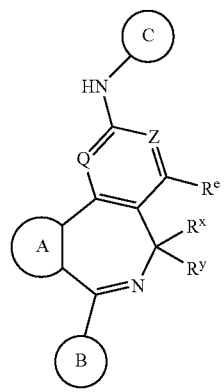

(II)

or a pharmaceutically acceptable salt thereof.

4. The compound of claim 3, wherein Ring A is a substituted or unsubstituted ring selected from the group consisting of furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridinio, piperidino, dioxano, morpholino, dithiano, thiomorpholino, pyridazino, pyrimidino, pyrazino, piperazino, and triazino.

5. The compound of claim 4 wherein Ring A is a substituted or unsubstituted ring selected from the group consisting of furano, thieno, pyrrolo, oxazolo, thiazolo, imidazolo, pyrazolo, isoxazolo, isothiazolo, triazolo, benzo, pyridino, pyridazino, pyrimidino, and pyrazino.

6. A compound of formula (II):

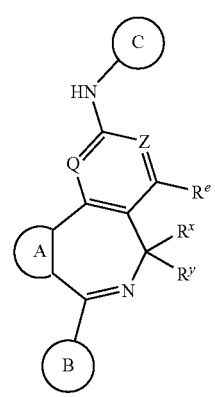

(II)

or a pharmaceutically acceptable salt thereof;

81 wherein:
   $R^e$ is hydrogen, $-OR^5$, $-N(R^4)_2$, $-SR^5$, $-NR^4C(O)R^5$, $-NR^4C(O)N(R^4)_2$, $-NR^4CO_2R^6$, $-N(R^4)SO_2R^6$, $-N(R^4)SO_2N(R^4)_2$, or a $C_{1-3}$ aliphatic optionally substituted with $R^3$ or $R^7$;
   $R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;
   one of Q and Z is —N—, and the other is —CH—;
   Ring A is a substituted or unsubstituted ring selected from the group consisting of furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino;
   each substitutable saturated ring carbon atom in Ring A is unsubstituted or substituted with =O, =S, =C($R^5$)$_2$, =N—N($R^4$)$_2$, =N—OR$^5$, =N—NHC(O)R$^5$, =N—NHCO$_2$R$^6$, =N—NHSO$_2$R$^6$, =N—R$^5$ or —R$^b$;
   each substitutable unsaturated ring carbon atom in Ring A is unsubstituted or substituted with —R$^b$;
   each substitutable ring nitrogen atom in Ring A is unsubstituted or substituted with —R$^{9b}$;
   one ring nitrogen atom in Ring A optionally is oxidized;
   each $R^b$ independently is -halo, —NO$_2$, —CN, —C($R^5$)=C($R^5$)$_2$, —C($R^5$)=C($R^5$)($R^{10}$), —C≡C—R$^5$, —C≡C—R$^{10}$, —OR$^5$, —SR$^6$, —S(O)R$^6$, —SO$_2$R$^6$, —SO$_2$N($R^4$)$_2$, —N($R^4$)$_2$, —NR$^4$C(O)R$^5$, —NR$^4$C(O)N($R^4$)$_2$, —NR$^4$CO$_2$R$^6$, —O—CO$_2$R$^5$, —OC(O)N($R^4$)$_2$, —O—C(O)R$^5$, —CO$_2$R$^5$, —C(O)—C(O)R$^5$, —C(O)R$^5$, —C(O)N($R^4$)$_2$, —C(=NR$^4$)—N($R^4$)$_2$, —C(=NR$^4$)—OR$^5$, —N($R^4$)—N($R^4$)$_2$, N($R^4$)C(=NR$^4$)—N($R^4$)$_2$, —N($R^4$)SO$_2$R$^6$, —N($R^4$)SO$_2$N($R^4$)$_2$, —P(O)(R$^5$)$_2$, —P(O)(OR$^5$)$_2$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S;
   Ring B is a substituted or unsubstituted aryl, heteroaryl, heterocyclyl, or cycloaliphatic ring;
   Ring C is a substituted or unsubstituted aryl, heteroaryl, heterocyclyl, or cycloaliphatic ring;
   each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl);
   each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl having, in addition to the nitrogen atom, 0-2 ring heteroatoms selected from N, O, and S;
   each $R^5$ independently is hydrogen or an optionally substituted aliphatic, aryl, heteroaryl, or heterocyclyl group;
   each $R^6$ independently is an optionally substituted aliphatic or aryl group;
   each $R^7$ independently is an optionally substituted aryl, heterocyclyl, or heteroaryl group;

each $R^{9b}$ independently is —C(O)R$^5$, —C(O)N($R^4$)$_2$, —CO$_2$R$^6$, —SO$_2$R$^6$, —SO$_2$N($R^4$)$_2$, or a $C_{1-4}$ aliphatic optionally substituted with $R^3$ or $R^7$; and
each $R^{10}$ independently is —CO$_2$R$^5$ or —C(O)N($R^4$)$_2$.

7. A compound of formula (II):

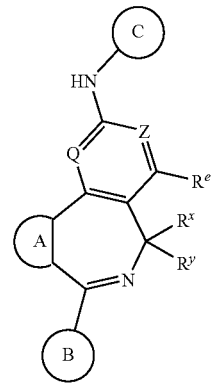

(II)

or a pharmaceutically acceptable salt thereof;
wherein:
   $R^e$ is hydrogen, $-OR^5$, $-N(R^4)_2$, $-SR^5$, $-NR^4C(O)R^5$, $-NR^4C(O)N(R^4)_2$, $-NR^4CO_2R^6$, $-N(R^4)SO_2R^6$, $-N(R^4)SO_2N(R^4)_2$, or a $C_{1-3}$ aliphatic optionally substituted with $R^3$ or $R^7$;
   $R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;
   one of Q and Z is —N—, and the other is —CH—;
   Ring A is a substituted or unsubstituted ring selected from the group consisting of furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino;
   each substitutable saturated ring carbon atom in Ring A is unsubstituted or substituted with =O, =S, =C($R^5$)$_2$, =N—N($R^4$)$_2$, =N—OR$^5$, =N—NHC(O)R$^5$, =N—NHCO$_2$R$^6$, =N—NHSO$_2$R$^6$, =N—R$^5$ or —R$^b$;
   each substitutable unsaturated ring carbon atom in Ring A is unsubstituted or substituted with —R$^b$;
   each substitutable ring nitrogen atom in Ring A is unsubstituted or substituted with —R$^{9b}$;
   one ring nitrogen atom in Ring A optionally is oxidized;
   each $R^b$ independently is selected from the group consisting of $C_{1-6}$ aliphatic, $C_{1-6}$ fluoroaliphatic, —R$^{2b}$, —R$^{7b}$, -T$^1$-R$^{2b}$, and -T$^1$-R$^{7b}$; or two adjacent $R^b$, taken together with the intervening ring atoms, form an optionally substituted fused 4- to 8-membered aromatic or non-aromatic ring having 0-3 ring heteroatoms selected from the group consisting of O, N, and S;
   $T^1$ is a $C_{1-6}$ alkylene chain optionally substituted with $R^3$ or $R^{3b}$, wherein $T^1$ or a portion thereof optionally forms part of a 3- to 7-membered ring;
   each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;

each $R^{2b}$ independently is halo, —$NO_2$, —CN, —C($R^5$)=C($R^5$)$_2$, —C($R^5$)=C($R^5$)($R^{10}$), —C≡C—$R^5$, —C≡C—$R^{10}$, —O$R^5$, —S$R^6$, —S(O)$R^6$, —$SO_2R^6$, —$SO_2$N($R^4$)$_2$, —N($R^4$)$_2$, —$NR^4$C(O)$R^5$, —$NR^4$C(O)N($R^4$)$_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—O$R^5$, —N($R^4$)—N($R^4$)$_2$, —N($R^4$)C(=$NR^4$)—N($R^4$)$_2$, —N($R^4$)$SO_2R^6$, —N($R^4SO_2$N($R^4$)$_2$, —P(O)($R^5$)$_2$, or —P(O)(OR)$^5$)$_2$; and each $R^{7b}$ independently is an optionally substituted aryl, heteroaryl, or heterocyclyl group;

each $R^{9b}$ independently is —C(O)$R^5$, —C(O)N($R^4$)$_2$, —$CO_2R^6$, —$SO_2R^6$, —$SO_2$N($R^4$)$_2$, or a $C_{1-4}$ aliphatic optionally substituted with $R^3$ or $R^7$;

Ring B is a substituted or unsubstituted aryl, heteroaryl, heterocyclyl, or cycloaliphatic ring;

Ring C is a substituted or unsubstituted aryl, heteroaryl, heterocyclyl, or cycloaliphatic ring;

each $R^3$ independently is selected from the group consisting of -halo, —OH, —O($C_{1-3}$ alkyl), —CN, —N($R^4$)$_2$, —C(O)($C_{1-3}$ alkyl), —$CO_2$H, —$CO_2$($C_{1-3}$ alkyl), —C(O)$NH_2$, and —C(O)NH($C_{1-3}$ alkyl);

each $R^4$ independently is hydrogen or an optionally substituted aliphatic, aryl, heteroaryl, or heterocyclyl group; or two $R^4$ on the Same nitrogen atom, taken together with the nitrogen atom, form an optionally substituted 5- to 6-membered heteroaryl or 4- to 8-membered heterocyclyl having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group;

each $R^7$ independently is an optionally substituted aryl, heterocyclyl, or heteroaryl group; and each $R^{10}$ independently is —$CO_2R^5$ or —C(O)N($R^4$)$_2$.

8. The compound of claim 7, wherein Ring A is selected from the group consisting of:

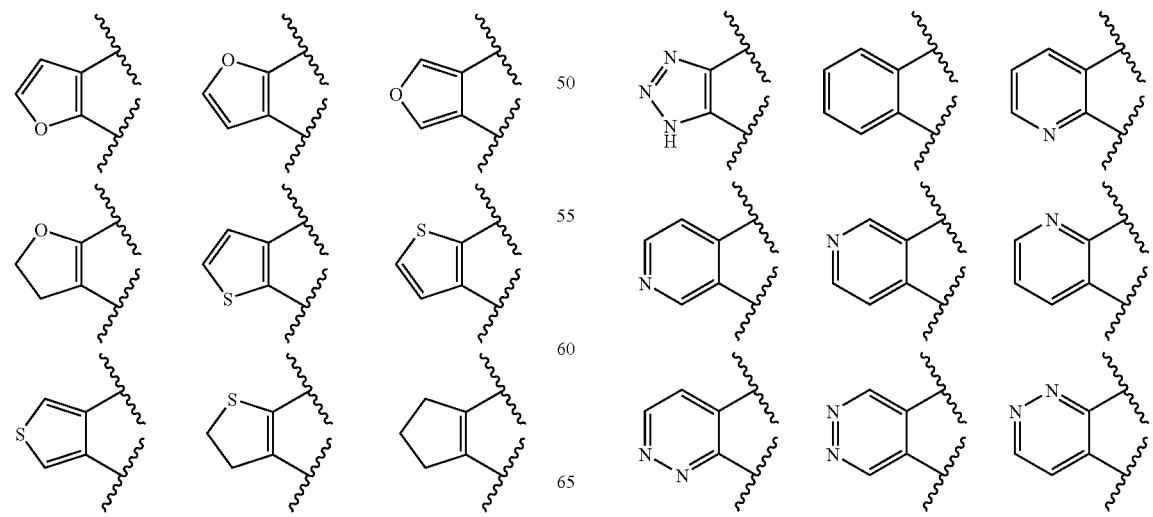

-continued

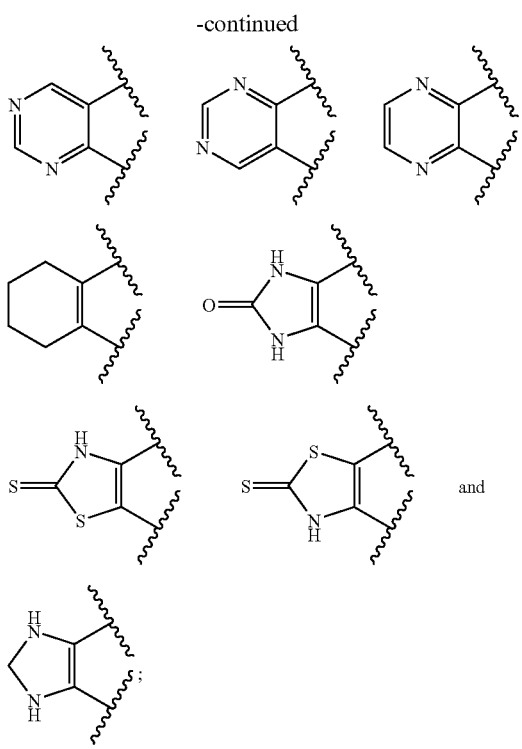

any of which groups optionally is substituted on any substitutable ring carbon atom and any substitutable ring nitrogen atom.

9. The compound of claim 8, wherein Ring A is selected from the group consisting of:

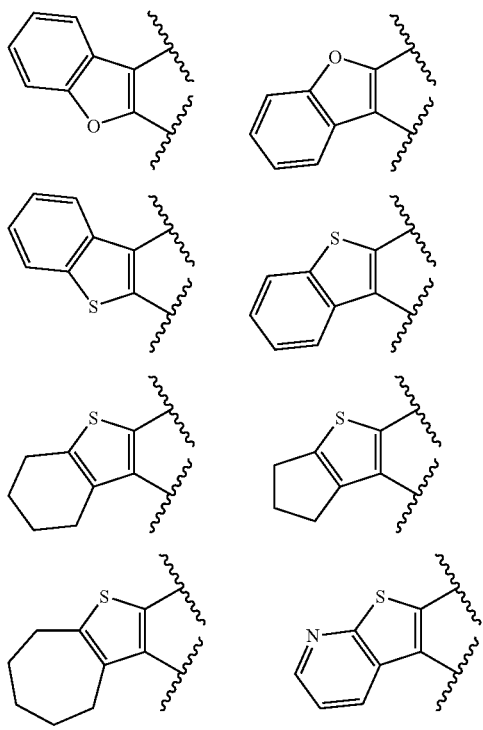

-continued

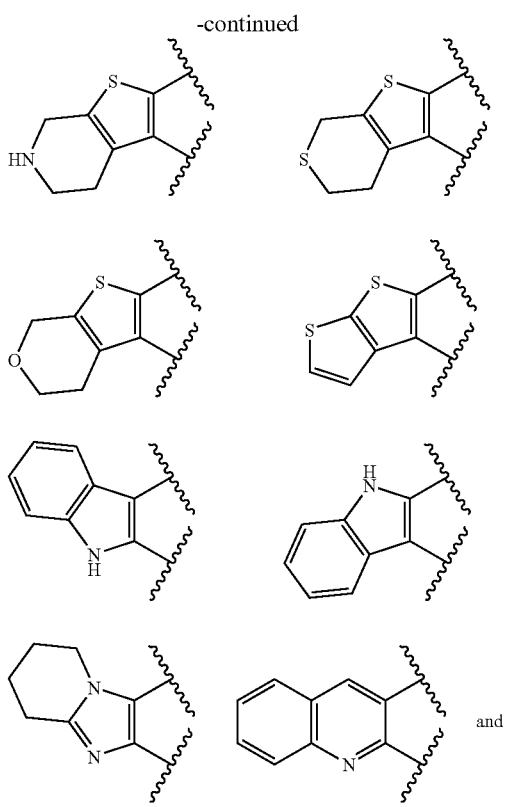

any of which groups optionally is substituted on any substitutable ring carbon atom and any substitutable ring nitrogen atom.

10. The compound of claim 8, having formula (III):

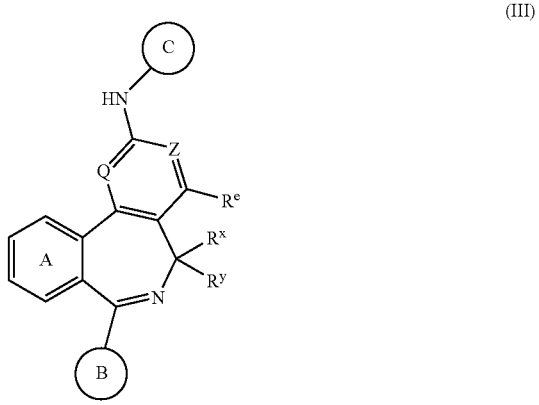

or a pharmaceutically acceptable salt thereof, wherein Ring A is substituted with 0-3 $R^b$.

11. A compound of formula (III):

$$\text{(III)}$$

[Chemical structure showing rings A, B, C with substituents HN-C attached to Q-Z position, R^e, R^x, R^y on a fused ring system with N]

or a pharmaceutically acceptable salt thereof;
wherein:
$R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;
one of Q and Z is —N—, and the other is —CH—;
$R^e$ is hydrogen, —$OR^5$, —$N(R^4)_2$, —$SR^5$, —$NR^4C(O)R^5$, —$NR^4C(O)N(R^4)_2$, —$NR^4CO_2R^6$, —$N(R^4)SO_2R^6$, —$N(R^4)SO_2N(R^4)_2$, or a $C_{1-3}$ aliphatic optionally substituted with $R^3$ or $R^7$;
Ring A is substituted with 0-3 $R^b$;
each $R^b$ independently is selected from the group consisting of $C_{1-6}$ aliphatic, $C_{1-6}$ fluoroaliphatic, —$R^{2b}$, —$R^{7b}$, -$T^1$-$R^{2b}$, and -$T^1$-$R^{7b}$; or two adjacent $R^b$, taken together with the intervening ring atoms, form an optionally substituted fused 4- to 8-membered aromatic or non-aromatic ring having 0-3 ring heteroatoms selected from the group consisting of O, N, and S;
$T^1$ is a $C_{1-6}$ alkylene chain optionally substituted with $R^3$ or $R^{3b}$, wherein $T^1$ or a portion thereof optionally forms part of a 3- to 7-membered ring;
each $R^{2b}$ independently is halo, —$NO_2$, —CN, —$C(R^5)$=$C(R^5)_2$, —$C(R^5)$=$C(R^5)(R^{10})$, —C≡C—$R^5$, —C≡C—$R^{10}$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —$OC(O)N(R^4)_2$, —O—$C(O)R^5$, —$CO_2R^5$, —C(O)—$C(O)R^5$, —$C(O)R^5$, —$C(O)N(R^4)_2$, —C(=$NR^4$)—$N(R^4)_2$, —C(=$NR^4$)—$OR^5$, —$N(R^4)$—$N(R^4)_2$, —$N(R^4)C$(=$NR^4$)—$N(R^4)_2$, —$N(R^4)SO_2R^6$, —$N(R^4)SO_2N(R^4)_2$, —$P(O)(R^5)_2$, or —$P(O)(OR^5)_2$; and
each $R^{7b}$ independently is an optionally substituted aryl, heteroaryl, or heterocyclyl group;
Ring B is a mono- or bicyclic aryl heteroaryl, heterocyclyl, or cycloaliphatic ring;
each substitutable saturated ring carbon atom in Ring B is unsubstituted or is substituted with =O, =S, =$C(R^5)_2$, or $R^c$;
each substitutable unsaturated ring carbon atom in Ring B is unsubstituted or is substituted with $R^c$;
each substitutable ring nitrogen atom in Ring B is unsubstituted or substituted with $R^{9c}$;
each $R^c$ independently is selected from the group consisting of $C_{1-6}$ aliphatic, $R^{2c}$, $R^{7c}$, -$T^1$-$R^{2c}$, and -$T^1$-$R^{7c}$;

$T^1$ is a $C_{1-6}$ alkylene chain optionally substituted with $R^3$ or $R^{3b}$, wherein $T^1$ or a portion thereof optionally forms part of a 3- to 7-membered ring;
$R^{2c}$ is -halo, —$NO_2$, —CN, —$C(R^5)$=$C(R^5)_2$, —$C(R^5)$=$C(R^5)(R^{10})$, —C≡C—$R^5$, —C≡C—$R^{10}$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —$OC(O)N(R^4)_2$, —O—$C(O)R^5$, —$CO_2R^5$, —C(O)—$C(O)R^5$, —$C(O)R^5$, —$C(O)N(R^4)_2$, —C(=$NR^4$)—$N(R^4)_2$, —C(=$NR^4$)—$OR^5$, —$N(R^4)$—$N(R^4)_2$, —$N(R^4)C$(=$NR^4$)—$N(R^4)_2$, —$N(R^4)SO_2R^6$, —$N(R^4)SO_2N(R^4)_2$, —$P(O)(R^5)_2$, or —$P(O)(OR^5)_2$;
each $R^{7c}$ independently is an optionally substituted aryl, heterocyclyl, or heteroaryl group;
each $R^{9c}$ independently is —$C(O)R^5$, —$C(O)N(R^4)_2$, —$CO_2R^6$, —$SO_2R^6$, —$SO_2N(R^4)_2$, or a $C_{1-4}$ aliphatic optionally substituted with $R^3$ or $R^7$; and
Ring C is a mono- or bicyclic aryl, heteroaryl, heterocyclyl, or cycloaliphatic ring;
each substitutable saturated ring carbon atom in Ring C is unsubstituted or is substituted with =O, =S, =$C(R^5)_2$, or $R^d$;
each substitutable unsaturated ring carbon atom in Ring C is unsubstituted or is substituted with $R^d$;
each substitutable ring nitrogen atom in Ring C is unsubstituted or is substituted with $R^{9d}$;
each $R^d$ independently is selected from the group consisting of $C_{1-6}$ aliphatic, $R^{2d}$, $R^{7d}$, -$T^2$-$R^{2d}$, -$T^2R^{7d}$, —V-$T^3$-$R^{2d}$, and —V-$T^3$-$R^{7d}$;
$T^2$ is a $C_{1-6}$ alkylene chain optionally substituted with $R^3$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$N(R^4)$—$N(R^4)$—, —$N(R^4)SO_2$—, or —$SO_2N(R^4)$—, and wherein $T^2$ or a portion thereof optionally forms part of a 3-7 membered ring;
$T^3$ is a $C_{1-6}$ alkylene chain optionally substituted with $R^3$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$N(R^4)$—$N(R^4)$—, —$N(R^4)SO_2$—, or —$SO_2N(R^4)$—, and wherein $T^3$ or a portion thereof optionally forms part of a 3-7 membered ring;
V is a —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —$OC(O)N(R^4)$—, —$C(NR^4)$=N—, —$C(OR^5)$=N—, —$N(R^4)$—$N(R^4)$—, —$N(R^4)SO_2$—, —$N(R^4)SO_2N(R^4)$—, —$P(O)(R^5)$—, —$P(O)(OR^5)$—O—, —P(O)—O—, or —$P(O)(NR^5)$—$N(R^{5})$—;
$R^{2d}$ is -halo, —$NO_2$, —CN, —$C(R^5)$=$C(R^5)_2$, —$C(R^5)$=$C(R^5)(R^{10})$, —C≡C—$R^5$, —C≡C—$R^{10}$, —$OR^5$, —$SR^6$, —$S(O)R^6$, —$SO_2R^6$, —$SO_3R^5$, —$SO_2N(R^4)_2$, —$N(R^4)_2$, —$NR^4C(O)R^5$, —$NR^4C(O)N(R^4)_2$, —$NR^4CO_2R^6$, —O—$C(O)R^5$, —O—$CO_2R^5$, —$OC(O)N(R^4)_2$, —O—$C(O)R^5$, —$CO_2R^5$, —C(O)—$C(O)R^5$, —$C(O)R^5$, —$C(O)N(R^4)_2$, —$C(O)N(R^4)C$(=$NR^4$)—$N(R^4)_2$, —$N(R^4)C$(=$NR^4$)—$N(R^4)$—$C(O)R^5$, —C(=$NR^4$)—

$N(R^4)_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$;

each $R^{7d}$ independently is an optionally substituted aryl, heterocyclyl, or heteroaryl group;

each $R^{9d}$ independently is —C(O)R$^5$, —C(O)N(R$^4$)$_2$, —CO$_2$R$^6$, —SO$_2$R$^6$, —SO$_2$N(R$^4$)$_2$, or a C$_{1-4}$ aliphatic optionally substituted with R$^3$ or R$^7$;

each $R^3$ independently is selected from the group consisting of -halo, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, and —C(O)NH(C$_{1-3}$ alkyl);

each $R^{3b}$ independently is a C$_{1-3}$ aliphatic optionally substituted with R$^3$ or R$^7$, or two substituents R$^{3b}$ on the same carbon atom, taken together with the carbon atom to which they are attached, form a 3- to 6-membered carbocyclic ring;

each $R^4$ independently is hydrogen or an optionally substituted aliphatic, aryl, heteroaryl, or heterocyclyl group; or two R$^4$ on the same nitrogen atom, taken together with the nitrogen atom, form an optionally substituted 5- to 6-membered heteroaryl or 4- to 8-membered heterocyclyl having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group;

each $R^7$ independently is an optionally substituted aryl, heterocyclyl, or heteroaryl group; and each $R^{10}$ independently is —CO$_2$R$^5$ or —C(O)N(R$^4$)$_2$.

12. The compound of claim 11, wherein Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl benzthiazolyl, benzoxazolyl, purinyl, quinolyl, isoquinolyl, cinnolinyl, phthalazinyl, quinazolinyl, quinoxalinyl, naphthyridinyl, and pteridinyl.

13. The compound of claim 12, wherein Ring B is a substituted or unsubstituted phenyl or pyridyl ring.

14. The compound of claim 13, having formula (IV):

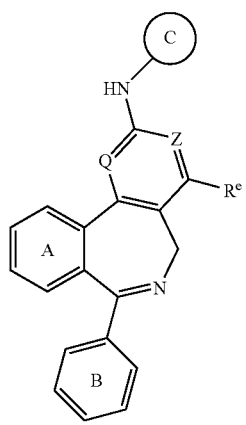

(IV)

wherein:
Ring A is substituted with 0-2 independently selected R$^b$; and
Ring B is substituted with 0-2 independently selected R$^c$.

15. The compound of claim 14, characterized by at least one of the following features:
(a) each R$^b$ independently is selected from the group consisting of C$_{1-3}$ aliphatic, R$^{2b}$, R$^{7b}$, -T$^1$-R$^{2b}$, and -T$^1$-R$^{7b}$, where T$^1$ is a C$_{1-3}$ alkylene chain optionally substituted with fluoro, and each R$^{2b}$ independently is selected from the group consisting of -halo, —NO$_2$, —C(R$^5$)=C(R$^5$)$_2$, —C≡C—R$^5$, —OR$^5$, —N(R$^4$)$_2$, —CO$_2$R$^5$, and —C(O)N(R$^4$)$_2$;
(b) each R$^c$ independently is selected from the group consisting of C$_{1-3}$ aliphatic, R$^{2c}$, R$^{7c}$, -T$^1$-R$^{2c}$, and -T$^1$-R$^{7c}$, where T$^1$ is a C$_{1-3}$ alkylene chain optionally substituted with fluoro, and each R$^{2c}$ independently is selected from the group consisting of -halo, —NO$_2$, —C(R$^5$)=C(R$^5$)$_2$, —C≡C—R$^5$, —OR$^5$, and —N(R$^4$)$_2$; and
(c) R$^e$ is hydrogen.

16. A compound of formula (V):

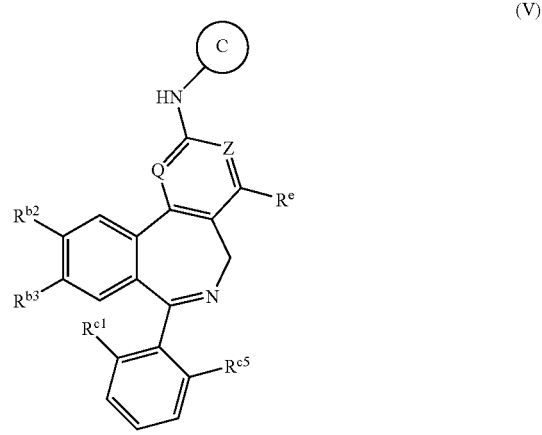

(V)

or a pharmaceutically acceptable salt thereof;
wherein:
one of Q and Z is —N—, and the other is —CH—;
R$^e$ is hydrogen, —OR$^5$, —N(R$^4$)$_2$, —SR$^5$, —NR$^4$C(O)R$^5$, —NR$^4$C(O)N(R$^4$)$_2$, —NR$^4$CO$_2$R$^6$, —N(R$^4$)SO$_2$R$^6$, —N(R$^4$)SO$_2$N(R$^4$)$_2$, or a C$_{1-3}$ aliphatic optionally substituted with R$^3$ or R$^7$;
R$^{b2}$ and R$^{b3}$ are each independently hydrogen or R$^b$;
R$^b$ is selected from the group consisting of C$_{1-3}$ aliphatic, C$_{1-3}$ fluoroaliphatic, and R$^{2b}$;
R$^{2b}$ is selected from the group consisting of -halo, —NO$_2$, —C(R$^5$)=C(R$^5$)$_2$, —C≡C—R$^5$, —OR$^5$, —N(R$^4$)$_2$, —CO$_2$R$^5$, —C(O)N(R$^4$)$_2$;
R$^{c1}$ and R$^{c5}$ are each independently hydrogen or R$^c$;
R$^c$ is selected from the group consisting of C$_{1-3}$ aliphatic, C$_{1-3}$ fluoroaliphatic, and R$^{2c}$;
R$^{2c}$ is selected from the group consisting of -halo, —NO$_2$, —C(R$^5$)=C(R$^5$)$_2$, —C≡C—R$^5$, —OR$^5$, and —N(R$^4$)$_2$;
Ring C is a mono- or bicyclic aryl, heteroaryl, heterocyclyl, or cycloaliphatic ring;
each substitutable saturated ring carbon atom in Ring C is unsubstituted or is substituted with =O, =S, =C(R$^5$)$_2$, or R$^d$;
each substitutable unsaturated ring carbon atom in Ring C is unsubstituted or is substituted with R$^d$;
each substitutable ring nitrogen atom in Ring C is unsubstituted or is substituted with R$^{9d}$;

each $R^d$ independently is selected from the group consisting of $C_{1-6}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$;

$T^2$ is a $C_{1-6}$ alkylene chain optionally substituted with $R^3$ or $R^{3b}$, wherein the alkylene chain optionally is interrupted by —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —NR$^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —N($R^4$)—N($R^4$)—, —N($R^4$)SO$_2$—, or —SO$_2$N($R^4$)—, and wherein $T^2$ or a portion thereof optionally forms part of a 3-7 membered ring;

$T^3$ is a $C_{1-6}$ alkylene chain optionally substituted with $R^3$ or $R^{3b}$, where the alkylene chain optionally is interrupted by —C($R^5$)=C($R^5$)—, —C≡C—, —O—, —S—, —S(O)—, —S(O)$_2$—, —SO$_2$N($R^4$)—, —N(R—$^4$)—, —N($R^4$)C(O)—, —NR$^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —N($R^4$)—N($R^4$)—, —N($R^4$)SO$_2$—, or —SO$_2$N($R^4$)—, and wherein $T^3$ or a portion thereof optionally forms part of a 3-7 membered ring;

V is —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —NR$^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —C(NR$^4$)=N—, —C(OR$^5$)=N—, —N($R^4$)—N($R^4$)—, —N($R^4$)SO$_2$—, —N($R^4$)SO$_2$N($R^4$)—, —P(O)($R^5$)—, —P(O)(OR$^5$)—O—, —P(O)O—, or —P(O)(NR$^5$)—N($R^5$)—;

$R^{2d}$ is -halo, —NO$_2$, —CN, —C($R^5$)=C($R^5$)$_2$, —C($R^5$)=C($R^5$)($R^{10}$), —C≡C—$R^5$, —C≡C—$R^{10}$, —OR$^5$, —SR$^6$, —S(O)$R^6$, —SO$_2$$R^6$, —SO$_3$$R^5$, —SO$_2$N($R^4$)$_2$, —N($R^4$)$_2$, —NR$^4$C(O)$R^5$, —NR$^4$C(O)N($R^4$)$_2$, —NR$^4$CO$_2$$R^6$, —O—CO$_2$$R^5$, —OC(O)N($R^4$)$_2$, —O—C(O)$R^5$, —CO$_2$$R^5$, —C(O)—$R^5$, —C(O)$R^5$, —C(O)N($R^4$)$_2$, —C(O)N($R^4$)C(=NR$^4$)—N($R^4$)$_2$, —N($R^4$)C(=NR$^4$)—N($R^4$)—C(O)$R^5$, —C(=NR$^4$)—N($R^4$)$_2$, —C(=NR$^4$)—OR$^5$, —N($R^4$)—N($R^4$)$_2$, —N($R^4$)C(=NR$^4$)—N($R^4$)$_2$, —N($R^4$)SO$_2$$R^6$, —N($R^4$)SO$_2$N($R^4$)$_2$, —P(O)($R^5$)$_2$, or —P(O)(OR$^5$)$_2$;

each $R^{7d}$ independently is an optionally substituted aryl, heterocyclyl, or heteroaryl group;

each $R^{9d}$ independently is —C(O)$R^5$, —C(O)N($R^4$)$_2$, —CO$_2$$R^6$, —SO$_2$$R^6$, —SO$_2$N($R^4$)$_2$, or a $C_{1-4}$ aliphatic optionally substituted with $R^3$ or $R^7$;

each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl);

each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;

each $R^4$ independently is hydrogen or an optionally substituted aliphatic, aryl, heteroaryl or heterocyclyl group; or two $R^4$ on the same nitrogen atom, taken together with the nitrogen atom, form an optionally substituted 5- to 6-membered heteroaryl or 4- to 8-membered heterocyclyl having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group;

each $R^7$ independently is an optionally substituted aryl, heterocyclyl, or heteroaryl group; and each $R^{10}$ independently is —CO$_2$$R^5$ or —C(O)N($R^4$)$_2$.

17. The compound of claim 16, wherein:

$R^e$ is hydrogen;

$R^{b2}$ and $R^{b3}$ are each independently selected from the group consisting of hydrogen, -halo, $C_{1-3}$ aliphatic, $C_{1-3}$ fluoroaliphatic, and —OR$^5$, where $R^5$ is hydrogen or $C_{1-3}$ aliphatic; and $R^{c1}$ and $R^{c5}$ are each independently selected from the group consisting of hydrogen, -halo, $C_{1-3}$ aliphatic, $C_{1-3}$ fluoroaliphatic, and —OR$^5$, where $R^5$ is hydrogen or $C_{1-3}$ aliphatic.

18. The compound of claim 17, wherein $R^{b3}$ and $R^{c1}$ are each independently selected from the group consisting of -halo, $C_{1-3}$ aliphatic, $C_{1-3}$ fluoroaliphatic, and —OR$^5$, where $R^5$ is hydrogen or $C_{1-3}$ aliphatic.

19. The compound of claim 18, wherein $R^{b3}$ and $R^{c1}$ are each independently chloro, fluoro, bromo, methyl, trifluoromethyl, or methoxy.

20. The compound of claim 11, wherein:

Ring C is a mono- or bicyclic aryl, heteroaryl, heterocyclyl or carbocyclic ring, which is substituted with 0-2 independently selected substituents $R^d$ and 0-2 independently selected $R^{2d}$ or $C_{1-6}$ aliphatic groups;

each $R^d$ independently is selected from the group consisting of $C_{1-3}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$;

V is —C($R^5$)=C($R^5$)—, —C≡C—, —O—, —N($R^4$)—, —C(O)— or —C(O)N($R^4$)—;

$T^2$ is a $C_{1-6}$ alkylene chain, wherein $T^2$ optionally is substituted with one or two substituents independently selected from the group consisting of -halo, —$C_{1-3}$ aliphatic, —OH, and —O($C_{1-3}$ alkyl), or two substituents on the same carbon atom, taken together with the carbon atom to which they are attached, form a 3- to 6-membered carbocyclic ring, and wherein $T^2$ optionally is interrupted by —C($R^5$)=C($R^5$)—, —C≡C—, —O—, —C(O)—, —C(O)N($R^4$)—, —N($R^4$)C(O)—or —N($R^4$)—; and $T^3$ is a $C_{1-4}$ alkylene chain, wherein $T^3$ optionally is substituted with one or two substituents independently selected from the group consisting of -halo, —$C_{1-3}$ aliphatic, —OH, and —O($C_{1-3}$ alkyl), or two substituents on the same carbon atom, taken together with the carbon atom to which they are attached, form a 3- to 6-membered carbocyclic ring, and wherein $T^3$ optionally is interrupted by —C($R^5$)=C($R^5$)—, —C≡C—, —O—, —C(O)—, —C(O)N($R^4$)—, —N($R^4$)C(O)—or —N($R^4$)—;

$R^{2d}$ is -halo, —NO$_2$, —CN, —C($R^5$)=C($R^5$)$_2$, —C≡C—$R^5$, —OR$^5$, —SR$^6$, —S(O)$R^6$, —SO$_2$$R^6$, —SO$_3$$R^5$, —SO$_2$N($R^4$)$_2$, —N($R^4$)$_2$, —NR$^4$C(O)$R^5$, —NR$^4$C(O)N($R^4$)$_2$, —NR$^4$CO$_2$$R^6$, —O—CO$_2$$R^5$, —OC(O)N($R^4$)$_2$, —O—C(O)$R^5$, —CO$_2$$R^5$, —C(O)—C(O)$R^5$, —C(O)$R^5$, —C(O)N($R^4$)$_2$, —C(O)N($R^4$)C(=NR$^4$)—N($R^4$)$_2$, —N($R^4$)C(=NR$^4$)—N($R^4$)—C(O)$R^5$, —C(=NR$^4$)—N($R^4$)$_2$, —C(=NR$^4$)—OR$^5$, —N($R^4$)—N($R^4$)$_2$, —N($R^4$)C(=NR$^4$)—N($R^4$)$_2$, —N($R^4$)SO$_2$$R^6$, —N($R^4$)SO$_2$N($R^4$)$_2$, —P(O)($R^5$)$_2$, —P(O)(OR$^5$)$_2$; and each $R^{7d}$ independently is an optionally substituted aryl, heterocyclyl, or heteroaryl group.

21. The compound of claim 20, wherein Ring C is a substituted or unsubstituted ring selected from the group consisting of phenyl, pyridyl, pyrimidinyl, pyrazinyl, pyridazinyl, imidazolyl, pyrazolyl, thiazolyl, oxazolyl, benzimidazolyl, benzthiazolyl, benzoxazolyl, and phthalimidyl.

22. The compound of claim 21, wherein:
each $R^d$ independently is selected from the group consisting of $C_{1-3}$ aliphatic, $R^{2d}$, $R^{7d}$, $-T^2-R^{2d}$, $-T^2-R^{7d}$, $-V-T^3-R^{2d}$, and $-V-T^3-R^{7d}$; and
each $R^{2d}$ independently is selected from the group consisting of -halo, $-OR^5$, $-N(R^4)_2$, $-CO_2R^5$, $-C(O)N(R^4)_2$, $-SO_2N(R^4)_2$, $-C(=NR^4)N(R^4)_2$, $-C(O)N(R^4)C(=NR^4)-N(R^4)_2$, $-N(R^4)C(=NR^4)-N(R^4)-C(O)R^5$, and $-NR^4C(O)R^5$.

23. The compound of claim 22, wherein Ring C is substituted with at least one $R^{7d}$ selected from the group consisting of:

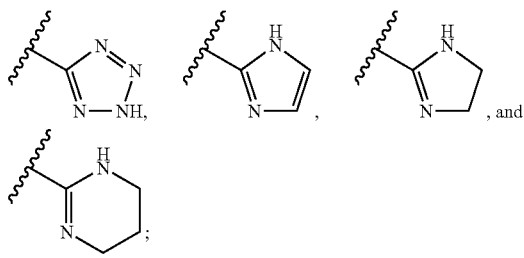

any of which groups optionally is substituted on any substitutable ring carbon or ring nitrogen atom.

24. The compound of claim 22, wherein Ring C is substituted with at least one $-T^2-R^{2d}$ or $-T^2-R^{7d}$, where:
$T^2$ is a $C_{1-6}$ alkylene chain, wherein $T^2$ optionally is substituted with one or two substituents independently selected from the group consisting of -halo, $-C_{1-3}$ aliphatic, $-OH$, and $-O(C_{1-3}$ aliphatic), or two substituents on the same carbon atom, taken together with the carbon atom to which they are attached, form a 3- to 6-membered carbocyclic ring, and wherein $T^2$ optionally is interrupted by $-C(R^5)=C(R^5)-$, $-C\equiv C-$, $-O-$, $-C(O)-$, $-NR^4C(O)R^5-$, $-N(R^4)C(O)-$ or $-N(R^4)-$; and
$R^{2d}$ is selected from the group consisting of -halo, $-OR^5$, $-N(R^4)_2$, $-N(R^4)C(O)R^5$, $-CO_2R^5$, $-C(O)N(R^4)_2$, $-SO_2N(R_4)_2$, $-C(O)N(R^4)C(=NR^4)-N(R^4)_2$, and $-N(R^4)C(=NR^4)-N(R^4)-C(O)R^5$.

25. The compound of claim 24, wherein Ring C is substituted with one $-T^2-R^{2d}$ or $-T^2-R^{7d}$, and optionally one other substituent selected from the group consisting of hydrogen, -halo, $C_{1-3}$ aliphatic, and $-OR^5$, where $R^5$ is hydrogen or $C_{1-3}$ aliphatic.

26. The compound of claim 22, wherein Ring C is substituted with at least one $-V-T^3-R^{2d}$ or $-V-T^3-R^{7d}$, where:
V is $-N(R^4)-$, $-O-$, $-C(O)N(R^4)-$, $-C(O)-$, or $-C\equiv C-$;
$T^3$ is a $C_{1-4}$ alkylene chain, which is optionally substituted by one or two substituents independently selected from the group consisting of -halo, $-C_{1-3}$ aliphatic, $-OH$, and $-O(C_{1-3}$ aliphatic), or two substituents on the same carbon atom, taken together with the carbon atom to which they are attached, form a 3- to 6-membered carbocyclic ring; and
$R^{2d}$ is selected from the group consisting of -halo, $-OR^5$, $-N(R^4)_2$, $-NR^4C(O)R^5$, $-CO_2R^5$, $-C(O)N(R^4)_2$, and $-SO_2N(R_4)_2$.

27. The compound of claim 26, wherein Ring C is substituted with one $-V-T^3-R^{2d}$ or $-V-T^3-R^{7d}$, and optionally one other substituent selected from the group consisting of hydrogen, -halo, $C_{1-3}$ aliphatic, and $-OR^5$, where $R^5$ is hydrogen or $C_{1-3}$ aliphatic.

28. The compound of claim 27, wherein:
V is $-C(O)N(R^4)-$;
$T^3$ is a $C_{2-4}$ alkylene chain;
$R^{2d}$ is $-N(R^4)_2$, where each $R^4$ independently is hydrogen or $C_{1-3}$ aliphatic, or $-N(R^4)_2$ is an optionally substituted 5- to 6-membered heteroaryl or 4- to 8-membered heterocyclyl ring having, in addition to the nitrogen, 0-2 ring heteroatoms selected from N, O, and S; and
$R^{7d}$ is an optionally substituted 4- to 8-membered heterocyclyl or an optionally substituted 5- to 6-membered heteroaryl.

29. The compound of claim 28, wherein:
$R^{2d}$ is $-N(R^4)_2$, and $-N(R^4)_2$ is an optionally substituted heterocyclyl selected from the group consisting of piperidinyl, piperazinyl, morpholinyl, pyrrolidinyl, and azetidinyl; and
$R^{7d}$ is an optionally substituted heteroaryl selected from the group consisting of pyridyl, pyridazinyl, pyrimidinyl, pyrazinyl, pyrrolyl, oxazolyl, imidazolyl, and pyrazolyl.

30. The compound of claim 22, wherein Ring C is substituted with one or two substituents independently selected from the group consisting of $C_{1-3}$ aliphatic, -halo, $-OR^5$, $-CO_2R^5$, $-C(O)N(R^4)_2$, $-SO_2N(R^4)_2$, $-C(=NR^4)N(R^4)_2$, $-C(O)N(R^4)C(=NR^4)-N(R^4)_2$, $-N(R^4)C(=NR^4)-N(R^4)-C(O)R^5$, and $-NR^4C(O)R^5$.

31. The compound of claim 30, wherein Ring C is substituted with at least one substituent selected from the group consisting of $-CO_2R^5$, $-C(O)N(R^4)_2$, $-C(=NR^4)N(R^4)_2$, $-C(O)N(R^4)C(=NR^4)-N(R^4)_2$, $-N(R^4)C(=NR^4)-N(R^4)-C(O)R^5$, and $-NR^4C(O)R^5$.

32. The compound of claim 30, wherein Ring C is substituted with at least one $-CO_2R^5$, where $R^5$ is hydrogen or $C_{1-6}$ aliphatic.

33. The compound of claim 30, wherein:
Ring C is substituted with at least one $-C(O)-N(R^4)_2$, $-C(=NR^4)N(R^4)_2$, or $-NR^4C(O)R^5$; where
$-N(R^4)_2$ is an optionally substituted 4- to 8-membered heterocyclyl ring having, in addition to the nitrogen atom, 0-2 ring heteroatoms selected from N, O, and S; and
$R^5$ is a 4- to 8-membered nitrogen-containing heterocyclyl ring.

34. The compound of claim 33, wherein Ring C is substituted with at least one $-C(O)N(R^4)_2$ or $-C(=NR^4)N(R^4)_2$, and $-N(R^4)_2$ is an optionally substituted heterocyclyl selected from the group consisting of piperidinyl, piperazinyl, morpholinyl, pyrrolidinyl, and azetidinyl.

35. The compound of claim 34, wherein Ring C is substituted with at least one substituent having the formula:

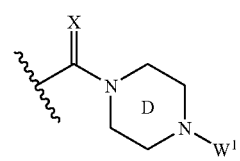

wherein:
Ring D optionally is substituted on one or two ring carbon atoms;
X is O or NH;

W¹ is hydrogen, —C(O)R⁵, —C(O)N(R⁴)₂, —CO₂R⁶, —SO₂R⁶, —SO₂N(R⁴)₂, or an optionally substituted aliphatic, aryl, heteroaryl, or heterocyclyl group.

36. The compound of claim 34, wherein Ring C is substituted with at least one substituent having the formula:

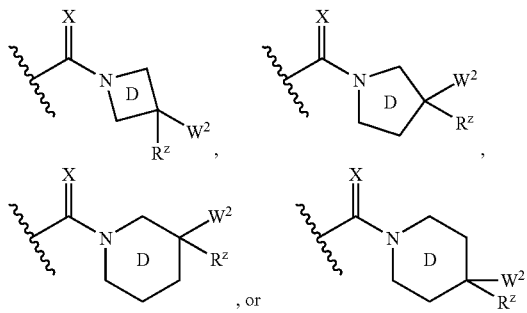

wherein:

Ring D optionally is substituted on one or two substitutable ring carbon atoms;

X is O or NH;

W² is R″ or -T⁶-R″;

T⁶ is a C₁₋₃ alkylene chain optionally substituted with R³ or R³ᵇ; and

R″ is —N(R⁴)₂ or —C(O)N(R⁴)₂; and

Rᶻ is hydrogen, —CO₂R⁵, C(O)N(R⁴)₂, —C(O)R⁵, or a C₁₋₃ aliphatic optionally substituted with R³ or R⁷; or Rᶻ and W², taken together with the carbon atom to which they are attached, form a 4- to 7-membered cycloaliphatic or heterocyclyl ring.

37. The compound of claim 34, wherein at least one substituent on Ring C is selected from the group consisting of:

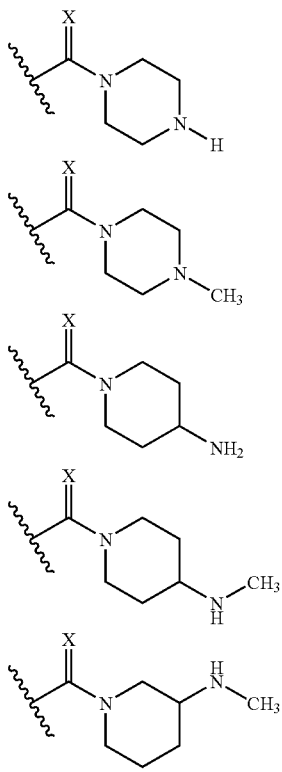

-continued

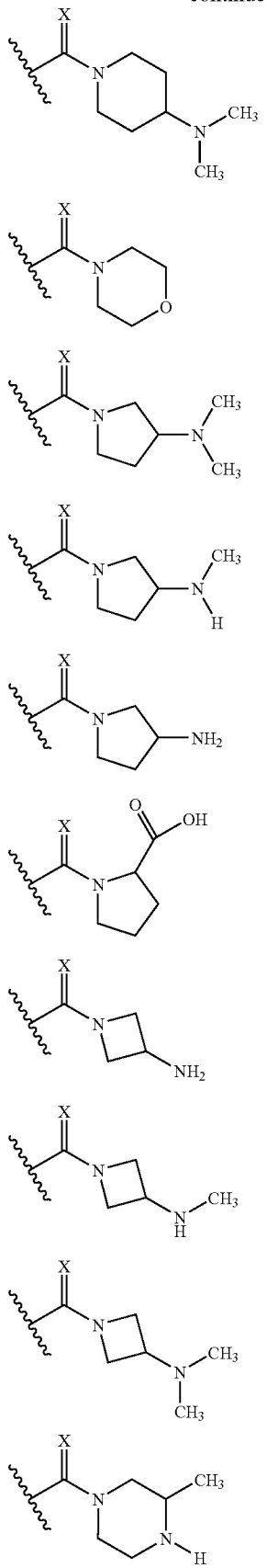

-continued
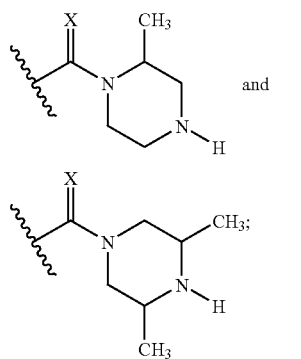
where X is O or NH.
38. The compound of claim 34, wherein at least one substituent on Ring C is selected from the group consisting of:
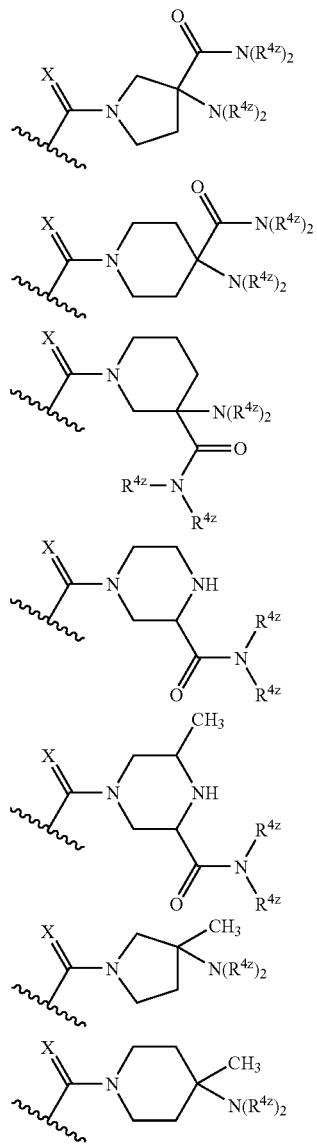
-continued
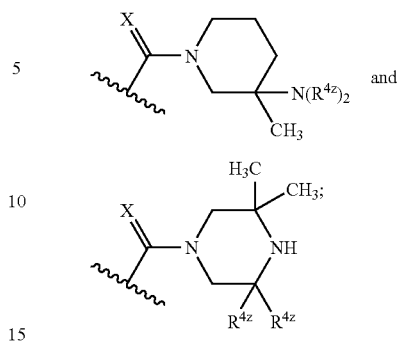
where X is O or NH, and each $R^{4z}$ independently is hydrogen or —$CH_3$.
39. The compound of claim 33, wherein Ring C is substituted with a group selected from the group consisting of:
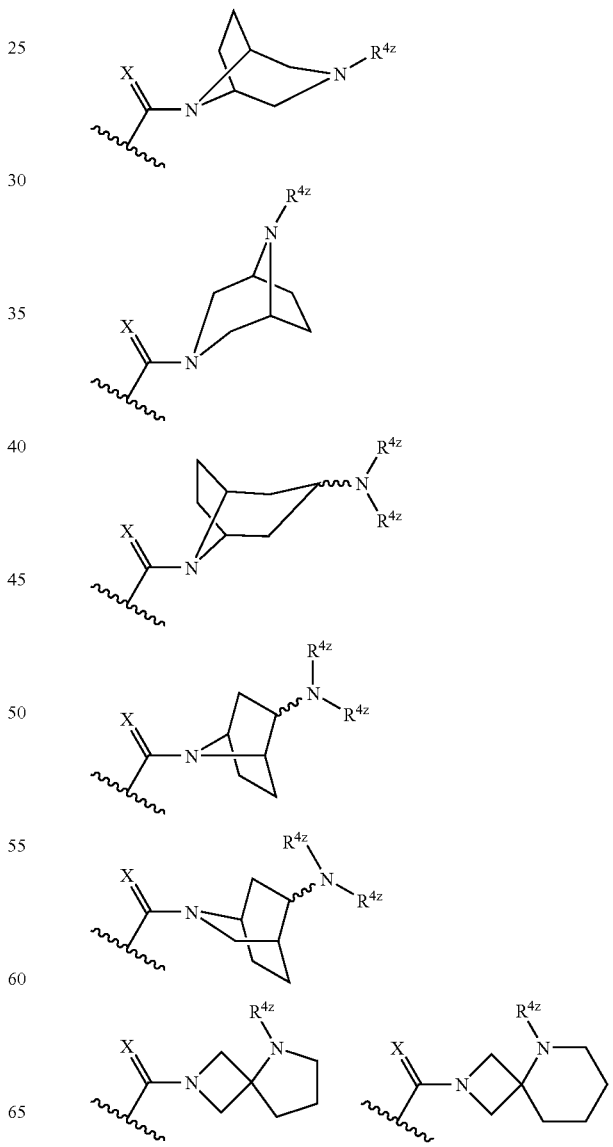

-continued

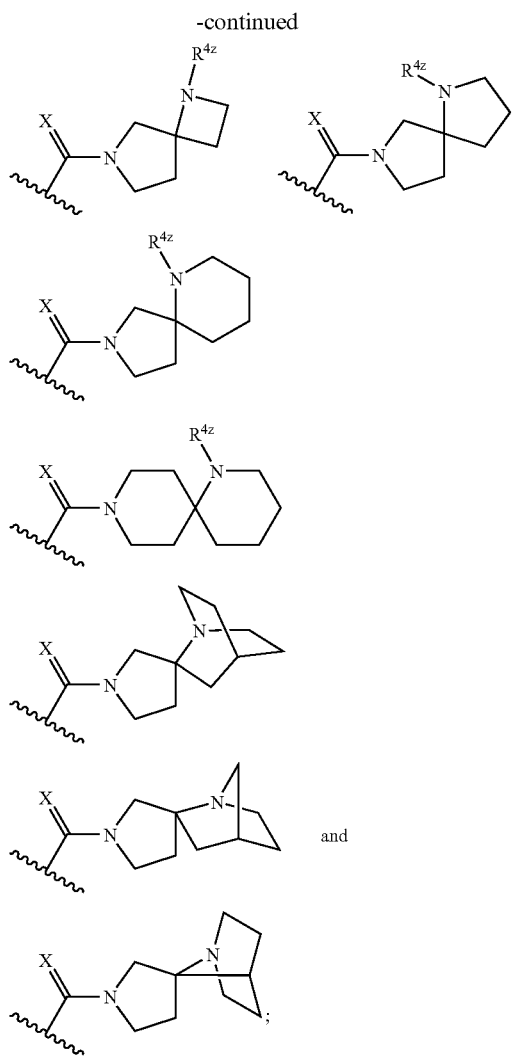

where X is O or NH, and each $R^{4z}$ independently is hydrogen or —CH$_3$.

40. The compound of claim 31, wherein Ring C is substituted with at least one —C(O)N(R$^4$)$_2$ or —C(=NH)N(R$^4$)$_2$, where one R$^4$ is hydrogen or C$_{1-3}$ alkyl, and the other R$^4$ is an optionally substituted heterocyclyl or heterocyclylalkyl.

41. The compound of claim 40, wherein Ring C is substituted with at least one substituent selected from the group consisting of

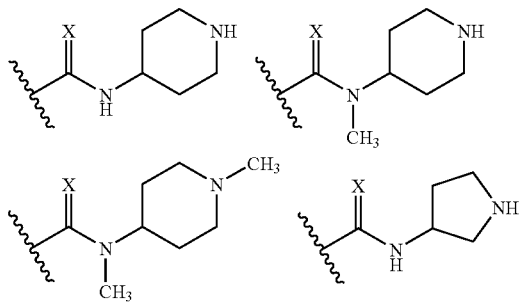

-continued

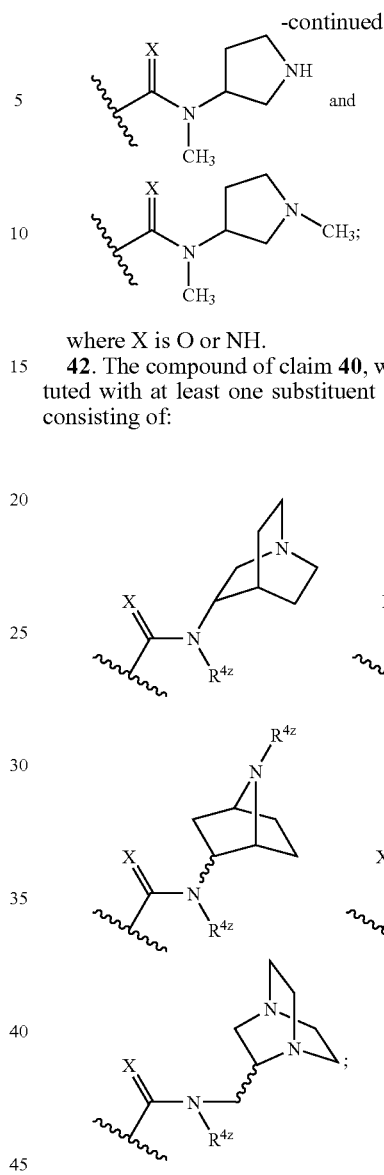

where X is O or NH.

42. The compound of claim 40, wherein Ring C is substituted with at least one substituent selected from the group consisting of:

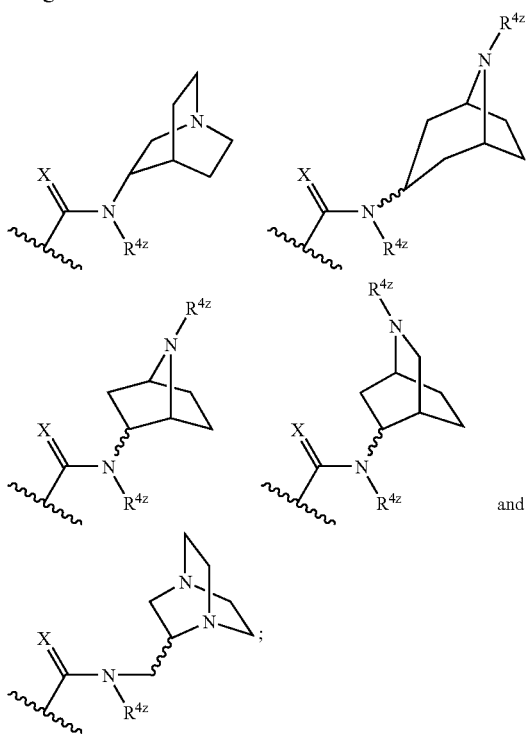

where X is O or NH, and each $R^{4z}$ independently is H or CH$_3$.

43. The compound of claim 11, having formula (VI):

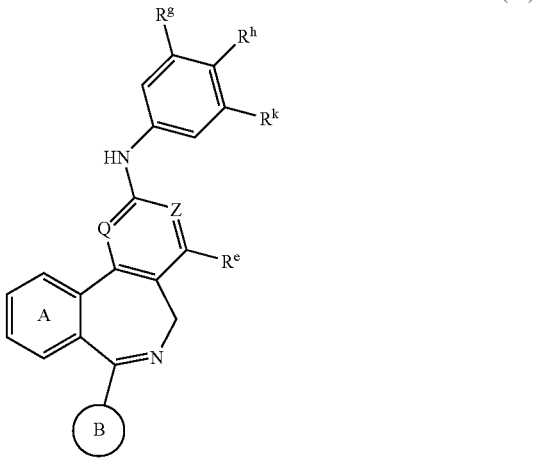

(VI)

wherein:
R$^g$ is selected from the group consisting of hydrogen, C$_{1-6}$ aliphatic, and R$^{2d}$;
R$^h$ and R$^k$ are each independently hydrogen or R$^d$;
each R$^d$ independently is selected from the group consisting of C$_{1-3}$ aliphatic, R$^{2d}$, R$^{7d}$, -T$^2$-R$^{2d}$, -T$^2$-R$^{7d}$, —V-T$^3$-R$^{2d}$, and —V-T$^3$-R$^{7d}$; and
each R$^{2d}$ independently is selected from the group consisting of -halo, —OR$^5$, —CO$_2$R$^5$, —C(O)N(R$^4$)$_2$, —SO$_2$N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —NR$^4$C(O)R$^5$.

44. The compound of claim 43, wherein:
R$^g$ is hydrogen;
R$^h$ is —CO$_2$R$^5$, —C(O)N(R$^4$)$_2$, —C(=NR$^4$)N(R$^4$)$_2$, or —N(R$^4$)C(O)R$^5$; and
R$^k$ is hydrogen, halo, C$_{1-3}$ aliphatic, or —OR$^5$.

45. A compound of formula (VII):

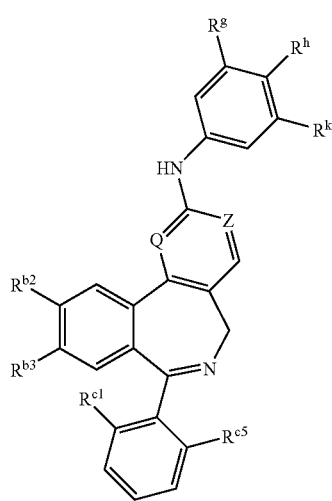

(VII)

or a pharmaceutically acceptable salt thereof;
wherein:
one of Q and Z is —N—, and the other is —CH—;
R$^{b2}$ and R$^{b3}$ are each independently selected from the group consisting of hydrogen, -halo, C$_{1-3}$ aliphatic, C$_{1-3}$ fluoroaliphatic, and —OR$^5$, where each R$^5$ in R$^{b2}$ and R$^{b3}$ independently is hydrogen or C$_{1-3}$ aliphatic;
R$^{c1}$ and R$^{c5}$ are each independently selected from the group consisting of hydrogen, -halo, C$_{1-3}$ aliphatic, C$_{1-3}$ fluoroaliphatic, and —OR$^5$, where each R$^5$ in R$^{c1}$ and R$^{c5}$ independently is hydrogen or C$_{1-3}$ aliphatic;
R$^g$ is selected from the group consisting of hydrogen, C$_{1-6}$ aliphatic, and R$^{2d}$;
R$^h$ and R$^k$ are each independently hydrogen or R$^d$;
each R$^d$ independently is selected from the group consisting of C$_{1-3}$ aliphatic, R$^{2d}$, R$^{7d}$, -T$^2$-R$^{2d}$, -T$^2$-R$^{7d}$, —V-T$^3$-R$^{2d}$, and —V-T$^3$-R$^{7d}$;
T$^2$ is a C$_{1-6}$ alkylene chain optionally substituted with R$^3$ or R$^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —N(R$^4$)—N(R$^4$)—, —N(R$^4$)SO$_2$—, or —SO$_2$N(R$^4$)—, and wherein T$^2$ or a portion thereof optionally forms part of a 3-7 membered ring;
T$^3$ is a C$_{1-6}$ alkylene chain optionally substituted with R$^3$ or R$^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —N(R$^4$)—N(R$^4$)—, —N(R$^4$)SO$_2$—, or —SO$_2$N(R$^4$)—, and wherein T$^3$ or a portion thereof optionally forms part of a 3-7 membered ring;
V is —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —C(NR$^4$)=N—, —C(OR$^5$)=N—, —N(R$^4$)—, —(R$^4$)SO$_2$—, —N(R$^4$)SO$_2$N(R$^4$)—, —P(O)(R$^5$)—, —P(O)(OR$^5$)—O—, —P(O)—O—, or —P(O)(NR$^5$)—N(R$^5$)—;
each R$^{2d}$ independently is selected from the group consisting of -halo, —OR$^5$, —CO$_2$R$^5$, —C(O)N(R$^4$)$_2$, —SO$_2$N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —NR$^4$C(O)R$^5$;
each R$^{7d}$ independently is an optionally substituted aryl, heterocyclyl, or heteroaryl group;
each R$^3$ independently is selected from the group consisting of -halo, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, and —C(O)NH(C$_{1-3}$ alkyl);
each R$^{3b}$ independently is a C$_{1-3}$ aliphatic optionally substituted with R$^3$ or R$^7$, or two substituents R$^{3b}$ on the same carbon atom, taken together with the carbon atom to which they are attached, form a 3- to 6-membered carbocyclic ring;
each R$^4$ independently is hydrogen or an optionally substituted aliphatic, aryl, heteroaryl, or heterocyclyl group; or two R$^4$ on the same nitrogen atom, taken together with the nitrogen atom, form an optionally substituted 5- to 6-membered heteroaryl or 4- to 8-membered heterocyclyl having, in addition to the nitrogen atom, 0-2 ring heteroatoms selected from N, O, and S;
each R$^5$ in R$^g$, R$^h$, and R$^k$ independently is hydrogen or an optionally substituted aliphatic, aryl, heteroaryl, or heterocyclyl group; and
each R$^7$ independently is an optionally substituted aryl, heterocyclyl, or heteroaryl group.

46. The compound of claim 45, wherein R$^g$, R$^h$, and R$^k$ are each independently selected from the group consisting of hydrogen, C$_{1-3}$ aliphatic, -halo, —OR$^5$, —CO$_2$R$^5$, —C(O)N(R$^4$)$_2$, —SO$_2$N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —N(R$^4$)C(O)R$^5$.

47. The compound of claim 46, wherein at least one of R$^h$ and R$^k$ is selected from the group consisting of —CO$_2$R$^5$, —C(O)N(R$^4$)$_2$, —C(=NR$^4$)N(R$^4$)$_2$, —C(O)N(R$^4$)C(=NR$^4$)—N(R$^4$)$_2$, —N(R$^4$)C(=NR$^4$)—N(R$^4$)—C(O)R$^5$, and —N(R$^4$)C(O)R$^5$.

48. The compound of claim 45, wherein:
R$^{b2}$, and R$^g$ are each hydrogen;
R$^{b3}$ and R$^{c1}$ are each independently selected from the group consisting of -halo, C$_{1-3}$ aliphatic, C$_{1-3}$ fluoroaliphatic, and —OR$^5$, where each R$^5$ in R$^{b3}$ and R$^{c1}$ independently is hydrogen or C$_{1-3}$ aliphatic;
R$^{c5}$ is selected from the group consisting of hydrogen, -halo, C$_{1-3}$ aliphatic, C$_{1-3}$ fluoroaliphatic, and —OR$^5$, where R$^5$ in R$^{c5}$ is hydrogen or C$_{1-3}$ aliphatic; and $R^h$ is —$CO_2H$, —$C(O)N(R^4)_2$, —$C(\!=\!NR^4)N(R^4)_2$, —$C(O)N(R^4)C(\!=\!NR^4)$—$N(R^4)_2$, or —$N(R^4)C(\!=\!NR^4)$—$N(R^4)$—$C(O)R^5$, where $R^5$ in $R^h$ is an optionally substituted 4- to 8-membered nitrogen-containing heterocyclyl ring, and —$N(R^4)_2$ is an optionally substituted 4 to 8-membered heterocyclyl ring having in addition to the nitrogen atom 0-2 heteroatoms selected from N, O, and S; and $R^k$ is hydrogen, halo, $C_{1-3}$ aliphatic, or —$OR^5$, where the $R^5$ in $R^k$ is hydrogen or $C_{1-3}$ aliphatic.

49. A compound of formula (VIII):

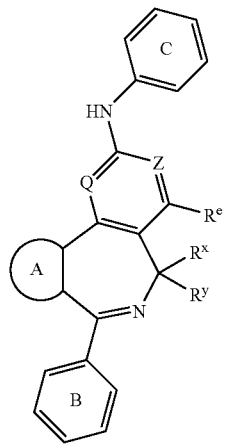

(VIII)

or a pharmaceutically acceptable salt thereof, wherein:
one of Q and Z is —N—, and the other is —CH—;
$R^e$ is hydrogen, —OH, —$NHR^4$, —SH, or a $C_{1-3}$ aliphatic optionally substituted with $R^3$ or $R^7$;
$R^x$ and $R^y$ are each independently hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;
Ring A is a substituted or unsubstituted 5- or 6-membered aryl, heteroaryl, cycloaliphatic, or heterocyclyl ring;
Ring B is substituted with 0-2 independently selected substituents $R^c$, and 0-3 substituents independently selected from the group consisting of $R^{2c}$ and $C_{1-6}$ aliphatic groups;
each $R^c$ independently is selected from the group consisting of $C_{1-6}$ aliphatic, $R^{2c}$, $R^{7c}$, -$T^1$-$R^{2c}$, and -$T^1$-$R^{7c}$;
$T^1$ is a $C_{1-6}$ alkylene chain optionally substituted with $R^3$ or $R^{3b}$, wherein $T^1$ or a portion thereof optionally forms part of a 3- to 7-membered ring;
$R^{2c}$ is -halo, —$NO_2$, —CN, —$C(R^5)\!=\!C(R^5)_2$, —$C(R^5)\!=\!C(R^5)(R^{10})$, —C≡C—$R^5$, —C≡C—$R^{10}$, —$OR^5$, —$SR^6$, —$S(O)R^6$, —$SO_2R^6$, —$SO_3R^5$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —$OC(O)N(R^4)_2$, —O—$C(O)R^5$, —$CO_2R^5$, —C(O)—$C(O)R^5$, —$C(O)R^5$, —$C(O)N(R^4)_2$, —$C(\!=\!NR^4)$—$N(R^4)_2$, —$C(\!=\!NR^4)$—$OR^5$, —$N(R^4)$—$N(R^4)_2$, —$N(R^4)C(\!=\!NR^4)$—$N(R^4)$, —$N(R^4)SO_2R^6$, —$N(R^4)SO_2N(R^4)_2$, —$P(O)(R^5)_2$, or —$P(O)(OR^5)_2$;
each $R^{7c}$ independently is an optionally substituted aryl, heterocyclyl, or heteroaryl group;
Ring C is substituted with 0-2 independently selected substituents $R^d$ and 0-3 substituents independently selected from the group consisting of $R^{2d}$ or $C_{1-6}$ aliphatic groups;
each $R^d$ independently is selected from the group consisting of $C_{1-6}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$;

$T^2$ is a $C_{1-6}$ alkylene chain optionally substituted with $R^3$ or $R^{3b}$, wherein the alkylene chain optionally is interrupted by —$C(R^5)\!=\!C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —$OC(O)O$—, —$OC(O)N(R^4)$—, —$N(R^4)$—$N(R^4)$—, —$N(R^4)SO_2$—, or —$SO_2N(R^4)$—, and wherein $T^2$ or a portion thereof optionally forms part of a 3-7 membered ring;
$T^3$ is a $C_{1-6}$ alkylene chain optionally substituted with $R^3$ or $R^{3b}$, wherein the alkylene chain optionally is interrupted by —$C(R^5)\!=\!C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —$OC(O)O$—, —$OC(O)N(R^4)$—, —$N(R^4)$—$N(R^4)$—, —$N(R^4)SO_2$—, or —$SO_2N(R^4)$—, and wherein $T^3$ or a portion thereof optionally forms part of a 3-7 membered ring;
V is —$C(R^5)\!=\!C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —$OC(O)O$—, —$OC(O)N(R^4)$—, —$C(NR^4)\!=\!N$—, —$C(OR^5)\!=\!N$—, —$N(R^4)$—$N(R^4)$—, —$N(R^4)SO_2$—, —$N(R^4)SO_2N(R^4)$—, —$P(O)(R^5)$—, —$P(O)(OR^5)$—O—, —P(O)—O—, or —$P(O)(NR^5)$—$N(R^5)$—;
$R^{2d}$ is -halo, —$NO_2$, —CN, —$C(R^5)\!=\!C(R^5)_2$, —$C(R^5)\!=\!C(R^5)(R^{10})$, —C≡C—$R^5$, —C≡C—$R^{10}$, —$OR^5$, —$SR^6$, —$S(O)R^6$, —$SO_2R^6$, —$SO_3R^5$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —$OC(O)N(R^4)_2$, —O—$C(O)R^5$, —$CO_2R^5$, —C(O)—$C(O)R^5$, —$C(O)R^5$, —$C(O)N(R^4)_2$, —$C(O)N(R^4)C(\!=\!NR^4)$—$N(R^4)_2$, —$N(R^4)C(\!=\!NR^4)$—$N(R^4)$—$C(O)R^5$, —$C(\!=\!NR^4)$—$N(R^4)_2$, —$C(\!=\!NR^4)$—$OR^5$, —$N(R^4)$—$N(R^4)_2$, —$N(R^4)C(\!=\!NR^4)$—$N(R^4)_2$, —$N(R^4)SO_2R^6$, —$N(R^4)SO_2N(R^4)_2$, —$P(O)(R^5)_2$, or —$P(O)(OR^5)_2$;
each $R^{7d}$ independently is an optionally substituted aryl, heterocyclyl, or heteroaryl group;
each $R^{3b}$ independently is selected from the group consisting of -halo, —OH, —O($C_{1-3}$ alkyl), —CN, —$N(R^4)_2$, —$C(O)(C_{1-3}$ alkyl), —$CO_2H$, —$CO_2(C_{1-3}$ alkyl), —$C(O)NH_2$, and —$C(O)NH(C_{1-3}$ alkyl);
each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;
each $R^5$ independently is hydrogen or an optionally substituted aliphatic, aryl, heteroaryl, or heterocyclyl group;
each $R^6$ independently is an optionally substituted aliphatic or aryl group;
each $R^7$ independently is an optionally substituted aryl, heteroaryl, or heterocyclyl group; and
each $R^{10}$ independently is —$CO_2R^5$ or —$C(O)N(R^4)_2$.

50. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,718,648 B2  Page 1 of 1
APPLICATION NO. : 11/890406
DATED : May 18, 2010
INVENTOR(S) : Christopher F. Claiborne et al.

It is certified that error appears in the above-identified patent and that said Letters Patent is hereby corrected as shown below:

In Column 83, Claim 7, Line 14, please delete, "—P(O)(OR$^5$)$_2$; and" and replace with -- —P(O)(OR$^5$)$_2$; and --

In Column 83, Claim 7, Line 31, please delete, "Same" and replace with -- same --

In Column 91, Claim 16, Line 13, please delete, "option ally" and replace with -- optionally --

In Column 91, Claim 16, Line 17, please delete, "—N(R—$^4$)—" and replace with-- —N(R$^4$)— --

In Column 93, Claim 22, Line 5, please delete, "-$T^2$" and replace with -- -T$^2$ --

In Column 101, Claim 43, Line 12, please delete, "—NR$^4$C(O)R$^5$." and replace with -- N(R$^4$)C(O)R$^5$. --

CLAIMS

In Column 102, Claim 45, Line 17, please delete, "—N(R$^4$)—, —(R$^4$)SO$_2$—," and replace with -- —N(R$^4$)—N(R$^4$) —, —N(R$^4$)SO$_2$—, --

In Column 103, Claim 48, Line 6, please delete, "substituted 4 to 8-membered" and replace with -- substituted 4- to 8-membered --

In Column 103, Claim 49, Line 56, please delete, "N(R$^4$)C(=NR$^4$)–N(R$^4$)" and replace with -- N(R$^4$)C(=NR$^4$)–N(R$^4$)$_2$ --

Signed and Sealed this
Eighteenth Day of January, 2011

David J. Kappos
*Director of the United States Patent and Trademark Office*